(12) United States Patent
Connor et al.

(10) Patent No.: US 7,589,238 B2
(45) Date of Patent: Sep. 15, 2009

(54) TREATMENT OF HYPERPHOSPHATEMIA USING CROSSLINKED SMALL MOLECULE AMINE POLYMERS

(75) Inventors: Eric Connor, Los Gatos, CA (US); Dominique Charmot, Campbell, CA (US); Han Ting Chang, Livermore, CA (US); Florence Roger, Santa Clara, CA (US); Gerrit Klaemer, San Jose, CA (US); Son Hoai Nguyen, San Jose, CA (US); Jonathan Mills, San Jose, CA (US); Jerry M. Buysse, Los Altos, CA (US); Angela Lee, San Jose, CA (US); Deidre Madsen, Sunnyvale, CA (US); Jun Shao, Fremont, CA (US); Michael J. Cope, Berkeley, CA (US); John Fordtran, Dallas, TX (US)

(73) Assignee: Ilypsa, Inc., Thousand Oaks, CA (US)

( * ) Notice: Subject to any disclaimer, the term of this patent is extended or adjusted under 35 U.S.C. 154(b) by 95 days.

(21) Appl. No.: 11/465,444

(22) Filed: Aug. 17, 2006

(65) Prior Publication Data

US 2007/0110706 A1 May 17, 2007

Related U.S. Application Data

(60) Division of application No. 10/980,991, filed on Nov. 3, 2004, which is a continuation-in-part of application No. 10/965,044, filed on Oct. 13, 2004, and a continuation-in-part of application No. 10/806,495, filed on Mar. 22, 2004, now Pat. No. 7,335,795, and a continuation-in-part of application No. 10/701,385, filed on Nov. 3, 2003.

(51) Int. Cl.
C07C 211/11 (2006.01)
C08G 2/00 (2006.01)
(52) U.S. Cl. .................... 564/511; 564/512; 514/772.3; 525/526; 521/36
(58) Field of Classification Search ................. 564/511, 564/512; 514/772.3; 521/36; 525/526
See application file for complete search history.

(56) References Cited

U.S. PATENT DOCUMENTS

| | | | |
|---|---|---|---|
| 3,308,020 A | 3/1967 | Wolf et al. | |
| 3,499,960 A | 3/1970 | Macek et al. | |
| 3,692,895 A * | 9/1972 | Nelson et al. | 424/78.1 |
| 3,930,810 A | 1/1976 | Gattuso | |
| 3,974,272 A | 8/1976 | Polli et al. | |
| 4,015,939 A | 4/1977 | Lewin et al. | |
| 4,027,009 A | 5/1977 | Grier et al. | |
| 4,075,177 A | 2/1978 | Bonnet et al. | |
| 4,135,880 A | 1/1979 | Mangiardi et al. | |
| 4,410,688 A | 10/1983 | Denkewalter et al. | |
| 4,507,466 A | 3/1985 | Tomalia et al. | |
| 4,558,120 A | 12/1985 | Tomalia et al. | |
| 4,568,737 A | 2/1986 | Tomalia et al. | |
| 4,587,329 A | 5/1986 | Tomalia et al. | |
| 4,599,400 A | 7/1986 | Tomalia et al. | |
| 4,605,701 A | 8/1986 | Harada et al. | |
| 4,631,337 A | 12/1986 | Tomalia et al. | |
| 4,690,985 A | 9/1987 | Tomalia et al. | |
| 4,734,200 A | 3/1988 | Berry | |
| 4,737,550 A | 4/1988 | Tomalia | |
| 4,747,881 A | 5/1988 | Shaw et al. | |
| 4,902,501 A | 2/1990 | Bandi et al. | |
| 5,091,175 A | 2/1992 | Imondi et al. | |
| 5,254,669 A | 10/1993 | Blackborow | |
| 5,338,532 A | 8/1994 | Tomalia et al. | |
| 5,380,522 A | 1/1995 | Day | |
| 5,447,726 A | 9/1995 | Nomura | |
| 5,451,397 A | 9/1995 | Albright et al. | |
| 5,487,888 A | 1/1996 | Mandeville, III et al. | |
| 5,496,545 A | 3/1996 | Holmes-Farley et al. | |
| 5,530,092 A | 6/1996 | Meijer et al. | |
| 5,607,669 A | 3/1997 | Mandeville, III et al. | |
| 5,618,530 A | 4/1997 | Mandeville, III et al. | |
| 5,667,775 A | 9/1997 | Holmes-Farley et al. | |
| 5,679,717 A | 10/1997 | Mandeville, III et al. | |
| 5,693,675 A | 12/1997 | Mandeville, III et al. | |
| 5,698,662 A | 12/1997 | Stoelwinder et al. | |
| 5,702,696 A | 12/1997 | Mandeville, III et al. | |
| 5,807,582 A | 9/1998 | Cha | |
| 5,833,854 A * | 11/1998 | Zwijnenburg et al. | 210/500.37 |

FOREIGN PATENT DOCUMENTS

DE 10305807 A1 8/2004

(Continued)

OTHER PUBLICATIONS

Bilicki, C.V., et al., Effect of Anions on Adsorption of Bile Salts by Colestipol Hydrochloride, Pharmaceutical Research, 1989, pp. 794-797, vol. 6, No. 9, Plenum Publishing Corporation.

(Continued)

*Primary Examiner*—Robert D. Harlan
(74) *Attorney, Agent, or Firm*—Senniger Powers LLP

(57) ABSTRACT

Anion-binding polymers are described. The anion-binding polymers in some cases are low swelling anion-binding polymers. In some cases, the anion-binding polymers have a pore volume distribution such that a fraction of the polymer is not available for non-interacting solutes above a certain percentage of the MW of the target ion for the polymer. In some cases, the anion-binding polymers are characterized by low ion-binding interference, where the interference is measured in, for example, a gastrointestinal simulant, relative to non-interfering buffer. Pharmaceutical composition, methods of use, and kits are also described.

66 Claims, 7 Drawing Sheets

U.S. PATENT DOCUMENTS

| | | | |
|---|---|---|---|
| 5,968,499 | A | 10/1999 | Hider et al. |
| 5,980,881 | A | 11/1999 | Mitsuka et al. |
| 5,985,938 | A | 11/1999 | Holmes-Farley et al. |
| 6,007,803 | A | 12/1999 | Mandeville, III et al. |
| 6,034,129 | A | 3/2000 | Mandeville, III et al. |
| 6,060,604 | A | 5/2000 | Yang et al. |
| 6,129,910 | A | 10/2000 | Holmes-Farley et al. |
| 6,132,706 | A | 10/2000 | Hider et al. |
| 6,180,094 | B1 | 1/2001 | Sasaki et al. |
| 6,180,754 | B1 | 1/2001 | Stutts et al. |
| 6,281,252 | B1 | 8/2001 | Holmes-Farley et al. |
| 6,333,051 | B1 | 12/2001 | Kabanov et al. |
| 6,361,768 | B1 | 3/2002 | Galleguillos et al. |
| 6,362,266 | B1 | 3/2002 | Buchholz et al. |
| 6,383,518 | B1 | 5/2002 | Matsuda et al. |
| 6,423,754 | B1 | 7/2002 | Holmes-Farley et al. |
| 6,471,968 | B1 | 10/2002 | Baker, Jr. et al. |
| 6,475,510 | B1 | 11/2002 | Venkatesh et al. |
| 6,509,013 | B1 | 1/2003 | Holmes-Farley et al. |
| 6,566,407 | B2 | 5/2003 | Holmes-Farley et al. |
| 6,593,366 | B2 | 7/2003 | Mandeville, III et al. |
| 6,646,083 | B2 | 11/2003 | Hirano et al. |
| 6,696,087 | B2 | 2/2004 | Matsuda et al. |
| 6,726,905 | B1 | 4/2004 | Mandeville, III et al. |
| 6,733,780 | B1 | 5/2004 | Tyler et al. |
| 6,767,549 | B2 | 7/2004 | Mandeville, III et al. |
| 2002/0028887 | A1 | 3/2002 | Hirano et al. |
| 2002/0034723 | A1 | 3/2002 | Leinenbach et al. |
| 2002/0054903 | A1 | 5/2002 | Tyler et al. |
| 2002/0064511 | A1 | 5/2002 | Simon et al. |
| 2002/0146386 | A1 | 10/2002 | Simon et al. |
| 2002/0168333 | A1 | 11/2002 | Burke |
| 2002/0182168 | A1 | 12/2002 | Holmes-Farley |
| 2002/0187120 | A1 | 12/2002 | Holmes-Farley et al. |
| 2002/0187121 | A1 | 12/2002 | Burke |
| 2003/0039627 | A1 | 2/2003 | Holmes-Farley et al. |
| 2003/0049226 | A1 | 3/2003 | Burke et al. |
| 2003/0078366 | A1 | 4/2003 | McDonnell et al. |
| 2003/0091530 | A1 | 5/2003 | Goto et al. |
| 2003/0092782 | A1 | 5/2003 | Goto et al. |
| 2004/0018169 | A1 | 1/2004 | Holmes-Farley et al. |
| 2004/0059065 | A1 | 3/2004 | Goto et al. |
| 2004/0120922 | A1 | 6/2004 | Burke |
| 2004/0170600 | A1 | 9/2004 | Simon et al. |
| 2004/0194334 | A1 | 10/2004 | Rea |
| 2005/0096438 | A1 | 5/2005 | Chang et al. |
| 2005/0131131 | A1 | 6/2005 | Connor et al. |
| 2005/0147580 | A1 | 7/2005 | Connor et al. |
| 2005/0165190 | A1 | 7/2005 | Chang et al. |
| 2005/0209423 | A1 | 9/2005 | Chang et al. |
| 2005/0239901 | A1 | 10/2005 | Chang et al. |
| 2005/0276781 | A1 | 12/2005 | Ross et al. |

FOREIGN PATENT DOCUMENTS

| | | | |
|---|---|---|---|
| EP | 0575596 | B1 | 12/1993 |
| EP | 0373852 | B1 | 10/1994 |
| EP | 0672703 | A1 | 9/1995 |
| EP | 0707611 | B1 | 4/1996 |
| EP | 0741756 | B1 | 11/1996 |
| EP | 0997148 | B1 | 5/2000 |
| EP | 0793960 | B1 | 8/2001 |
| EP | 1153940 | A1 | 11/2001 |
| EP | 1209146 | B1 | 5/2002 |
| EP | 1283046 | A1 | 2/2003 |
| EP | 1304104 | A2 | 4/2003 |
| JP | 1998059851 | A | 3/1998 |
| JP | 1998130154 | A | 5/1998 |
| JP | 2003155429 | | 5/2003 |
| WO | WO 82/00257 | | 2/1982 |
| WO | WO 93/14147 | A1 | 7/1993 |
| WO | 9419379 | | 9/1994 |
| WO | WO 94/27619 | A1 | 12/1994 |
| WO | WO 95/02008 | A1 | 1/1995 |
| WO | WO 95/05184 | A1 | 2/1995 |
| WO | WO 95/19384 | A1 | 7/1995 |
| WO | WO 95/20619 | A1 | 8/1995 |
| WO | WO 97/23514 | A1 | 7/1997 |
| WO | WO 97/49736 | A2 | 12/1997 |
| WO | WO 98/17707 | A1 | 4/1998 |
| WO | WO 98/42355 | A1 | 10/1998 |
| WO | WO 99/14297 | A1 | 3/1999 |
| WO | WO 99/40990 | A1 | 8/1999 |
| WO | WO 01/28527 | A2 | 4/2001 |
| WO | WO 01/38423 | A1 | 5/2001 |
| WO | WO 02/32974 | A2 | 4/2002 |
| WO | WO 02/32974 | A3 | 4/2002 |
| WO | WO 02/77074 | A1 | 10/2002 |
| WO | WO 2004/037274 | A1 | 5/2004 |
| WO | WO 2005/065291 | A2 | 7/2005 |
| WO | WO 2006/040579 | A1 | 4/2006 |

OTHER PUBLICATIONS

Bleyer, A.J., et al., A Comparison of the Calcium-Free Phosphate Binder Sevelamer Hydrochloride With Calcium Acetate in the Treatment of Hyperphosphatemia in Hemodialysis Patients, American Journal of Kidney Diseases, 1999, pp. 694-701, vol. 33, No. 4, National Kidney Foundation, Inc..

Covassin, L., et al., Synthesis of Spermidine and Norspermidine Dimers as High Affinity Polyamine Transport Inhibitors, Bioorganic & Medicinal Chemistry Letters, 1999, vol. 9, pp. 1709-1714, Elsevier Science Ltd..

Jansen, Bart A.J., et al., A Tetranuclear Platinum Compound Designed to Overcome Cisplatin Resistance, Eur. J. Inorg. Chem., 1999, pp. 1429-1433, Wiley-VCH Verlag GmbH, D-69451 Weinheim.

Malluche, H.H., et al., Management of hyperphosphataemia of chronic kidney disease: lessons from the past and future directions, Nephrol Dial Transplant, 2002, pp. 1170-1175, vol. 17, European Renal Association-European Dialysis and Transplant Association.

Rauter, H., et al., Selective Platination of Biologically Relevant Polyamines. Linear Coordinating Spermidine and Spermine as Amplifying Linkers in Dinuclear Platinum Complexes, Inorg. Chem., 1997, pp. 3919-3927, vol. 36, American Chemical Society.

Sugano, M., et al., A novel use of chitosan as a hypocholesterolemic agent in rats, The American Journal of Clinical Nutrition, 1980, pp. 787-793, vol. 33.

Barsotti, G. et al. 1979. Anion-Exchange Resins for the Uremic Hyperphosphatemia. *Mineral and Electrolyte Metabolism*. 2(1): 206.

Brezina, B. et al., "Acid loading during treatment with sevelamer hydrochloride: mechanisms and clinical implications". *Kidney International*, (2004), 66:S39-S45.

Buhleier, Egon et al. 1978. "Cascade"—and "Nonskid-Chain-like" Syntheses of Molecular Cavity Topologies. *Synthesis*. 1978(02): 155-158.

Burke, Steven K. 2000. Renagel®: reducing serum phophorus in haemodialysis patients. *Hospital Medicine*.61(9): 622-627.

Burt, Helen M. et al. 1985-86. In Vitro Studies Using Ion Exchange Resins as Potential Phosphate Binders for Renal Failure Patients. *Uremia Investigation*.9(1): 35-44.

Burt, Helen. M. et al. 1986. Ion-Exchange Resins as Potential Phosphate-Binding Agents for Renal Failure Patients: Effect of the Physicochemical Properties of Resins on Phosphate and Bile Salt Binding. *Journal of Pharmaceutical Sciences*. 76(5): 379-383.

Chertow, G.M. et al. "Long-term effects of sevelamer hydorchloride on the calcium x phosphate product and lipid profile of haemodialysis patients". *Nephrology Dialysis Transplantation*, (1999), 14: 2907-2914.

Cholestyramine. 1998. Cholestyramine for oral suspension. Copley Pharmaceutical, Inc. Canton, MA. (Package Insert).

Colestid®. 2003. Colestid® micronized colestipol hydrochloride tablets. Pharmacia & Upjohn Company, Kalamazoo, MI. (Package Insert).

Coli, L. et al. 1992. Phosphate Removal by Resin Hemoperfusion Efficacy and Biocompatibility of a New Exchange Resin. *Biomaterials, Artificial Cells, and Immobilization Biotechnology.* 20(5): 1153-1163.

Daniel, Marie-Christine, et al. 2003. Supramolecular H-Bonded Assemblies of Redox-Active Metallodendrimers and Positive and Unusual Dendritic Effects on the Recognition of H2PO4. *J. Am. Chem.. Soc.* 125(5): 1150-1151.

De Simone, Renato et al. 1978. New Microporous Cholestyramine Analog for Treatment of Hypercholesterolemia. *Journal of Pharmaceutical Sciences.* 67(12): 1695-1698.

Grynpas, R. et al. 1986. Organic ion exchange resins as substitutes for aluminum hydroxide gels. *Life Support Systems.*4(Suppl. 2): 276-8. (Abstract only).

Hagmaier, V. et al., "Test of efficacy of an oxalate-binding anion exchanger Colestid in healthy subjects for use in idiopathic calcium-oxalate urolithiasis". *Helvetica Chirurgica Acta,* (Aug. 1981), 48(3-4):421-424.

Hagmaier, V. et al. 1981. Investigation of the efficacy of oxalate-binding anionic exchanger Colestid in healthy subjects for use in idiopathic calcium-oxalate-urolithiasis. *Helv. Chir. Acta.* 48(3/4): 421-424.

Hardy, P. et al. 1998. Inhibition of Gastric Secretion by Omeprazole and Efficiency of Calcium Carbonate on the Control of Hyperphosphatemia in Patients on Chronic Hemodialysis. *Artificial Organs.* 22(7): 569-573.

Honda, Yoshiteru et al. 2000. Studies on Adsorption Characteristics of Bile Acids and Methotrexate to a New Type of Anion-Exchange Resin, Colestimide. *Chem. Pharm. Bull.* 48(7): 978-981.

Hurst, P.E. et al. 1963. The Effect of Oral Anion Exchange Resins on Fæcal Anions. Comparison with Calcium Salts and Aluminum Hydroxide. *Clin. Sci.* 24: 187-200.

Kioussis, Dimitri R., et al. 2005. Characterization of anion diffusion in polymer hydrogels used for wastewater remediation. *Polymer.* 46: 9342-9347.

Kioussis, Dimitri R., et al. 2005. Characterization of network morphology in anion binding hydrogels used for wastewater remediation. *Polymer.* 46: 10167-10172.

Klapper, M. et al., "Poly(methylene amine): A Polymer with the Maximum Possible Number of Amino Groups on a Polymer Backbone", *Angew. Chem. Int. Ed.,* vol. 42 (2003), pp. 4687-4690.

Konechnik. Thomas J. et al. 1989. In Vitro Adsorption of Bile Salts by Colestipol Hydrochloride. *Pharmaceutical Research.* 6(7): 619-623.

Kurihara, Satoshi et al. 2005. Effect of MCI-196 (colestilan) as a phosphate binder on hyperphosphataernia in haemodialysis patients: a double-blind, placebo-controlled, short-term trial. *Nephrol Dial Transplant.* 20(2): 424-430.

Mazzeo, Jeffrey R., et al. 1999. A phosphate binding assay for sevelamer hydrochloride by ion chromatography. *J. Pharm. Biomed. Anal.* 19: 911-915.

McGary, T.J. et al. 1984-85. Polycation as an Alternative Osmotic Agent and Phophate Binder in Peritoneal Dialysis. *Uremia Investigation.* 8(2): 79-84.

Nolan, James P. et al. 1975. Endotoxin Binding by Charged and Uncharged Resins. *Proceedings of the Society for Experimental Biology and Medicine.* 149: 766-770.

Panova, T.V., et al. 2004. Interaction of Poly(propylenimine) Dendrimers with Polyanionic Hydrogels. *Faculty of Chemistry, Moscow State University.* 46(5): 783-798. (in Russian with English Abstract).

Peppas, Nicholas A. et al. 1993. Dendrimers and Star Polymers for Pharmaceutical and Medical Applications. *Proceed. Intern. Symp. Control. Rel. Bioact. Mater.*20: 143-144.

Reiss, Guido J. et al. 2000. Protonation products of pentaaminopentane as novel building blocks for hydrogen-bonded networks. *Acta Crysta.* C56: 284-288.

Ross, E.A. et al., "Synthesis of molecularly imprinted polymers (MIPs) for phosphate binding". Published in the abstract list of Renal Week Conference (Sep. 20, 2004), ASN.

Schneider, H. et al. 1984. Aluminum-free oral phosphate binder. *Dep. Nephrol. Hypertension.* 1(2): 76-9. (Abstract Only).

Sechet, A. et al. 1999. Inhibition de la secretion gastrique par l'omeprazole et efficacite du carbonate de calcium sur le controle de l'hyperphosphoremie des patients hemodialyses chroniques [Inhibition of gastric secretion by omeprazole and efficacy of calcium carbonate in the control of hyperphosphatemia in patients on maintenance hemodialysis]. *Nephrologie.* 20(4): 213-216. (Article in French with English Summary).

Shataeva L.K. et al. 1982. [Effect of FAF anionite swelling on its sorption properties]. *Prikl Biokhim Microbiol.* 18(1): 65-70. (in Russian w/ English abstract).

Slatopolsky, E.A. et al., "RenaGel®, a nonabsorbed calcium-and aluminum-free phosphate binder, lowers serum phosphorus and parathyroid hormone", *Kidney International,* (1999), 55:299-307.

Swearingen, Ronald A. et al. 2002. Determination of the binding parameter constants of Renagel® capsules and tablets utilizing the Langmuir approximation at various pH by ion chromatography. *Journal of Pharmaceutical and Biomedical Analysis.* 29: 195-201.

Titu, Mari, et al. 2005. Aminic epoxy resin hardeners as reactive solvents for conjugated polymers; polyaniline base/epoxy composites for anticorrosion coatings. *Polymer.* 46: 6855-6861.

WelChol® Tablets. Licensed from: GelTex Pharmaceuticals, Inc. (Package Insert).

Wrong, O.M. 1972. Aluminum Toxicity. *Lancet.* 2(7772): 334-5.

Wrong, O.M. 1973. Anion-Exchange Resins in Treatment of Ur6524 mic Acidosis and Hyperphosphatæmia. *Lancet.*1(7801):493.

Zimmer, A. et al., "Ligand Synthesis and Metal Complex Formation of 1,2,3-Triaminopropane", *Eur. J. Inorg. Chem.,* Jul. 1998, pp. 2079-2086.

Zimmer, Anja et al. 2001. Complex Formation of $Ni^{II}$, $Cu^{II}$, and $Co^{III}$ with 1,2,3,4-Tetraaminobutane. *Chem. Eur. J.* 7(4): 917-931.

De Brabander-Van Den Berg, E.M.M., et al., "Poly(propylene imine) Dendrimers: Large-Scale Synthesis by Hetereogeneously Catalyzed Hydrogenations," Angew. Chem. Int. Ed. Engl., 1993, pp. 1308-1311, vol. 32, No. 9.

* cited by examiner

TREATMENT OF HYPERPHOSPHATEMIA
USING CROSSLINKED SMALL MOLECULE
AMINE POLYMERS

CROSS-REFERENCE

This application is a divisional application of Ser. No. 10/980,991 entitled ANION-BINDING POLYMERS AND USES THEROF filed Nov. 3, 2004, which is a continuation-in-part application of Ser. No. 10/806,495 entitled CROSSLINKED AMINE POLYMERS, filed Mar. 22, 2004 now U.S. Pat. No. 7,335,795; Ser. No. 10/701,385 entitled POLYAMINE POLYMERS, filed Nov. 3, 2003; and Ser. No. 10/965,044 entitled ANION-BINDING POLYMERS AND USES THEREOF, filed Oct. 13, 2004, which are incorporated herein by reference in their entirety and to which applications we claim priority under 35 USC § 120.

BACKGROUND OF THE INVENTION

Ion selective sorbents have been used in human therapy to correct disorders in electrolyte balance, in conditions such as hyperphosphatemia, hyperoxaluria, hypercalcemia, and hyperkalemia. Hyperphosphatemia occurs in patients with renal failure, whose kidneys no longer excrete enough phosphate ions to compensate exogenous phosphate uptake in the diet. This condition leads to high serum phosphate concentration and high calcium x phosphate product. Although the etiology is not fully demonstrated, high calcium x phosphate product has been held responsible for soft tissue calcification and cardiovascular disease. Cardiovascular disease is the cause of death in almost half of all dialysis patients.

Aluminum, calcium, and, more recently, lanthanum salts have been prescribed to control phosphate ion absorption in the gastrointestinal (GI) tract and restore systemic phosphate levels back to normal. However these salts liberate soluble aluminum and calcium cations in the GI tract, which are then partially absorbed into the blood stream. Aluminum absorption can cause serious side effects such as aluminum bone disease and dementia; high calcium uptake leads to hypercalcemia and puts patients at risk for coronary calcification.

Metal-free phosphate binders such as strong base ion-exchanger materials, Dowex and Cholestyramine resins, have been suggested for use as phosphate binders. However, their low capacity of binding requires high dosage that is not well tolerated by patients.

Amine functional polymers have been described as phosphate or oxalate binders. For example, see U.S. Pat. Nos. 5,985,938; 5,980,881; 6,180,094; 6,423,754; and PCT publication WO 95/05184. Renagel, a crosslinked polyallylamine resin, is a phosphate sequestering material introduced in the market as a metal-free phosphate binder. In vitro phosphate binding of Renagel is approximately 6 mmol/gm in water and 2.5 mmol/gm when measured in 100 mM sodium chloride and 20 mM phosphate at neutral pH. The recommended dosage for the targeted patient population is typically between 5 gms/day to 15 gms/day to keep the phosphate concentration below 6 mg/dL. Published phase I clinical trials on Renagel, performed on healthy volunteers, indicate that 15 gms of Renagel decrease the phosphate urinary excretion from a baseline of 25 mmole to 17 mmole, the difference being excreted in the feces as free and polymer-bound phosphate. From these data, the in vivo capacity range can be established at 0.5-1 mmol/gm, which is much less than the in vitro capacity of 6 mmol/gr measured in saline. Considering only the in vitro binding capacity of Renagel measured in saline, a dosage of 15 gm of phosphate binder would bind more than the entire phosphorous content of the average American diet, i.e. 37 mmol/day. The discrepancy between the in vitro binding capacity and the documented low in vivo binding capacity has a negative impact on the therapeutic benefit of the drug since more resin is needed to bring the serum phosphate to a safe range.

This loss of capacity of ion-exchange resins is not limited to Renagel when used in the complex environment of the GI tract environment. Although generally safe from a toxicological perspective, the large dose and inconvenience associated with taking multigram amounts of resin argues for the need to improve resin capacity. As an example, even in reported safety studies of the Renagel binder, patients have noted gastrointestinal discomfort at doses as low as 1.2-2.0 gm/day for an 8 week treatment period. Patients receiving 5.4 gm of Renagel/day were discontinued from treatment due to adverse events such as GI discomfort in 8.9% of the cases (Slatapolsky, et al Kidney Int. 55:299-307, 1999; Chertow, et al Nephrol Dial Transplant 14:2907-2914, 1999). Thus, an improvement in in vivo binding capacity that translates to lower, better tolerated dosing would be a welcome improvement in resin-based therapies.

As a result of these considerations there is still a great need for safe, high-capacity binders that selectively remove ions from the body with a lower drug dosage and a better patient compliance profile.

Patient compliance is recognized today as one of the main limiting factors for patients to comply with the K/DOQI recommendations: dose escalation implies that patients have to take ten 800 mg pills per day and beyond. Renagel pills take the form of swallowable tablets and are administered with a minimum of fluid, adding to the burden of ESRD patients who are under fluid restriction. More easy-to-take pharmaceutical formulation would be desirable: in particular chewable tablets are becoming more popular amongst the geriatric and pediatric population and in treatments requiring a large pill burden: chewable tablets allows greater strength pills and ultimately reduces the number of tablets per meal. Because the active contained in a chewable tablet is first dispersed under the effects of mastication and saliva before being swallowed, the requirements on both the shape and weight of the tablet are much less severe than those imposed on swallowable tablets: However, until now it was not possible to formulate a hydrogel such as Renagel in a chewable tablet because of the high swelling characteristics of that polymer: Renagel usually swells very rapidly up to about 10 times its weight in an isotonic solution. This has two much undesired consequences: firstly, while in the mouth the polymer will swell and give a very unpleasant feel (dry mouth, sensation of choking); secondly, even if patient overcomes the sensory in mouth, the administration of a swollen gel in the esophagus can be hazardous. Besides, it is also well known that highly swellable gels, when administered in the multi grams range, provoke side effects such as bloating, constipation or diarrhea.

SUMMARY OF THE INVENTION

In one aspect, the invention provides anion-binding polymers. In some embodiments, the invention provides an anion-binding polymer where the polymer binds a target anion (e.g., phosphate or oxalate), and where the polymer is characterized by at least two of the following features: a) a swelling ratio of less than about 5; b) a gel pore volume distribution measured in a physiological medium characterized by a fraction of said pore volume accessible to non-interacting solutes, of molecular weight greater than about twice the MW of the target anion, of less than about 20% of the weight of the gel; and c)

an ion-binding interference for the target anion lower than about 60% when measured in a gastrointestinal simulant, relative to a non-interfering buffer. In some embodiments, the swelling ratio is less than about 4, or less than about 3, or less than about 2.8, or less than about 2.7, or less than about 2.6, or or less than about 2.5. In some embodiments, the polymer binds bile acids or citrate with a capacity of less than about 2 mmol/gm, or less than about 1 mmol/gm, or less than about 0.5 mmol/gm, or less than about 0.3 mm/gm, or less than about 0.1 mm/gm. In some embodiments, the swelling ratio is measured in isotonic solution and neutral pH. In some embodiments, the polymer comprises amine monomers. In some embodiments, the amine monomers are selected from the group consisting of allylamine, vinylamine, ethyleneimine, 1,3 diamino propane, and N,N,N',N'-tetrakis(3-aminopropyl)1,4 diaminobutane, 1,2,3,4 tetraaminobutane, Formula 1 and Formula 2, where Formula 1 and Formula 2 are the following structures:

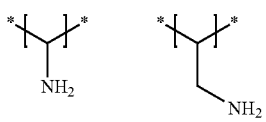

In some embodiments, the invention provides an anion-binding polymer containing crosslinked polyamines, where the polymer is obtained by inverse suspension, and wherein the swelling ratio of the polymer is less than 5.

In some embodiments, the invention provides a phosphate-binding polymer where the polymer is characterized by at least one of the following features: a) a swelling ratio of less than about 5, preferably less than about 2.5; b) a gel pore volume distribution measured in a physiological medium characterized by a fraction of said pore volume accessible to non-interacting solutes, of molecular weight greater than about 200, of less than about 20% of the weight of the gel; and c) an ion-binding interference for phosphate lower than about 60% when measured in a gastrointestinal simulant, relative to a non-interfering buffer. In some embodiments, the swelling ratio is less than about 2.8, or less than about 2.7, or less than about 2.6. In some embodiments, the polymer binds bile acids or citrate with a capacity of less than about 2 mmol/gm, or less than about 1 mmol/gm, or less than about 0.5 mmol/gm, or less than about 0.3 mm/gm, or less than about 0.1 mm/gm. In some embodiments, the swelling ratio is measured in isotonic solution and neutral pH.

In some embodiments, the invention provides a phosphate-binding polymer where the polymer is characterized by a swelling ratio of less than about 5, preferably less than about 2.8, or less than about 2.7, or less than about 2.6, most preferably less than about 2.5, where this ratio is measured in isotonic solution and neutral pH. In embodiments, the polymer has a mean in vivo phosphate binding capacity of greater than about 0.5 mole/gm. In embodiments, the polymer is a polyamine polymer, and the chloride content of the polymer is less than about 35 mol % of the content of amine groups.

In some embodiments, the invention provides an anion-binding polymer where the polymer binds a target anion (e.g., phosphate or oxalate), and where the polymer is characterized by at least two of the following features: a) a swelling ratio of less than about 5; b) a gel pore volume distribution measured in a physiological medium characterized by a fraction of said pore volume accessible to non-interacting solutes, of molecular weight greater than about twice the MW of the target anion, of less than about 20% of the weight of the gel; and c) an ion-binding interference for the target anion lower than about 60% when measured in a gastrointestinal simulant, relative to a non-interfering buffer, where the polymer contains one or more amine monomers and one or more crosslinkers, and where the polymer is produced by a process in which the amine is present in solvent before crosslinking at a ratio of amine:solvent of from about 3:1 to about 1:3 and the total content crosslinkers added to the reaction mix is such that the average number of connections to the amine monomers (NC) is between about 2.05 and about 6, or between about 2.2 and about 4.5. In some embodiments, the polymer is further produced by a process where the target anion is present during the crosslinking reaction, for example by: a) adding the amine monomer as a free base and adding the target anion in its acid form; b) adding a crosslinker; c) carrying out the crosslinking reaction; and d) washing out the target ion.

In some embodiments, the invention provides an anion-binding polymer where the polymer binds a target anion (e.g., phosphate or oxalate), and where the polymer is characterized by at least two of the following features: a) a swelling ratio of less than about 5; b) a gel pore volume distribution measured in a physiological medium characterized by a fraction of said pore volume accessible to non-interacting solutes, of molecular weight greater than about twice the MW of the target anion, of less than about 20% of the weight of the gel; and c) an ion-binding interference for the target anion lower than about 60% when measured in a gastrointestinal simulant, relative to a non-interfering buffer, where the polymer contains one or more amine monomers and one or more crosslinkers, and where the polymer is produced by a process including: a) forming soluble prepolymer by adding the entire amine monomer component and then continuously adding continuously a fraction of the crosslinker to forming a syrup; b) emulsifying the syrup in oil; and c) adding the remaining fraction of crosslinker to form crosslinked beads.

In some embodiments, the invention provides an anion-binding polymer where the polymer binds a target anion (e.g., phosphate or oxalate), and where the polymer is characterized by at least two of the following features: a) a swelling ratio of less than about 5; b) a gel pore volume distribution measured in a physiological medium characterized by a fraction of said pore volume accessible to non-interacting solutes, of molecular weight greater than about twice the MW of the target anion, of less than about 20% of the weight of the gel; and c) an ion-binding interference for the target anion lower than about 60% when measured in a gastrointestinal simulant, relative to a non-interfering buffer, where the polymer contains one or more amine monomers and one or more crosslinkers, and where the polymer is produced by a process including: a) carrying out a first reaction between an amine monomer and a crosslinker to form a gel; then b) reacting the gel with an aminoalkylhalide, where the amine alkyl groups are chemically attached to the gel through halide substitution by the amine functional gels.

In some embodiments, the invention provides a phosphate-binding polymer containing one or more amine monomers and one or more crosslinkers where the polymer is produced by a process where the total content of crosslinkers added to the reaction mix is such that the average number of connections to the amine monomers is between 2.2 and 4.5.

In some of these embodiments, the amine monomer is selected from the group consisting of 1,3 diamino propane, and N,N,N',N'-tetrakis(3-aminopropyl)1,4 diaminobutane, and wherein the crosslinker is selected from the group consisting of 1,3 dichloropropane and epichlorohydrin. In embodiments, the invention provides an ion-binding polymer comprising N,N,N',N'-tetrakis(3-aminopropyl)1,4 diaminobutane crosslinked by epichlorohydrin wherein the polymer is produced by a process wherein the ratio of the initial concentration of N,N' tetrakis(3-aminopropyl 1,4 diaminobutane to water is about 1:3 to about 4:1, or about 1.5:1 to about 4:1.

In some embodiments, the invention provides a phosphate-binding polymer containing N,N,N',N'-tetrakis(3-aminopropyl)1,4 diaminobutane monomers and epichlorohydrin crosslinker, wherein the polymer is produced by a process in which the total epichlorohydrin crosslinker added to the reaction mix is about 200% to about 300 mol %, or about 230 to about 270 mol %, or about 250 mol % of the total N,N,N',N'-tetrakis(3-aminopropyl)1,4 diaminobutane content. In some of these embodiments, the polymer is produced by a process in which the ratio of monomers to water in the initial reaction mix is about 3:1 to about 1:1, or about 1.73. In some embodiments, the polymer is in the form of spherical beads.

In some embodiments, the invention provides a phosphate-binding polymer comprising polyallylamine monomers and epichlorohydrin crosslinker, wherein the polymer is produced by initially dissolving the polyallylamine monomers in water at a monomer:water ratio of about 3:1 to about 1:3. In some of these embodiments, the total epichlorohydrin crosslinker added to the reaction mix is about 10 mol % of the total polyallylamine content.

In some embodiments, the invention provides a phosphate-binding polymer comprising a prepolymer comprising 1,3 diamino propane and 1,3 dichloropropane crosslinker in a 1:1 molar ratio, wherein the prepolymer is further crosslinked by epichlorohydrin crosslinker, and wherein the total epichlorohydrin crosslinker added to the reaction mix is about 200 mol % of the total prepolymer, and wherein the prepolymer:water ratio in the reaction mix is about 1.1:1 to about 1.7:1.

The invention further provides compositions containing any of the above polymers where the polymer is in the form of particles, and where the polymeric particles are encased in an outer shell.

In another aspect, the invention provides pharmaceutical compositions. In one embodiment, the pharmaceutical composition contains a polymer of the invention and a pharmaceutically acceptable excipient. In some embodiments, the composition is a liquid formulation in which the polymer is dispersed in a liquid vehicle of water and suitable excipients. In some embodiments, the invention provides a pharmaceutical composition comprising an anion-binding polymer that binds a target anion, and one or more suitable pharmaceutical excipients, where the composition is in the form of a chewable or mouth-disintegrating tablet, and where the polymer has a swelling ratio while transiting the oral cavity and in the esophagus of less than about 5, or less than about 2.8, or less than about 2.7, or less than about 2.6, or preferably less than about 2.5. In some embodiments the chewable tablet contains polymer where the polymer has a transition temperature greater than about 50° C.

In some embodiments the chewable tablet contains a pharmaceutical excipient selected from the group consisting of sucrose, mannitol, xylitol, maltodextrin, fructose, sorbitol, and combinations thereof, and is produced by a process where the polymer is pre-formulated with the excipient to form a solid solution. In some embodiments the target anion of the polymer is phosphate. In some embodiments the polymer binds a target ion in vivo with a binding capacity of greater than 0.5 mmol/gr. In some embodiments the anion-binding polymer is more than about 50% of the weight of the tablet. In some embodiments, the tablet is of cylindrical shape with a diameter of about 22 mm and a height of about 4 mm and the anion binding polymer comprises more than about 1.6 gm of the total weight of the tablet. In some of the chewable tablets of the invention, the excipients are chosen from the group consisting of sweetening agents, binders, lubricants, and disintegrants. Optionally, the polymer is present as particles of less than about 40 um mean diameter. In some of these embodiments, the sweetening agent is selected from the group consisting of sucrose, mannitol, xylitol, maltodextrin, fructose, and sorbitol, and combinations thereof.

In a further aspect, the invention provides a method of measuring target ion binding interference for an ion-binding polymer that binds a target ion by: a) adding the ion binding polymer to a non-interfering buffer containing the target ion and measuring the target ion binding capacity of the polymer; b) artificially digesting a standardized meal with mammalian GI enzymes and/or aspirating chyme from the upper gastrointestinal tract of mammals having taken said standardized meal; wherein the standardized meal contains the target ion; c) adding the ion binding polymer and measuring the target ion binding capacity from the target ion concentration decrease before and after the addition of target ion; and d) calculating the degree of interference in binding as the fractional decrease in binding capacity for the target ion, expressed as a percent, observed between the binding measurement in a non interfering buffer, and in the digested meal or ex-vivo aspirates, at the same ion concentration in equilibrium.

In yet a further aspect, the invention provides a method of selecting an ion-binding polymer, said polymer comprising monomer and crosslinker, wherein said polymer possesses at least one of the features: a) a swelling ratio of less than about 5; b) a gel pore volume distribution measured in a physiological medium characterized by a fraction of said pore volume accessible to non-interacting solutes, of molecular weight greater than about twice the MW of the target anion, of less than about 20% of the weight of the gel; and c) an ion-binding interference for the target anion lower than about 60% when measured in a gastrointestinal simulant, relative to a non-interfering buffer that includes the steps of: i) varying the following composition and process variables: 1) the ratio of crosslinker to monomer; 2) the ratio of (monomer+crosslinker) to solvent in the reaction medium; 3) the net charge of the polymer at physiological pH and tonicity; and/or 4) the hydrophilic/hydrophobic balance of the backbone polymer; ii) evaluating the swellability, porosity, and ion binding interference of the resulting polymer; and iii) selecting a polymer that possesses at least one of said features. In another aspect, the invention provides a method for improving the therapeutic properties and/or suitability for administration and/or pharmaceutical properties of a polyamine polymer comprising at least one of the following steps: a) crosslinking said polymer with a crosslinker, such that the average number of connection to the polyamine monomer is between about 2.05 and about 6; and/or b) producing said polymer by a process wherein the polyamine is initially present in water at a ratio of polyamine:water of from about 3:1 to about 1:3.

In another aspect, the invention provides a method of making an anion-binding polymer that binds a target anion, comprising combining an amine monomer with a crosslinker by a heterogeneous process, wherein the phosphate-binding polymer is characterized by at least two of the following features: a) a swelling ratio of less than about 5; b) less than about 20% of the weight of the polymer accessible to non-interacting solutes of molecular weight greater than about twice the MW of the target anion, wherein said percentage is measured in a physiological medium, and c) an ion-binding interference for the target anion lower than about 60% when measured in a gastrointestinal simulant, relative to a non-interfering buffer. In some embodiments the amine monomer is a polyallylamine. In some embodiments the crosslinker is epichlorohydrin.

In another aspect the invention provides an anion-binding polymer that binds a target ion, wherein the polymer is produced by a process comprising crosslinking a polyallylamine by a heterogeneous process, and wherein said polymer is characterized by at least two of the following features: a) a swelling ratio of less than about 5; b) less than about 20% of the weight of the polymer accessible to non-interacting solutes of molecular weight greater than about twice the MW of the target anion, wherein said percentage is measured in a physiological medium, and c) an ion-binding interference for the target anion lower than about 60% when measured in a gastrointestinal simulant, relative to a non-interfering buffer. In one embodiment, the polyallyamine is crosslinked by epichlorohydrin.

In another aspect, the invention provides a method of removing an anion from an animal by administering an effective amount of a polymer of the invention to the animal. In some embodiments, the polymer is an anion-binding polymer where the polymer binds a target anion (e.g., phosphate or oxalate), and where the polymer is characterized by at least two of the following features: a) a swelling ratio of less than about 5; b) a gel pore volume distribution measured in a physiological medium characterized by a fraction of said pore volume accessible to non-interacting solutes, of molecular weight greater than about twice the MW of the target anion, of less than about 20% of the weight of the gel; and c) an ion-binding interference for the target anion lower than about 60% when measured in a gastrointestinal simulant, relative to a non-interfering buffer. In some embodiments, the target anion of the polymer is phosphate; in some embodiments the phosphate is removed from the gastrointestinal tract; in some embodiments the method of administration is oral. In some embodiments, the animal is afflicted with at least one disease selected from the group consisting of hyperphosphatemia, hypocalcemia, hyperthyroidism, depressed renal synthesis of calcitriol, tetany due to hypocalcemia, renal insufficiency, ectopic calcification in soft tissues, and ESRD. In some embodiments, the animal is a human.

In some embodiments, the polymer is co-administered with at least one of proton pump inhibitor, calcimimetic, vitamin and analogs thereof, or phosphate binder, e.g., a phosphate binder that is aluminum carbonate, calcium carbonate, calcium acetate, lanthanum carbonate, or SEVELAMER hydrochloride.

INCORPORATION BY REFERENCE

All publications and patent applications mentioned in this specification are herein incorporated by reference to the same extent as if each individual publication or patent application was specifically and individually indicated to be incorporated by reference.

Figure 1:
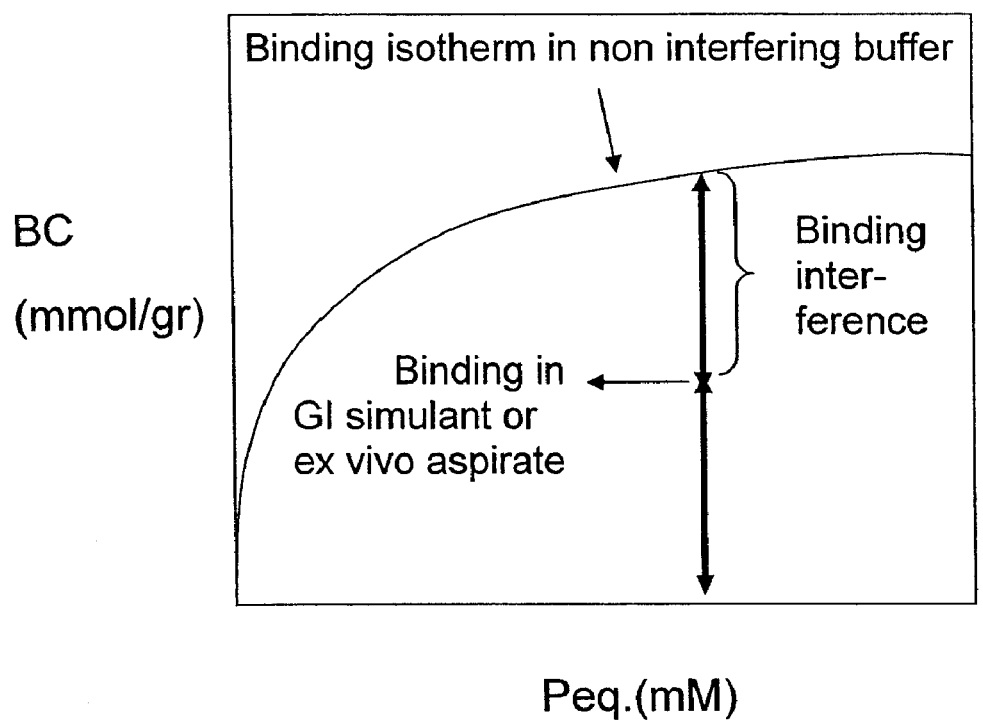
FIG. 1 is a graph illustrating the determination of binding interference by comparing an isotherm of binding of target ion by a polymer in a non-interfering buffer to binding of target ion by the polymer in an interfering medium (e.g., gastrointestinal simulant or ex vivo aspirate).

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

I. Introduction

One aspect of the invention provides anion binding polymeric materials that have one or more of the characteristics of low swelling, high ion binding in vivo, low interference from interfering ions, and/or specific porosity. Another aspect of the invention provides pharmaceutical compositions of the anion-binding polymers, where the pharmaceutical composition is a chewable tablet or a liquid formulation. A further aspect of the invention provides methods of making or improving anion-binding polymers so that they have one or more of the characteristics of low swelling, high ion binding in vivo, low interference from interfering ions, and/or specific porosity. A yet further aspect of the invention is methods of using the anion-binding polymers of the invention to treat conditions in which an ion is in excess. In a preferred embodiment, the anion-binding polymers are used to remove target anions from the GI tract. Examples of target anions that can be removed from the GI tract include, but are not limited to, phosphate and oxalate. In another preferred embodiment, the compositions described herein are used in the treatment of hyperphosphatemia, hypocalcemia, hyperparathyroidism, depressed renal synthesis of calcitriol, tetany due to hypocalcemia, renal insufficiency, ecotopic calcification in soft tissues, chronic renal insufficiency, and anabolic metabolism.

II. Polymers

The polymers of the invention are characterized by their ability to bind ions. Preferably the polymers of the invention bind anions, more preferably they bind phosphate and/or oxalate, and most preferably they bind phosphate ions. For illustration, anion-binding polymers and especially phosphate-binding polymers will be described; however, it is understood that this description applies equally, with appropriate modifications that will be apparent to those of skill in the art, to all ions and solutes. As used herein, a polymer "binds" an ion, e.g. an anion, or is an "ion-binding" polymer (e.g., a "phosphate-binding" polymer) when it associates with the ion, generally though not necessarily in a noncovalent manner, with sufficient association strength that at least a portion of the ion remains bound under the in vitro or in vivo conditions in which the polymer is used for sufficient time to effect a removal of the ion from solution or from the body. A "target ion" is an ion to which the polymer binds, and usually refers to the major ion bound by the polymer, or the ion whose binding to the polymer is thought to produce the therapeutic effect of the polymer. A polymer may have more than one target ion. "Binding" of an anion, is more than minimal binding, i.e., at least about 0.01 mmole of anion/gm of polymer, more preferably at least about 0.05 mmole of anion/gm of polymer, even more preferably at least about 0.1 mmole of anion/gm of polymer, and most preferably at least about 0.5 mmole of anion/gm of polymer. The invention provides polymers that are characterized by their selective binding of anions; for example, in some embodiments, polymers of the invention bind bile acids with a binding capacity of less than about 2 mmol/gm, preferably less than about 1 mmol/gm, more preferably less than about 0.5 mmol/gm, even more preferably less than about 0.3 mmol/gm, and most preferably less than about 0.1 mmol/gm. In some embodiments, polymers of the invention bind citrate with a binding capacity of less than about 2 mmol/gm, preferably less than about 1 mmol/gm, more preferably less than about 0.5 mmol/gm, even more preferably less than about 0.3 mmol/gm, and most preferably less than about 0.1 mmol/gm.

A. Characteristics

The polymers of the invention are characterized by one or more of the following features: 1) low swelling ratio; 2) low binding interference under physiological conditions; 3) a porosity appropriate to bind the target anion, and to exclude interfering solutes; 4) an in vivo binding capacity for the target anion, sufficient to be effective in therapeutic uses. In some embodiments, the polymer is an anion-binding polymer (e.g., a polymer that binds phosphate and/or oxalate), where the polymer is characterized by at least two of the following features: 1) a swelling ratio of less than about 5; 2) a gel pore volume distribution measured in a physiological medium characterized by less than about 20% of said pore volume accessible to non-interacting water soluble solutes of molecular weight greater than about twice the MW of the target anion; and 3) an ion-binding interference for the target anion of said polymer lower than about 60% when measured in a gastrointestinal simulant, relative to a non-interfering buffer. In some embodiments, the polymer is a phosphate-binding polymer characterized by at least one of the following features: 1) a swelling ratio of less than about 5, preferably less than about 2.5; 2) a gel pore volume distribution measured in a physiological medium characterized by less than about 20% of said pore volume accessible to non-interacting solutes of molecular weight greater than about 200; and 3) an ion-binding interference for phosphate lower than about 60% when measured in a gastrointestinal simulant, relative to a non-interfering buffer. In some embodiments, the phosphate-binding polymer has a swelling ratio of less than about 2.8, or less than about 2.7, or less than about 2.6. A "physiological medium" is a medium that is isotonic and at neutral pH. In some embodiments the invention provides a phosphate-binding polymer characterized by a swelling ratio, measured in isotonic medium at neutral pH, of less than about 5, preferably less than about 2.5, optionally with a mean in vivo binding capacity for phosphate of greater than about 0.5 mole/gm. In some embodiments, the phosphate-binding polymer has a swelling ratio of less than about 2.8, or less than about 2.7, or less than about 2.6. In some embodiments, polymers of the invention bind bile acids with a binding capacity of less than about 2 mmol/gm, preferably less than about 1 mmol/gm, more preferably less than about 0.5 mmol/gm, even more preferably less than about 0.3 mmol/gm, and most preferably less than about 0.1 mmol/gm. In some embodiments, polymers of the invention bind citrate with a binding capacity of less than about 2 mmol/gm, preferably less than about 1 mmol/gm, more preferably less than about 0.5 mmol/gm, even more preferably less than about 0.3 mmol/gm, and most preferably less than about 0.1 mmol/gm. Preferably, the polymers are composed of amine monomers.

Generally, these features are achieved by manipulating one or more factors in the production of the polymer.

1) Swelling ratio. Polymers of the invention are crosslinked materials, meaning that they do not dissolve in solvents, and, at most, swell in solvents.

The ratio of swelling in physiological isotonic buffer, representative of the milieu of use, i.e. the gastrointestinal tract, is typically in the range of about 1.2 to about 100, preferably about 2 to 20. In some embodiments, polymers of the invention have a swelling ratio of less than 5, or less than about 4, or less than about 3, or less than about 2.8, or less than about 2.7, or less than about 2.6, or less than about 2.5. As used herein, "swelling ratio" refers to the number of grams of solvent taken up by one gram of dried crosslinked polymer, when equilibrated in an aqueous environment. When more than one measurement of swelling is taken for a given polymer, the mean of the measurements is taken to be the swelling ratio.

Swelling ratios are measurable using a variety of methods: the most preferred is the gravimetric method, in which the dried polymer is weighed and added to an excess of liquid. In some cases the liquid may be distilled water; preferably the liquid is an aqueous solution that is isotonic to plasma; most preferably the liquid is an aqueous solution that is isotonic to plasma and that is buffered to a neutral pH. For example, 0.9% NaCl solution may be used. Phosphate buffered saline (PBS) may also be used. The most preferred physiological medium for swelling measurements is 0.9% NaCl buffered with 30 mM MES to a pH of between about 6.5 and 7.5. The dry polymer (e.g., a phosphate binding plymer) generally is used in filly protonated form with counterion, e.g., chloride. The polymer is soaked in the liquid until equilibration. The soaked gel is then centrifuged, the supernatant decanted, and the wet gel weighed. Care should be taken not to centrifuge to too high g number to avoid gel collapse. The swelling ratio (SR) is calculated as the weight of wet gel minus the weight of dry polymer, divided by the weight of dry polymer.

Another method is the dye method, in which a dye of very high molecular weight and known not to interact with the gel is prepared as an aqueous solution and an aliquot of dry polymer is added to the solution. The weight to weight ratio of solution to polymer is adjusted to be close and slightly higher than the expected swelling ratio. As the dye is of very high molecular weight (e.g. greater than 200,000 g/mol), it does not permeate the gel while the water does, leading to an increase in the resulting dye concentration, from which the swelling ratio is determined. An example of useful dye is dextran modified with fluoresceine isothiocyanate (FITC).

The swelling ratio of a polymer depends on a number of variables such as temperature, ionic strength, polymer charge density, polymer-solvent Flory-Huggins coefficient and crosslinking density. Because the ion-binding polymers of the invention are mostly charged polymers (e.g. phosphate ion binding polyamine are protonated at intestinal pH), their swelling behavior is typical of polyelectrolyte gels. Although swelling ratio and pore size are somewhat related, i.e. large swelling ratio is usually accompanied by large pores, there is no theoretical basis to accurately predict the exclusion limit of polyelectrolyte gels.

2) Binding interference. In some embodiments, polymers of the invention have a binding interference of less than about 70%, more preferably less than about 60%, even more preferably less than about 50%, more preferably less than about 40%, even more preferably less than about 30%, and most preferably less than about 20%, when measured in a gastrointestinal (GI) simulant. Phosphate-binding polymers of the invention exhibit a binding interference of less than about 70%, more preferably less than about 60%, even more preferably less than about 50%, more preferably less than about 40%, even more preferably less than about 30%, and most preferably less than about 20%, when measured in a GI simulant.

The "degree of interference in binding" or "binding interference," as used herein, refers to the fractional decrease in binding capacity for the target ion, expressed as a percent, observed between a binding experiment in a non interfering buffer, and in a gastrointestinal (GI) simulant, at the same concentration of target anion in equilibrium. A "non-interfering buffer," as used herein, refers to a buffer that does not contain one or more solutes that interfere with the binding of the target ion, and that is buffered to the same pH as the GI simulant. A non-interfering buffer is not necessarily free of all interfering solutes, for example a non-interfering buffer may contain one or both of the ubiquitous gastrointestinal ions chloride and bicarbonate; if present, these may be at their physiological concentration. An example of a non-interfering buffer is given in Example 1. A "GI simulant" refers herein to a preparation that is designed to mimic the milieu of a portion of the GI tract after ingestion of a meal, preferably the portion of the GI tract in which the polymer will be binding the majority of target ion. The GI simulant typically is prepared by the method illustrated in Example 1. Target ion should be present in the GI simulant at the same concentration(s) as used in non-interfering buffer studies. The degree of interference is easily illustrated by plotting the two corresponding binding isotherms, i.e. GI simulant and in a non-interfering buffer, as shown in FIG. 1. An example of determination of binding interference using a GI simulant is given in Example 1.

It is also possible to measure binding interference by comparing binding of target ion in digestive aspirate from subjects, preferably human subjects, to binding of target ion in non-interfering buffer. If this measurement is done, aspirates should be obtained from a number of subjects and the mean interference taken as the binding interference.

It has been found that by carefully selecting the swelling ratio and/or adjusting the molecular weight exclusion limit of the gel, the binding capacity measured in a competitive mode (i.e. in vivo or in a GI stimulant) can be substantially increased compared with other gels with the same polymer composition but otherwise non-optimized in gel porosity.

Strikingly, polymers in which crosslinking and/or entanglement were increased were found to have lower swelling than those with lower crosslinking and/or entanglement, yet also had a binding capacity for target ion (e.g., phosphate) that was as great as or greater than the lower crosslinking and/or entanglement polymers. Not wishing to be bound by theory, it is hypothesized that polymers of the invention exert a sieving effect and bind only solutes of a specific size in solution and exclude other larger species that would otherwise compete with binding sites within the polymer. Larger molecular weight species include but are not limited to, inorganic and organic anions, oligopeptides, carbohydrates, bilirubins, lipid micelles and lipid vesicles.

3) Porosity. It has been found that it is possible to manipulate the process for producing a polymer so that the polymer more optimally exhibits a porosity appropriate to bind the target ion (e.g., anions) for which the polymer is intended and to exclude interfering substances.

Pore size distribution of polymeric gels is obtained by various methods such as mercury porosimetry, nitrogen adsorption, differential scanning calorimetry, or solute permeation partitioning techniques. The latter technique, solute permeation partitioning technique, is most preferred as it probes the gel in a fully hydrated state identical to one prevailing in the milieu of use. The solute permeation technique is an indirect method introduced by Kuga (Kuga S. J, *J. of Chromatography*, 1986, 206:449-461) and consists of measuring the gel partitioning of solutes of known molecular weights. This method consists of three major steps (Kremer et al., Macromolecules, 1994, 27, 2965-73):

1. Solutions with dissolved solutes of known concentrations and molecular sizes are brought into contact with the swollen gel. The molecular sizes of the solutes must cover a substantial range.
2. Diffusion of solutes into the gel is attained. Partitioning of a particular solute depends on both the size of the solute and the size distribution of the gel pores.
3. The gel is separated from its surrounding solution, and subsequent concentration measurement of solutes in the surrounding solution are made. The decrease of each solute concentration relative to its initial stock solute concentration is used for calculating the gel pore size distribution.

To isolate the size exclusion effects from molecular attraction/repulsion effects, the solutes are selected from polymers or oligomers that have little or no interactions with the gel polymer; neutral hydrophilic polymers with narrow molecular weight distribution such as polyethyleneglycol, polyethylene oxide or dextran, are most suitable. Thus, unless otherwise indicated herein, volumes for exclusion of particular sizes of solutes (also referred to herein as "critical permeation volume") refer to volumes measured using solutes with substantially no interaction with the polymer for which measurements are taken.

Figure 2:
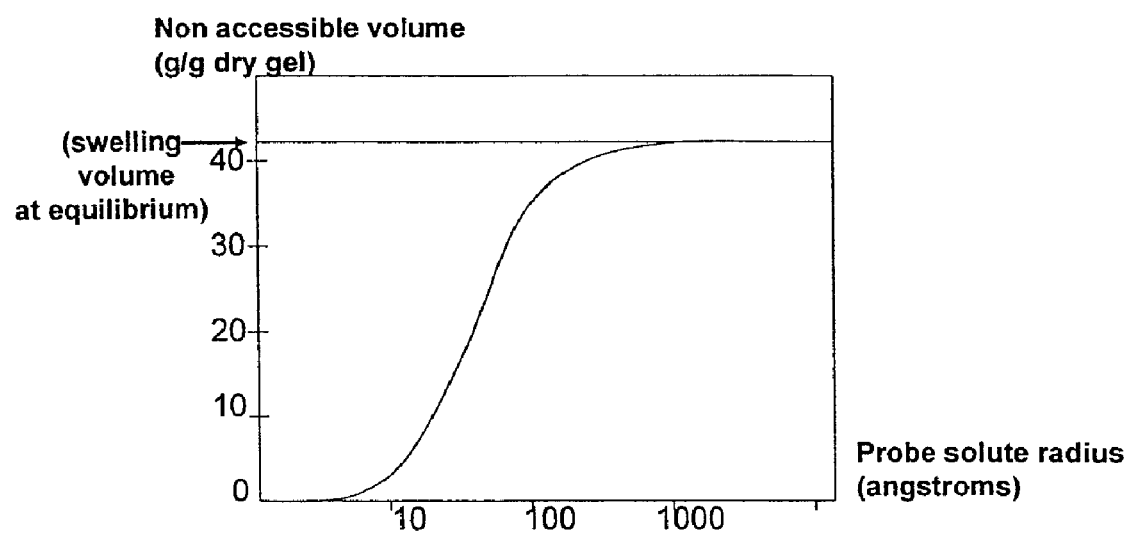
FIG. 2 is a graph illustrating non-accessible volume of gel versus probe solute radius.

Following the experimental protocol and data treatment given in Kremer et al., Macromolecules, 1994, 27, 2965-73, the pore size distribution may be represented as shown in FIG. 2. In FIG. 2, the Y axis represents the volume of the swollen gel not accessible to a solute of a given molecular size. In the example shown in the Figure, small molecules with a size smaller than 5 angstroms can permeate throughout the entire gel. At the other extreme, polymers with a hydrodynamic radius greater than 1000 angstroms are totally excluded from the gel. In that case the non accessible volume and the volume of gel at equilibrium are the same.

Size and molecular weight of polymers are related through Mark-Houvink equations which are tabulated for the polymer solutes used as molecular probes. For example:

Radius (angstroms)=$0.217 M^{0.498}$ Dextran
Radius (angstroms)=$0.271 M^{0.517}$ Polyethyleneglycol
Radius (angstroms)=$0.166 M^{0.573}$ Polyethyleneoxide Small molecular weight probes can also be used:
Urea: Molecular radius 2.5 angstroms
Ethylene glycol: Molecular radius 2.8 angstroms
Glycerol: Molecular radius 3.1 angstroms
Glucose: Molecular radius 4.4 angstroms
Saccharose: Molecular radius 5.3 angstroms Thus, the size for the solute may be converted to molecular weight and vice-versa.

The size of the solute does not equate the size of the pores; otherwise this would mean that all the liquid existing in pores greater than the molecular size of the solute is available as accessible volume: this is incorrect because of the excluded volume effect, also known as the wall effect.

A straightforward manner to characterize the molecular exclusion limit is: (i) quantify the partitioning of molecular probes, (ii) calculate the accessible volume (or weight) as described above and (iii) normalize it to the total gel volume (or weight).

The desired molecular exclusion limit is achieved by manipulation of production variables such as entanglement of polymer strands and concentration of crosslinker (see below). In general, polymers are produced to have a molecular exclusion limit that is based on the ion (e.g., anion) to be bound and the probable identity of the interfering substances that are wished to be excluded, as well as the tolerable amount of swelling for the intended use of the polymer. In some embodiments of the invention, the ion binding polymer displays a gel pore volume distribution (critical permeation volume) defined according to the protocol described above and measured in a physiological medium of less than about 60%, less than about 40%, or less than about 20% of the polymer pore volume accessible to non-interacting solutes of molecular weight greater than about twice the MW of the target anion. In some embodiments of the invention, the ion binding polymer displays a gel pore volume distribution (critical permeation volume) of less than about 60%, less than about 40%, or less than about 20% of the polymer pore volume accessible to non-interacting solutes of molecular weight greater than about 1.8-fold the MW of the target ion. In some embodiments of the invention, the ion binding polymer displays a gel pore volume distribution (critical permeation volume) of less than about 60%, less than about 40%, or less than about 20% of the polymer pore volume accessible to non-interacting solutes of molecular weight greater than about 1.6-fold the MW of the target ion. In some embodiments of the invention, the ion binding polymer displays a gel pore volume distribution (critical permeation volume) of less than about 60%, less than about 40%, or less than about 20% of the polymer pore volume accessible to non-interacting solutes of molecular weight greater than about 1.4-fold the MW of the target ion. In some embodiments of the invention, the ion binding polymer displays a gel pore volume distribution (critical permeation volume) of less than about 60%, less than about 40%, or less than about 20% of the polymer pore volume accessible to non-interacting solutes of molecular weight greater than about 1.2-fold the MW of the target ion. In embodiments the invention provides a phosphate-binding polymer displaying a gel pore volume distribution (critical permeation volume) defined according to the protocol described above and measured in a physiological medium of less than about 60%, less than about 40%, or less than about 20% of the polymer pore volume accessible to non-interacting solutes of molecular weight greater than about 200, more preferably greater than about 180, more preferably greater than about 160, more preferably greater than about 140, and most preferably greater than about 120.

4) Binding capacity. The polymers described herein exhibit ion binding properties, generally anion-binding properties. In preferred embodiments, the polymers exhibit phosphate binding properties. Ion (e.g., phosphate) binding capacity is a measure of the amount of a particular ion an ion binder can bind in a given solution. For example, binding capacities of ion-binding polymers can be measured in vitro, e.g., in water or in saline solution, or in vivo, e.g., from ion (e.g., phosphate) urinary excretion, or ex vivo, for example using aspirate liquids, e.g., chyme obtained from lab animals, patients or volunteers. Measurements can be made in a solution containing only the target ion, or at least no other competing solutes that compete with target ions for binding to the polymer. In these cases, a non interfering buffer would be used. Alternatively, measurements can be made in the presence of other competing solutes, e.g., other ions or metabolites, that compete with target ions for binding to the resin.

Ion binding capacity for a polymer can be calculated as $V*(C_{start}-C_{eq})/P$, expressed in mmol/gr, where V is the fixed volume of the solution used, in L; $C_{start}$ is the initial target ion concentration of the solution in mM; $C_{eq}$ is the equilibrium target ion concentration in the solution in mM, after a weight P, in grams, of polymer is added and equilibration allowed.

In some embodiments the polymer binds phosphate. For in vivo use, e.g., in treating hyperphosphatemia, it is desirable that the polymer have a high phosphate binding capacity. In vitro measurements of binding capacity do not necessarily translate into in vivo binding capacities. Hence, it is useful to define binding capacity in terms of both in vitro and in vivo capacity.

The in vitro phosphate binding capacity of the polymers of the invention in a non-interfering buffer can be greater than about 0.5, 1.0, 1.5, 2.0, 2.5, 3.0, 3.5, 4.0, 5.0, 6.0, 8.0, or 10.0 mmol/gr. In some embodiments, the in vitro phosphate binding capacity of the polymers of the invention for target ion is greater than about 0.5 mmol/gr, preferably greater than about 2.5 mmol/gr, even more preferably greater than about 3 mmol/gr, even more preferably greater than about 4 mmol/gr, and yet even more preferably greater than about 6 mmol/gr. In some embodiments, the phosphate binding capacity can range from about 0.5 mmol/gr to about 10 mmol/gr, preferably from about 2.5 mmol/gr to about 8 mmol/gr, and even more preferably from about 3 mmol/gr to about 6 mmol/gr. Several techniques are known in the art to determine the phosphate binding capacity. The in vitro phosphate binding capacity of the polymers of the invention is measured as described in Example 1 for measurement of binding capacity in a non-interfering buffer.

In some embodiments, the mean ex vivo phosphate binding capacity of phosphate-binding polymers of the invention, measured in digestive aspirates from human subjects, is greater than about 0.2, 0.3, 0.4, 0.5, 0.6, 0.7, 0.8, 0.9, 1.0, 1.2, 1.4, 1.6, 1.8, 2.0, 2.5, 3.0, 4.0, 5.0, or 6.0 mmol/gr. Ex vivo aspirates are obtained as described in Example 1, from normal subjects, and binding is measured as for a non-interfering buffer. Mean values are taken from about 5-15, or about 15-30, or about 30-60 subjects. In some embodiments, measurements are taken from 6-12 subjects.

As used herein, "mean in vivo phosphate binding capacity" refers to the binding capacity of a polymer as measured in normal human subjects unless otherwise specified, and where the phosphate binding of the polymer is measured by the decrease in the phosphate urinary excretion combined with measurement of the phosphate excreted in the feces as free and polymer-bound phosphate (see below). Mean values are taken from about 5-15, or about 15-30, or about 30-60 subjects. In some embodiments, measurements are taken from 6-12 subjects. In some embodiments, the mean in vivo phosphate binding capacity of the polymers of the invention, preferably measured in human subjects, is at least about 0.3 mmol/gr, at least about 0.5 mmol/gr, at least about 0.8 mmol/gr, at least about 1.0 mmol/gr, at least about 1.5 mmol/gr, at least about 2.0 mmol/gr, at least about 3.0 mmol/gr, at least about 4.0 mmol/gr, at least about 5.0 mmol/gr, or at least about 6.0 mmol/gr.

The in vivo binding capacity of the polymer can preferably be determined by measuring the balance of the target ion (e.g. phosphate ion) in mammals, preferably in humans: subjects are given a meal with a controlled content of phosphate and binding polymer, and are monitored for phosphate intake and phosphate excreted in the feces and in urine. The study comprises a washout period followed by a period where subjects take a daily dose, preferably t.i.d., of phosphate binder, followed by several days without treatment to observe the return to baseline. The depletion of phosphate in urine usually matches the increase of phosphate in the feces. The moles of phosphate excreted in the feces minus the baseline, divided by the weight of binder administered provides a measure of the in vivo binding capacity. Unless otherwise indicated, "in vivo" measurements referred to herein utilize the above protocol. Another method consists of measuring the phosphate binding in vivo and in situ following the protocol indicated in Example 1, wherein mammals are intubated by a double lumen tube to retrieve the chyme at a certain location of the small intestine. A meal with a given phosphate content is given together with a known content of phosphate binder and a marker. The marker can be a dye or a non absorbable polymer (e.g. polyethylene glycol), which is then titrated in the chyme to determine the dilution occurring during the digestion process. The actual concentration of binder is then calculated from the initial concentration in the meal and the dilution ratio measured from the marker experiment. The total phosphate is analyzed on the chyme sample. The "soluble" phosphate is measured by spinning down the sample and decanting the supernatant and assaying for phosphate. The "bound" phosphate is obtained by difference between the total and the soluble phosphate. Two series of experiments are made on a group of subjects (6-12) which alternatively take a placebo (microcrystalline cellulose) or the drug: The binding capacity is obtained by measuring the increase in "bound" phosphate between the two sets of experiments, i.e. with and without drug administration, and dividing by the concentration of binder. Calculation can be made either on a subject basis or on per group basis.

B. Preparation of Polymers

The polymers of the invention are prepared by methods known to those skilled in the art; for example: ion binding monomers or their precursors can be copolymerized in the presence of a crosslinker; a preformed ion binding polymer is subsequently crosslinked through a chemical reaction or irradiation; or a polymer precursor is first crosslinked and further reacted to generate ion binding functional groups on the polymer.

The polymers are obtained by direct or inverse suspension, emulsion, precipitation techniques, polymerization in aerosol or using bulk polymerization/crosslinking methods and size reduction processes such as extrusion and grinding. Processes can be carried out as batch, semi-continuous and continuous processes.

The swelling ratio, binding interference, binding capacity, and MW exclusion limit are affected by at least the following composition and process variables:

1—Concentration of the chemical crosslinks of the polymer chains.
2—The (monomer+crosslinker) to solvent ratio in the crosslinking reaction.
3—The net charge of the polymer (at the physiological pH and tonicity of the milieu in which it will be used).
4—The hydrophilic/hydrophobic balance of the backbone polymer.
5—The presence or absence of a core-shell structure, where the shell component restricts the extent of swelling of the core material.

In the following, the preferred operating ranges for composition and process variables are exemplified with crosslinked polyamine materials with phosphate binding properties. It will be understood that these are exemplary conditions only, and that the methods described herein may be used in the selection and production of polymers that bind a wide range of solutes, as will be apparent to one of skill in the art.

1) Concentration of the chemical crosslinks of the polymer chains. The concentration of chemical crosslinks is one important feature that controls the swelling properties and pore distribution of the polymer. One convenient way to describe the polymers of the invention is to define a amine repeat unit and its average number of connections to the rest of the polymer. "A" is defined as the amine repeat unit and "NC" is the average number of connections from A; NC can be 2, 3, 4 and higher. In order to form an insoluble gel, NC generally should be greater than 2.

NC values can be then translated into amine to crosslinker stoichiometric ratios by the following equations:

For low molecular weight monomers, e.g., N,N,N',N'-tetrakis(3-aminopropyl)1,4 diaminobutane or 1,3 diamino propane, NC=B·Fb/A, where B is the number of moles of crosslinker, Fb is the number of groups in B reacting with A to establish a covalent bond, and A is the number of moles of amine.

When the amine material is of high molecular weight and derives from the polymerization of an amine monomer, such as vinylamine, polyethyleneimine, polyvinylamine, or polyallylamine, the expression is changed to account for the 2 connections linking the monomer repeats within the polymer backbone. NC then becomes: NC=(2·A+B·Fb)/A.

Conversely, the mole ratio of crosslinker to amine can be computed from the desired NC value by manipulating the equations above:

Low molecular weight amine:

$$B/A = NC \cdot Fb$$

High molecular weight amine:

$$B/A = (NC-2) \cdot Fb$$

The table below shows some conversion examples between NC and the actual crosslinker to amine ratio, wherein the amine is either a high molecular weight material or a small molecule, and where the crosslinker material is either di or tri functional.

| Amine material | Type of amine | Crosslinkers | Fb | Desired NC | Mole ratio B/A | Equation used |
|---|---|---|---|---|---|---|
| Polyallylamine | High Mw | epichlorhydrine | 2 | 2.2 | 0.10 | b |
| Polyvinylamine | High Mw | 1,3 dichloropropane | 2 | 2.5 | 0.25 | b |
| polyethyleneimine | High Mw | N-tris(2chloro ethyl)amine | 3 | 2.2 | 0.07 | b |
| 1,3 diaminopropane | Low Mw amine | 1,3 dichloropropane | 2 | 2 | 1.00 | a |
| N,N,N',N'-tetrakis (3-aminopropyl) 1,4 diaminobutane | Low Mw amine | epichlorhydrine | 2 | 4 | 2.00 | a |

| Amine material | Type of amine | Crosslinkers | Fb | Desired NC | Mole ratio B/A | Equation used |
|---|---|---|---|---|---|---|
| N,N,N',N'-tetrakis (3-aminopropyl) 1,4 diaminobutane | Low Mw amine | N-tris(2chloro ethyl)amine | 3 | 4 | 1.33 | a | a: B/A = NC/Fb
b: B/A = (NC−2)/Fb

Surprisingly it was found that the binding selectivity, which reflects the in vivo efficacy, went through an optimum with respect to NC: in the low range of NC values, the material tended to swell considerably and corollary showed a lot of binding interference in a GI stimulant. In the high range however, the material had substantially low intrinsic binding capacity which obviously lowered the overall performance in vivo. The optimal NC values was found to lie between 2.05 and 5 depending upon the amine/crosslinker systems.

However the optimal range for giving the desired combination of characteristics in the final polymer depends on the specific monomer and crosslinker used, as well as other conditions used in the production process, such as initial concentration of the monomer in the reaction medium, and is a matter of routine experimentation.

In some embodiments, the ratio of crosslinker to total amine groups of the monomers in the polymer is greater than 50 mol %, 60 mol %, 70 mol %, 80 mol %, or 90 mol %.

In some embodiments of the invention providing a phosphate-binding polymer containing one or more low molecular weight amine monomers and one or more crosslinkers, NC is more than about 2, or more than about 3, or more than about 4. In some embodiments polymers are constructed from N,N,N',N'-tetrakis(3-aminopropyl)1,4 diaminobutane monomers (low MW monomers) crosslinked by epichlorohydrin (Fb=2), where B/A is from about 2.0 (mol/mol) to about 3.0 (mol/mol) (i.e, NC is from about 4 to about 6), or from about 2.3 (mol/mol) to about 2.7 (mol/mol) (i.e, NC is from about 4.6 to about 5.4), or about 2.5 (mol/mol) (i.e, NC is about 5.0). In some embodiments polymers are constructed from N,N,N',N'-tetrakis(3-aminopropyl)1,4 diaminobutane monomers crosslinked by epichlorohydrin, where the initial ratio of monomer to water is from about 3:1 w/w to 1:3 w/w, or from about 1.5:1 to about 2:1 w/w, or about 1:1, or about 3:1, where B/A is from about 2.0 (mol/mol) to about 3.0 (mol/mol) (i.e, NC is from about 4 to about 6), or from about 2.3 (mol/mol) to about 2.7 (mol/mol) (i.e, NC is from about 4.6 to about 5.4), or about 2.5 (mol/mol) (i.e, NC is about 5.0).

2) The (monomer+crosslinker) to solvent ratio in the crosslinking reaction. High ratios of (monomer+crosslinker) to solvent favor densely crosslinked materials when all other conditions are kept constant. For instance, when a high molecular weight amine is used and when the chain length and the polymer concentration are large enough, chain entanglements are produced that generate many crosslinking nodes once the structure is chemically crosslinked. More generally, for both high and low molecular weight amines, high (monomer+crosslinker) to solvent ratio tends to minimize the extent of side reactions leading to gel defects (e.g. intrachain crosslinking leading to cyclic structures, incomplete crosslinking reaction leading to dangling ends).

This condition is determined primarily by the concentrations in the reaction medium of both the monomer (e.g., amine) and the crosslinker. In some embodiments of the invention, the concentration of monomer and crosslinker in the reaction medium is greater than about 20 wt %, preferably greater than 40 wt %, more preferably greater than 60% wt %. In some embodiments, a (monomer+crosslinker):solvent (e.g., water) ratio of between about 3:1 to about 1:3 (w/w) is used. In some embodiments, a (monomer+crosslinker):solvent (e.g., water) ratio of between about 3:1 to about 1:1 (w/w) is used. In some embodiments, a (monomer+crosslinker):solvent (e.g., water) ratio of about 3:1, or about 2.5: 1, or about 2.0:1, or about 1.5:1, or about 1:1 (w/w) is used. The crosslinker may be added at various times, depending on the polymerization procedure. In some embodiments, the initial monomer:solvent ratio (before addition of crosslinker) is between about 4:1 to about 1:1, or between about 3:1 to about 1:1; crosslinker is then added to comprise between about 100 mol % to about 400 mol % of the initial monomer content, or between about 200 mol % to about 300 mol % of the initial monomer content. In some embodiments, the monomer is N,N,N',N'-tetrakis(3-aminopropyl)1,4 diaminobutane monomers and the crosslinker is epichlorohydrin, and the initial monomer:water ratio is between about 4:1 to 1:1, or between about 3:1 to about 1:1, or about 1.7, or about 1.73; and the crosslinker is added to between about 200 mol % to about 300 mol % of the monomer content, or about 230 mol % to about 270 mol %, or about 250 mol %.

In some embodiments, e.g. embodiments in which the monomer is a polyallyamine, the amount of monomer is much greater than the amount of crosslinker (e.g., ten-fold crosslinker on a molar basis and even greater on a weight basis), and the above ratios may be expressed as monomer:solvent ratios, ignoring crosslinker. In some embodiments, the monomer (e.g., polyallylamine) is present at a monomer:solvent ratio of about 3:1 to about 1:3. In some embodiments, the monomer is polyallylamine and the crosslinker is epichlorohydrin, where the polyallylamine is present at monomer:water ratio of about 3:1 to about 1:3, and epichlorhydrin is added to the reaction mix to about 10 mol % of the total polyallylamine content.

When possible solvent free process are even more preferred: in one embodiment the amine and the crosslinker are quickly mixed and subsequently dispersed neat in a continuous phase, e.g. water. The crosslinking reaction is taking place within the dispersed droplets and recovered as beads.

3) The net charge of the polymer (at the physiological pH and tonicity). The net charge of the polymer is given by the mole content of the ion-binding, its intrinsic charge and degree of ionization at physiological pH. The charge density is preferably in the range of 3 to 20 mmol/gr, preferably 6 to 15 mmol/gr.

4) The hydrophilic/hydrophobic balance of the backbone polymer. The hydrophilic/hydrophobic balance of the polymer allows one to control somewhat independently the chemical crosslinking density and the swelling ratio. The swelling ratio is very sensitive to the polymer solvent interaction parameter $\chi ij$ as described in the Flory-Huggins formalism (Flory P. J. "Principles of Polymer Chemistry, Cornell Ithaca Pub. 1953)). Increasing $\chi ij$ values up to 0.4 and above create a poor solvent conditions for the polymer, which then tries to minimize monomer to solvent (water) interaction and consequently swells much less. This can be achieved by incorporating hydrophobic moieties in the gel, such as long chain hydrophob, (poly)aromatic substituents, or fluorinated groups. When this strategy is chosen to control the extent of swelling and consequently the exclusion limit of the gels, the level of hydrophobic monomers and crosslinkers is between about 0.5 mol % to about 50 mol %, preferably between about 20% and 50%.

In preferred methods, the absolute hydrophobicity is quantified by the absolute difference in the log P of the monomers. Quantitatively, the hydrophobic/hydrophilic nature of the monomers may be determined according to the log P of the particular monomers, which is sometimes referred to as the octanol-water partition coefficient. Log P values are well known and are determined according to a standard test that determines the concentration of monomer in a water/1-octanol separated mixture. In particular, computer programs are commercially available as well as on the internet that will estimate the log P values for particular monomers. Some of the log P values in this application were estimated from the web sitehttp://esc.syrres.com/interkow/kowdemo.htm, which provides an estimated log P value for molecules by simply inserting the CAS registry number or a chemical notation. Hydrophobic monomers typically will have a log P value above zero and hydrophilic monomers typically will have a log P value close to or below zero. Generally, the log P of the hydrophobic monomers for the purposes of this invention should be at least about 0.5, more preferably at least about 0.75, even more preferably at least about 1.0, still more preferable at least about 1.5 and most preferably at least about 2.

5) The presence of a core-shell structure, where the shell component restricts the extent of swelling of the core material. Gel particles with a core-shell morphologies are useful in the context of the invention: the shell material can limit the swelling, hence limit the exclusion limit, by imposing a mechanical resistance on the swelling pressure stemming from the core material, which would otherwise swell to a much higher extent. The shell material can be of the same composition than the core, but with a higher crosslink density. The design of such core-shell materials and method of making thereof can be found in U.S. patent application Ser. No. 10/814,789.

The shell material can be chemically anchored to the core material or physically coated. In the former case, the shell can be grown on the core component through chemical means, for example by: chemical grafting of shell polymer to the core using living polymerization from active sites anchored onto the core polymer; interfacial reaction, i.e., a chemical reaction located at the core particle surface, such as interfacial polycondensation; and using block copolymers as suspending agents during the core particle synthesis.

The interfacial reaction and use of block polymers are preferred techniques when chemical methods are used. In the interfacial reaction pathway, typically, the periphery of the core particle is chemically modified by reacting small molecules or macromolecules on the core interface. For example, an amine containing ion-binding core particle is reacted with a polymer containing amine reactive groups such as epoxy, isocyanate, activated esters, halide groups to form a crosslinked shell around the core.

In another embodiment, the shell is first prepared using interfacial polycondensation or solvent coacervation to produce capsules. The interior of the capsule is then filled up with core-forming precursors to build the core within the shell capsule.

In some embodiments, using the block copolymer approach, an amphiphilic block copolymer can be used as a suspending agent to form the core particle in an inverse or direct suspension particle forming process. When an inverse water-in-oil suspension process is used, then the block copolymer comprises a first block soluble in the continuous oil phase and another hydrophilic block contains functional groups that can react with the core polymer. When added to the aqueous phase, along with core-forming precursor, and the oil phase, the block copolymer locates to the water-in-oil interface and acts as a suspending agent. The hydrophilic block reacts with the core material, or co-reacts with the core-forming precursors. After the particles are isolated from the oil phase, the block copolymers form a thin shell covalently attached to the core surface. The chemical nature and length of the blocks can be varied to vary the permeation characteristics of the shell towards solutes of interest.

When the shell material is physically adsorbed on the core material, well known techniques of microencapsulation such as solvent coacervation, fluidized bed spray coater, or multiemulsion processes can be used. A preferred method of microencapsulation is the fluidized bed spray coater in the Wurster configuration. In yet another embodiment, the shell material is only acting temporarily by delaying the swelling of the core particle while in the mouth and esophagus, and optionally disintegrate in the stomach or duodenum. The shell is then selected in order to hinder the transport of water into the core particle, by creating a layer of high hydrophobicity and very low liquid water permeability.

Thus, in one aspect the invention provides a method of selecting an ion-binding polymer, where the polymer contains a monomer and a crosslinker, and where the polymer possesses at least one of the features of a) a swelling ratio of less than about 5; b) a gel pore volume distribution measured in a physiological medium characterized by a fraction of said pore volume accessible to non-interacting solutes, of molecular weight greater than about twice the MW of the target anion, of less than about 20% of the weight of the gel; and c) an ion-binding interference for the target anion lower than about 60% when measured in a gastrointestinal simulant, relative to a non-interfering buffer, by:
    i) varying the following composition and process variables
        1) the ratio of crosslinker to monomer;
        2) the ratio of (monomer+crosslinker) to solvent in the reaction medium;
        3) the net charge of the polymer at physiological pH and tonicity; and/or
        4) the hydrophilic/hydrophobic balance of the backbone polymer
    ii) evaluating the swellability, porosity, and ion binding interference of the resulting polymer; and
    iii) selecting a polymer that possesses at least one of the above features.

In another aspect, the invention provides a method for improving the therapeutic properties and/or suitability for administration and/or pharmaceutical properties of a polyamine polymer comprising at least one of the following steps: a) crosslinking said polymer with a crosslinker, such that the average number of connection to the polyamine monomer is between about 2.05 and about 6; and/or b) producing said polymer by a process wherein the polyamine is initially present in water at a ratio of polyamine:water of from about 3:1 to about 1:3.

C. Monomers

Any suitable monomers and crosslinkers may be used in the polymers of the invention. When the polymer binds phosphate or oxalate, the polymer usually comprises a polyamine and a crosslinker. The polyamines include amine functional monomers such as those described in U.S. Pat. Nos. 5,496,545; 5,667,775; 6,509,013; 6,132,706; and 5,968,499; and U.S. patent applications Ser. Nos. 10/806,495 and 10/701,385. These patents and patent applications are hereby incorporated by reference in their entirety.

In some embodiments, the invention provides ion-binding polymers that contain crosslinked amine moieties. In some of these embodiments, the polymers are characterized by one or more of the characteristics of low swelling, high ion binding in vivo, low interference from interfering ions, and/or specific porosity. Polymers, including homopolymers and copolymers, with repeating crosslinked amine units are referred to herein as crosslinked amine polymers. The repeating amine units in the polymer can be separated by the same or varying lengths of repeating linker (or intervening) units. In some embodiments, the polymers comprise of repeat units of an amine plus intervening linker unit. In other embodiments, multiple amine units are separated by one or more linker units.

One monomer useful in the polymers of the invention comprises an amine of formula I

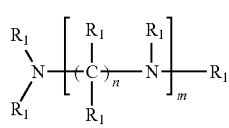

(I)

wherein each n, independently, is equal to or greater than 3; m is equal to or greater than 1; and each $R_1$, independently, is H or optionally substituted alkyl or aryl or is linked to a neighboring $R_1$ to form an optionally substituted alicyclic, aromatic, or heterocyclic group. In one embodiment the invention is a crosslinked amine polymer comprising an amine of Formula I, as described, where the amine is crosslinked with a crosslinking agent.

Preferred amines of formula I include:

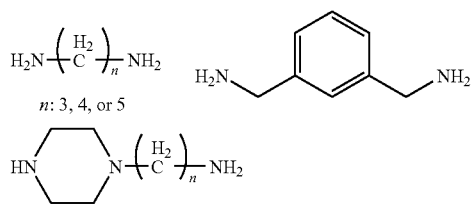

In one aspect the invention provides methods of treating an animal, including a human, using the polymers of the invention. One embodiment of this aspect is a method for removing phosphate from the gastrointestinal tract of an animal by administering an effective amount of a crosslinked amine polymer, wherein said polymer comprises an amine of formula I.

A second monomer useful in the polymers of the invention comprises an amine of formula II

(II)

wherein p is 1, 2, 3, or 4; each $R_1$, independently, is H or optionally substituted alkyl or aryl or is linked to a neighboring $R_1$ to form an optionally substituted alicyclic, aromatic, or heterocyclic group; $R_2$ and $R_3$, each independently, are H or optionally substituted alkyl or aryl, with the proviso that when p=1, both $R_2$ and $R_3$ are not H and when p=2, 3, or 4, $R_2$ and $R_3$ are H, alkyl or $-C(R_1)_2-R_4-N(R_1)_2$, $R_4$ being either a bond or methylene; in addition, in some of the embodiments, the amines of formula II include amines wherein p is greater than 4. In various embodiments, p can be more than 8, more than 12, more than 16, or more than 20. In other embodiments, p can be less than 25, less than 20, less than 15, or less than 10. In one embodiment the invention is a crosslinked amine polymer comprising an amine of formula II, as described, where the amine is crosslinked with a crosslinking agent.

Preferred amines of formula II include:

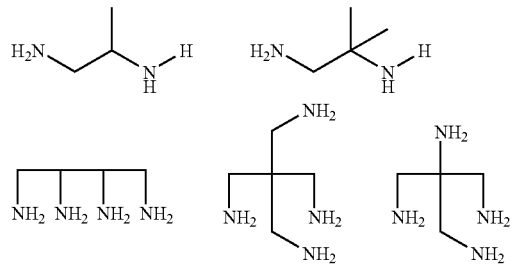

One embodiment of the invention is a method for removing phosphate from the gastrointestinal tract of an animal by administering an effective amount of a crosslinked amine polymer, wherein said polymer comprises an amine of formula II.

A third monomer useful in the polymers of the invention comprises an amine of formula III

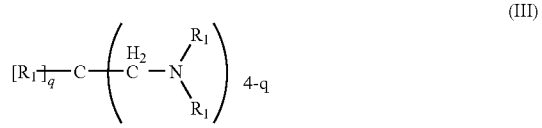

(III)

wherein q is 0, 1, or 2; and each $R_1$, independently, is H or optionally substituted alkyl or aryl or is linked to a neighboring $R_1$ to form an optionally substituted alicyclic, aromatic, or heterocyclic group. In one embodiment the invention is a crosslinked amine polymer comprising an amine of formula III, as described, where the amine is crosslinked with a crosslinking agent.

Preferred amines of formula III include:

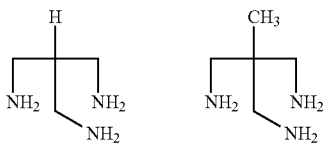

One embodiment of the invention is a method for removing phosphate from the gastrointestinal tract of an animal by administering an effective amount of a crosslinked amine polymer, wherein said polymer comprises an amine of formula III.

A fourth monomer useful in the polymers of the invention comprises an amine of formula IV

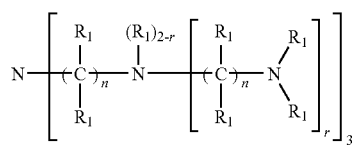

wherein each n, independently, is equal to or greater than 3; each r, independently, is 0, 1, or 2; and each $R_1$, independently, is H or optionally substituted alkyl or aryl or is linked to a neighboring $R_1$ to form an optionally substituted alicyclic, aromatic, or heterocyclic group. In one embodiment the invention is a crosslinked amine polymer comprising an amine of formula IV, as described, where the amine is crosslinked with a crosslinking agent.

A preferred amine of formula IV includes:

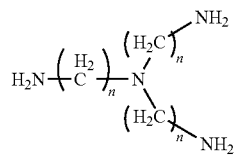

One embodiment of the invention is a method for removing phosphate from the gastrointestinal tract of an animal by administering an effective amount of a crosslinked amine polymer, wherein said polymer comprises an amine of formula IV.

A fifth monomer useful in the polymers of the invention comprises an amine of formula V

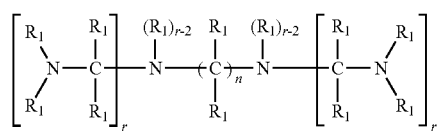

wherein each n, independently, is equal to or greater than 3; each r, independently, is 0, 1, or 2; and each $R_1$, independently, is H or optionally substituted alkyl or aryl or is linked to a neighboring $R_1$ to form an optionally substituted alicyclic, aromatic, or heterocyclic group. In one embodiment the invention is a crosslinked amine polymer comprising an amine of formula V, as described, where the amine is crosslinked with a crosslinking agent.

Preferred amines of formula V include:

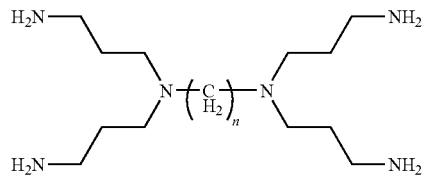

n: 3, 4, or 5

One embodiment of the invention is a method for removing phosphate from the gastrointestinal tract of an animal by administering an effective amount of a crosslinked amine polymer, wherein said polymer comprises an amine of formula V.

A sixth monomer useful in the polymers of the invention comprises an amine of formula VI

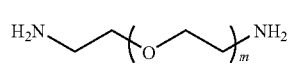

wherein each m, independently, is equal to or greater than 3. In one embodiment the invention is a crosslinked amine polymer comprising an amine of formula VI, as described, where the amine is crosslinked with a crosslinking agent.

One embodiment of the invention is a method for removing phosphate from the gastrointestinal tract of an animal by administering an effective amount of a crosslinked amine polymer, wherein said polymer comprises an amine of formula VI.

The amines represented by general formulas I-VI can be synthesized by methods well known in the art. These synthesis techniques include catalytic conversion from alcohols, reductive amination of carbonyl compounds, Michael additions, and hydrogenation of nitrites (see, for example, Karsten Eller et al, Ullmann's Encyclopedia of Industrial Chemistry 2002 by Wiley-VCH Verlag GmbH & Co. KGaA). Several small amine monomers and/or amine plus intervening linker units are also commercially available.

In one embodiment, an amine useful in the present invention, tetramethylene tetramine, depicted below, is synthesized by catalytic hydrogenation of the commercially available diaminomaleonitrile (DAMN):

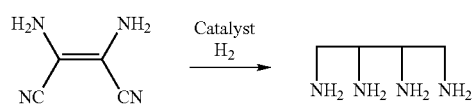

Amines that may be used in the present invention are not limited to, but are typically small amines that serve as monomers or parts of monomeric units for the polymerization reactions. In some embodiments, the monomers are low-molecular weight monomers, i.e., monomers of a molecular weight less than 200 g/mol.

In embodiments of the invention, the monomers are non-polymeric, e.g., non-polymeric amines. As used herein, a "polymer" encompasses a molecule of high relative molecular mass, the structure of which essentially comprises the multiple repetition of units derived, actually or conceptually, from molecules of low relative molecular mass.

Examples of amines that are suitable for synthesis of the polymers of the present invention include, but are not limited to, the amines shown in Table 1.

TABLE 1

| Label | Type | Structure | MW (g/mol) |
|---|---|---|---|
| B-SM-20-TeA | Tetramine | (structure) | 316.54 |
| B-SM-22-DA | Diamine | (structure) | 61.1 |
| B-SM-23-DA | Diamine | (structure) | 88.15 |
| B-SM-24-DA | Diamine | (structure) | 74.13 |
| B-SM-25-DA | Diamine | (structure) | 88.15 |
| B-SM-26-DA | Diamine | (structure) | 129.21 |
| B-SM-27-DA | Diamine | (structure) | 114.19 |
| B-SM-28-TA | Triamine | (structure) 2HCl | 196.08 |
| B-SM-29-TA | Triamine | (structure) | 125.13 |
| B-SM-31-DA | Diamine | (structure) 2HCl | 184.07 |

TABLE 1-continued

| Label | Type | Structure | MW (g/mol) |
|---|---|---|---|
| B-SM-32-DA | Diamine | 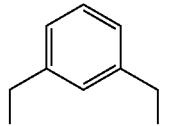 | 136.2 |

Additional amine monomers that may be used in polymers of the invention include vicinal amine moieties. The polymer may be a homopolymer including repeat units of vicinal amines or is a copolymer including one or more repeat units of vicinal amines and other monomers such as acrylates, methacrylates, acrylamides, methacrylamides, vinyl esters, vinyl amides, olefin, styrenic, etc. The size of the polymer can vary between, for example, about 500 to about 1,000,000 Daltons.

One vicinal amine monomer useful in the polymers of the invention is the monomer shown in formula VII:

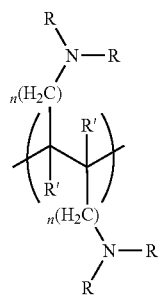

Formula VII wherein n is zero, one, or greater than 1, each R is independently a suitable chemical group that complements the valency of nitrogen, and each R' is independently H, alkyl, or amino.

In another embodiment, the polymer is characterized by a repeating unit having the formula

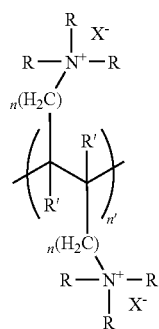

Formula VIII or a copolymer thereof, wherein n is zero, one, or greater than 1, each R is independently a suitable chemical group that complements the valency of nitrogen, each R' is independently H, alkyl, or amino, and $X^-$ is a negatively charged organic or inorganic counterion.

Preferred polymers of formula VIII include:

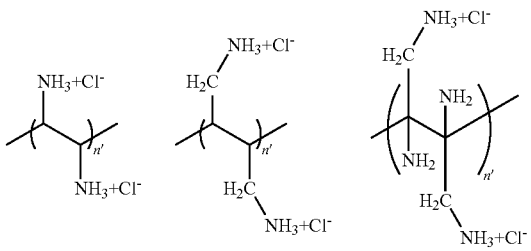

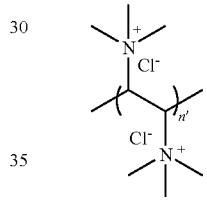

The polymers of the present invention also include polymers characterized by a repeat unit having the formula

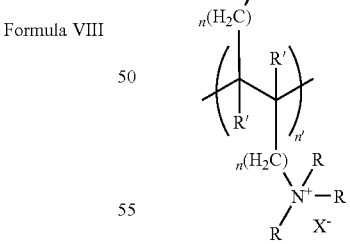

Formula IX wherein n is zero, one, or greater than 1, each R is independently a suitable chemical group that complements the valency of nitrogen, each R' is independently H, alkyl, or amino, and $X^-$ is a negatively charged organic or inorganic counterion.

In one embodiment, the R groups of neighboring nitrogen atoms are linked to each other to have a structure as depicted in formula X.

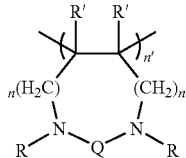

Formula X wherein Q is a bond, alkyl, alkylamino, alkylcarbonyl, alkenyl, aryl, or heterocyclyl.

In the polymers described herein, n is zero, one, or greater than 1. In preferred embodiments, n is 0-5, even more preferably n is zero or 1.

The value of n' depends on the desired properties of the polymer, the potential use of the polymer, and the synthesis techniques used.

The pendant nitrogen atom of formulas VII, VIII, IX, and X can be bound to atoms such as C, H, O, S, P and N such that the pendant groups are nitroso, nitro, nitroxide radical, nitrone, nitrene, isocyanate, carbazide, hydrazino, diazo groups, imine, amidine, guanidine, sulfamate, phosphoramidate, and heterocycle.

Examples of suitable R groups include H, halogen, R", $CO_2H$, $CO_2R"$, $COR"$, $C(=N\ R")(N\ R")$, CN, $CONH_2$, $CONR'_2$, $OR"$, $SO_3R"$, $Si(R")_3$, and $P(O)(OR")_2$. Suitable R" groups include H, optionally substituted alkyl, acyl, alkylamino, alkenyl, heterocyclyl, and aryl group. Preferred R' is H, methyl, or amino.

The substituents for R" groups can be ionic entities with oxygen, nitrogen, phosphorus, or sulfur. Examples of substituents are carboxylate, sulfonate, sulfamate, sulfone group, phosphonate, phosphazene, phosphoramidate group, quaternary ammonium groups, or amine groups, e.g., primary and secondary alkyl or aryl amines. Examples of other suitable substituents include hydroxy, alkoxy, carboxamide, sulfonamide, halogen, alkyl, aryl, hydrazine, guanadine, urea, and carboxylic acid esters.

Preferred R groups include H and the following groups:

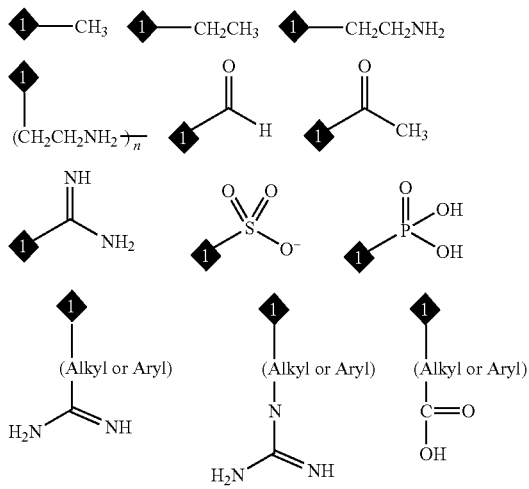

-continued

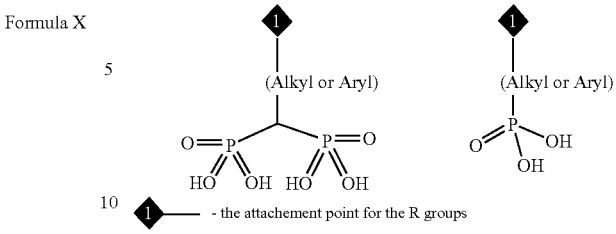

◆ — the attachement point for the R groups

The negatively charged counterions, $X^-$, can be organic ions, inorganic ions, or a combination thereof. The inorganic ions suitable for use in this invention include halide (especially chloride), carbonate, bicarbonate, sulfate, bisulfate, hydroxide, nitrate, persulfate and sulfite. Suitable organic ions include acetate, ascorbate, benzoate, citrate, dihydrogen citrate, hydrogen citrate, oxalate, succinate, tartrate, taurocholate, glycocholate, and cholate. Preferred $X^-$ is chloride or carbonate.

In a preferred embodiment, the counterion does not have a detrimental side effect to the patient and is selected to have a therapeutic or nutritional benefit to the patient.

Another monomer of use in the polymers of the invention is formula XI shown below,

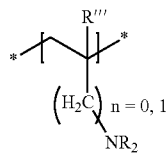

wherein R'" is H or $CH_3$, and R has the same meaning as above. Preferred structures of formula XI are when R=H.

In one embodiment, the polymer is a copolymer with one of the repeat units being a monomer as described herein.

The copolymers of the present invention can be alternative or random copolymers. Generally, monomers that may be co-polymerized with the amine precursors include one or more monomers selected from the group consisting of styrene, substituted styrene, alkyl acrylate, substituted alkyl acrylate, alkyl methacrylate, substituted alkyl methacrylate, acrylonitrile, methacrylonitrile, acrylamide, methacrylamide, N-alkylacrylamide, N-alkylmethacrylamide, N,N-dialkylacrylamide, N,N-dialkylmethacrylamide, isoprene, butadiene, ethylene, vinyl acetate, N-vinyl amide, maleic acid derivatives, vinyl ether, allyle, methallyl monomers and combinations thereof. Functionalized versions of these monomers may also be used. Specific monomers or comonomers that may be used in this invention include, but are not limited to, methyl methacrylate, ethyl methacrylate, propyl methacrylate (all isomers), butyl methacrylate (all isomers), 2-ethylhexyl methacrylate, isobornyl methacrylate, methacrylic acid, benzyl methacrylate, phenyl methacrylate, methacrylonitrile, α-methylstyrene, methyl acrylate, ethyl acrylate, propyl acrylate (all isomers), butyl acrylate (all isomers), 2-ethylhexyl acrylate, isobornyl acrylate, acrylic acid, benzyl acrylate, phenyl acrylate, acrylonitrile, styrene, glycidyl methacrylate, 2-hydroxyethyl methacrylate, hydroxypropyl methacrylate (all isomers), hydroxybutyl methacrylate (all isomers), N,N-dimethylaminoethyl methacrylate, N,N-diethylaminoethyl methacrylate, triethyleneglycol methacrylate, itaconic anhydride, itaconic acid, glycidyl acrylate, 2-hydroxyethyl acrylate, hydroxypropyl acrylate (all isomers), hydroxybutyl acrylate (all isomers), N,N-dimethylaminoethyl acrylate, N,N-diethylaminoethyl acrylate, triethyleneglycol acrylate, methacrylamide, N-methylacrylamide, N,N-dimethylacrylamide, N-tert-butylmethacrylamide, N-n-butylmethacrylamide, N-methylolmethacrylamide, N-ethylolmethacrylamide, N-tert-butylacrylamide, N-n-butylacrylamide, N-methylolacrylamide, N-ethylolacrylamide, 4-acryloylmorpholine, vinyl benzoic acid (all isomers), diethylaminostyrene (all isomers), α-methylvinyl benzoic acid (all isomers), diethylamino a-methylstyrene (all isomers), p-vinylbenzene sulfonic acid, p-vinylbenzene sulfonic sodium salt, trimethoxysilylpropyl methacrylate, triethoxysilylpropyl methacrylate, tributoxysilylpropyl methacrylate, dimethoxymethylsilylpropyl methacrylate, diethoxymethylsilylpropyl methacrylate, dibutoxymethylsilylpropyl methacrylate, diisopropoxymethylsilylpropyl methacrylate, dimethoxysilylpropyl methacrylate, diethoxysilylpropyl methacrylate, dibutoxysilylpropyl methacrylate, diisopropoxysilylpropyl methacrylate, trimethoxysilylpropyl acrylate, triethoxysilylpropyl acrylate, tributoxysilylpropyl acrylate, dimethoxymethylsilylpropyl acrylate, diethoxymethylsilylpropyl acrylate, dibutoxymethylsilylpropyl acrylate, diisopropoxymethylsilylpropyl acrylate, dimethoxysilylpropyl acrylate, diethoxysilylpropyl acrylate, dibutoxysilylpropyl acrylate, diisopropoxysilylpropyl acrylate, maleic anhydride, N-phenylmaleimide, N-butylmaleimide, N-vinylformamide, N-vinyl acetamide, allylamine, methallylamine, allylalcohol, methyl-vinylether, ethylvinylether, butylvinyltether, butadiene, isoprene, chloroprene, ethylene, vinyl acetate and combinations thereof. The preferred monomers or comonomers are acrylamide, dimethylacrylamide, N-vinyl formamide, N-vinylacetamide, vinyl acetate, methyl acrylate, and butyl acrylate.

Further monomers that may be used in the polymer of the invention include:

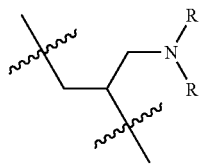

where each R, independently, is H or a substituted or unsubstituted alkyl, such as a lower alkyl (e.g., having between 1 and 5 carbon atoms, inclusive), alkylamino (e.g., having between 1 and 5 carbons atoms, inclusive, such as ethylamino) or aryl (e.g., phenyl) group;

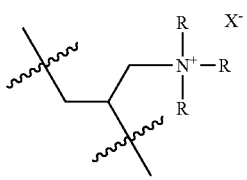

where each R, independently, is H or a substituted or unsubstituted alkyl (e.g., having between 1 and 5 carbon atoms, inclusive), alkylamino (e.g., having between 1 and 5 carbons atoms, inclusive, such as ethylamino) or aryl (e.g., phenyl) group, and each $X^-$ is an exchangeable negatively charged counterion.

Another suitable monomer is a structure of the formula

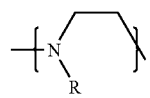

where R is H or a substituted or unsubstituted alkyl (e.g., having between 1 and 5 carbon atoms, inclusive), alkylamino (e.g., having between 1 and 5 carbons atoms, inclusive, such as ethylamino) or aryl group (e.g., phenyl).

Another suitable monomer is a structure of the formula

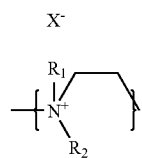

where each $R_1$ and $R_2$, independently, is H or a substituted or unsubstituted alkyl (e.g., having between 1 and 5 carbon atoms, inclusive), and alkylamino (e.g., having between 1 and 5 carbons atoms, inclusive, such as ethylamino) or aryl group (e.g., phenyl), and each $X^-$ is an exchangeable negatively charged counterion. In one embodiment, at least one of the R groups is a hydrogen atom.

Another suitable monomer is a structure of the formula

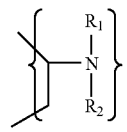

where each $R_1$ and $R_2$, independently, is H, a substituted or unsubstituted alkyl group containing 1 to 20 carbon atoms, an alkylamino group (e.g., having between 1 and 5 carbons atoms, inclusive, such as ethylamino), or an aryl group containing 6 to 12 atoms (e.g., phenyl).

Another suitable monomer is a structure of the formula

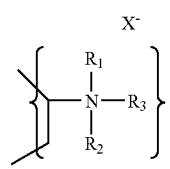

where each $R_1$ and $R_2$ and $R_3$, independently, is H, a substituted or unsubstituted alkyl group containing 1 to 20 carbon atoms, an alkylamino group (e.g., having between 1 and 5 carbons atoms, inclusive, such as ethylamino), or an aryl group containing 6 to 12 atoms (e.g., phenyl), and each $X^-$ is an exchangeable negatively charged counterion.

In each case for these monomers, the R groups can carry one or more substituents. Suitable substituents include therapeutic anionic groups, e.g., quaternary ammonium groups, or amine groups, e.g., primary and secondary alkyl or aryl amines. Examples of other suitable substituents include hydroxy, alkoxy, carboxamide, sulfonamide, halogen, alkyl, aryl, hydrazine, guanadine, urea, and carboxylic acid esters, for example.

The negatively charged counterions, X⁻, can be organic ions, inorganic ions, or a combination thereof. The inorganic ions suitable for use in this invention include halide (especially chloride), carbonate, bicarbonate, sulfate, bisulfate, hydroxide, nitrate, persulfate and sulfite. Suitable organic ions include acetate, ascorbate, benzoate, citrate, dihydrogen citrate, hydrogen citrate, oxalate, succinate, tartrate, taurocholate, glycocholate, and cholate.

Polymers containing guanidino groups are also useful as compositions that may be produced by the processes described herein to have the desired properties, and that bind anions such as phosphate and oxalate. Such polymers are described in U.S. Pat. Nos. 6,132,706; and 5,968,499, which are hereby incorporated by reference in their entirety. Briefly, guanidino groups are attached to a polymeric structure. The nature of the polymeric backbone is not of primary importance as the binding effect is due to the guanidino groups. Preferred polymers in which crosslinking and other factors may be controlled include polymers having a polyethylene backbone crosslinked with divinyl benzene. Polymers having an inorganic backbone, for example the polyphosphazene polymers, may also be used. The polymers may be copolymers derived from two or more different types of monomer. Further examples of useful polymers are carbohydrate polymers including cellulose and agarose. The guanidino groups are attached to the polymer backbone by means of chemical bonding through the terminal NH group of the guanidino group (NH₂—C(=NH)—NH—). The chemical bonding of the guanidino groups to the polymer backbone may be directly or via some form of grouping acting as a "spacer" through which it is attached to the polymer backbone. Various forms of attachment may be used, preferred forms varying according to the basic type of polymer. For example, alkylene groups of 1-4 carbon atoms, amide groups, ether groups or a combination thereof may be used. The preferred mode of attachment of guanidino groups to the polymer backbone will obviously depend upon the nature of the backbone but for simplicity direct bonding between atoms of the backbone and the NH group of the guanidino group is preferred where possible.

Methods of preparing the guanidino-containing polymers will be apparent to a person skilled in the art but for example, they may be prepared following the teachings of Schnaar, R. L. and Lee, Y. C., 1975, Biochemistry 14, 1535-1541, hereby incorporated by reference in its entirety, who describes a method for linking biologically active ligands to a polymer matrix, or the polymers may also conveniently be prepared through the reaction with a polymer containing amino groups attached to the polymer backbone of (a) 3,5-dimethylpyrazole-1-carboxamidine nitrate, (b) S-methylthiouronium sulphate or (c) O-methylpseudourea hydrogen sulphate.

Preferred monomers of the invention are amines. Most preferred monomers for use in the polymers of the invention include allylamine, vinylamine, ethyleneimine, methylene 1,3 diamino propane, and N,N,N',N'-tetrakis(3-aminopropyl) 1,4 diaminobutane, 1,2,3,4 tetraaminobutane, formula 1 and formula 2, wherein formula 1 and formula 2 are the following structures:

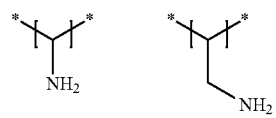

In some embodiments, polymers of the invention are composed of one or more amine monomers and one or more crosslinkers where the polymer is produced by a process in which the amine is present in solvent before crosslinking at a ratio of amine:solvent of from about 3:1 to about 1:3 and the total content crosslinkers added to the reaction mix is such that the average number of connections to the amine monomers is between about 2.05 and about 6, or between about 2.2 and about 4.5. In some embodiments, polymers of the invention are a phosphate-binding polymer composed of one or more amine monomers and one or more crosslinkers where the polymer is produced by a process wherein the total content crosslinkers added to the reaction mix is such that the average number of connections to the amine monomers is between 2.2 and 4.5. In preferred embodiments, the amine monomer is selected from the group consisting of 1,3 diamino propane, and N,N,N',N'-tetrakis(3-aminopropyl)1,4 diaminobutane, and wherein the crosslinker is selected from the group consisting of 1,3 dichloropropane and epichlorohydrin. In some embodiments, polymers of the invention are composed of one or more amine monomers and one or more crosslinkers, wherein the amine monomers are not polyallylamine monomers and/or the crosslinkers are not epichlorhydrin.

In some embodiments, e.g., in phosphate-binding polymers, it is desirable to keep the chloride to amine ratio of the final polymer below certain levels. In some embodiments, this is about 0 to about 35 mol %, preferably about 0 to about 15 mol %. Monomers may be selected according to this criterion.

D. Crosslinkers

The crosslinker include those described in U.S. Pat. Nos. 5,496,545; 5,667,775; 6,509,013; 6,132,706; and 5,968,499; and U.S. patent applications Ser. Nos. 10/806,495 and 10/701,385.

Crosslinking agents are typically compounds having at least two functional groups that are selected from a halogen group, carbonyl group, epoxy group, ester group, acid anhydride group, acid halide group, isocyanate group, vinyl group, and chloroformate group. The crosslinking agent may be attached to the carbon backbone or to the pendant nitrogen of the amine polymer. Examples of crosslinkers that are suitable for synthesis of the polymers of the present invention include, but are not limited to, the crosslinkers shown in Table 2.

TABLE 2

| Label | Structure | Mw |
|---|---|---|
| X-EP-1 | 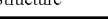 | 92.52 |
| X-EP-2 | 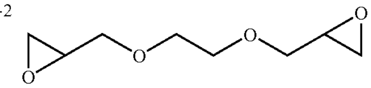 | 174.19 |

TABLE 2-continued
| Label | Structure | Mw |
|---|---|---|
| X-EP-3 | 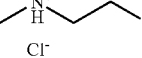 | |
| X-EP-4 | 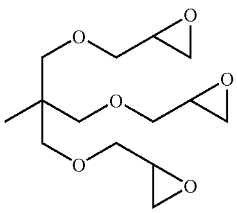 | 302.37 |
| X-EP-5 | 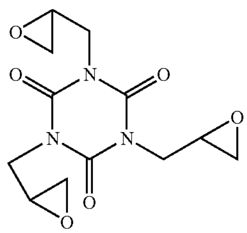 | 297.27 |
| X-EP-6 | 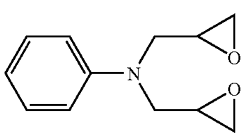 | 277.32 |
| X-EP-7 | 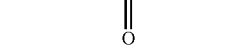 | 86.09 |
| X-EP-8 | 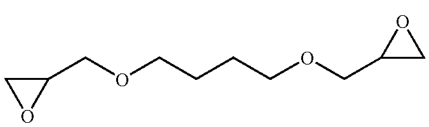 | 202.25 |
| X-Cl-1 | 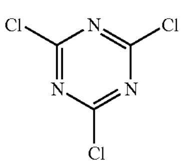 | 184.41 |
| X-Cl-2 | 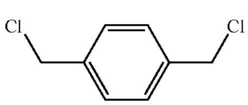 | 175.06 |
| X-Cl-3 | 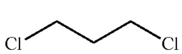 | 112.99 |
| X-Cl-4 | 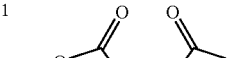 | 178.49 |
| X-Cl-5 | 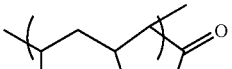 | 240.99 |
| X-Cl-6 | Cl∼∼∼Cl | 127.01 |
| X-AC-1 |  | 203.02 |
| X-AC-2 | | 203.02 |
| X-AC-3 | | 265.48 |
| X-AC-4 | | 154.98 |
| X-AH-1 | | 198.13 |
| X-AH-2 | | |
| X-AH-3 | | 112.08 |
| X-Mc-1 |  | 168.2 |

TABLE 2-continued

| Label | Structure | Mw |
|---|---|---|
| X-Mc-2 | (divinyl sulfone) | 118.16 |
| X-Mc-3 | (1,3,5-triacryloylhexahydro-1,3,5-triazine) | 249.27 |
| X-IC-1 | OCN~~~~~~NCO | 168.19 |
| X-IC-2 | (toluene 2,4-diisocyanate with additional NCO) | 174.16 |
| X-IC-3 | (m-xylylene diisocyanate) | 188.18 |
| X-IC-4 | (isophorone diisocyanate) | 222.28 |
| X-ME-1 | (methyl acrylate) | 86.09 |
| X-ME-2 | (dimethyl itaconate) | 158.16 |
| X-ME-3 | (dimethyl succinate) | 146.14 |
| X-ME-4 | (dimethyl phthalate) | 194.19 |
| X-ME-5 | (trimethyl citrate) | 234.2 |
| X-ME-6 | (trimethyl 1,3,5-benzenetricarboxylate) | 252.22 |
| X-ME-7 | (dimethyl isophthalate) | 194.19 |
| X-ME-8 | (dimethyl tartrate) | 178.14 |
| X-ME-9 | (methyl chloroacetate) | 108.53 |

Examples of suitable crosslinking agents are diacrylates and dimethacrylates (e.g., ethylene glycol diacrylate, propylene glycol diacrylate, butylene glycol diacrylate, ethylene glycol dimethacrylate, propylene glycol dimethacrylate, butylene glycol dimethacrylate, polyethyleneglycol dimethacrylate, polyethyleneglycol diacrylate), methylene bisacrylamide, methylene bismethacrylamide, ethylene bisacrylamide, ethylenebismethacrylamide, ethylidene bisacrylamide, divinyl benzene, bisphenol A dimethacrylate, bisphenol A diacrylate, diepoxides, dihalides, diisocyanates, diacyl chlorides, dianhydrides, and dimethyl esters.

Examples of preferred crosslinking agents include epichlorohydrin, 1,4 butanedioldiglycidyl ether, 1,2 ethanedioldiglycidyl ether, 1,3-dichloropropane, 1,2-dichloroethane, 1,3-dibromopropane, 1,2-dibromoethane, succinyl dichloride, dimethylsuccinate, toluene diisocyanate, acryloyl chloride, methyl acrylate, ethylene bisacrylamide, and pyromellitic dianhydride.

E. Polymerization

Polymerization can be achieved by methods known in the art, examples of which are illustrated in detail in the Examples disclosed herein. As described above, polymerization conditions may be manipulated in order to produce polymers with the desired characteristics.

The crosslinking reaction is carried out either in bulk solution (i.e. using the neat amine and neat crosslinker compounds) or in dispersed media. The crosslinking reaction leading to gel formation can be performed using a variety of processes; these processes fall into two categories:

i) homogeneous processes where the amine functional precursor (small molecule amine or high molecular weight polyamine) is soluble in the continuous phase, and where the gel, obtained by a crosslinking reaction, is recovered as a bulk gel or gel slurry in said continuous phase. Bulk gel process describes situation where the entirety of the solvent is trapped in the gel network forming a mass that is then comminuted in smaller particles using extrusion, grinding and related methods. When a bulk process is used, solvents are selected so that they co-dissolve the reactants and do not interfere with the amine crosslinking reaction. Suitable solvents include water, low boiling alcohols (methanol, ethanol, butanol), dimethylformamide, dimethylsulfoxide, acetone, methylethylketone, and the like. A gel slurry is typically obtained where the reaction medium viscosity is the low range and the shear rate high so that pieces of gel are produced that stay in suspension in a slurry form.

ii) heterogeneous processes, where the amine functional precursor (small molecule amine or high molecular weight polyamine) is made insoluble in the continuous phase so as to form dispersed droplets or particles, which then undergo a crosslinking reaction, forming bead or irregularly-shaped particles kept in suspension in said continuous phase.

Homogeneous processes can be impractical for crosslinked material with limited swelling ratios such as those contemplated in this invention: the level of crosslinking typical for the desired range of swelling ratio and pore size distribution usually induces very short gel time and high local viscosity, both of which are impractical in large scale manufacturing.

A preferred mode of synthesis for the present invention is to use heterogeneous processes. Such processes are also referred to as polymerization in dispersed media and include inverse suspension, direct suspension, precipitation polymerization, emulsion polymerization and microemulsion polymerization, reaction in aerosols, and the like. The continuous phase can be selected from apolar solvents such as toluene, benzene, hydrocarbon, halogenated solvents, supercritical carbon dioxide, and the like. With a direct suspension or emulsion process, water can be used, although salt brines are also useful to "salt out" the amine and crosslinker reagents in a droplet separate phase, as described in U.S. Pat. No. 5,414,068. The monomer precursors can be dispersed either neat or as a solution in the continuous phase. The amine and crosslinker are preferably introduced in two separate steps, wherein the amine is first dispersed as droplets, and subsequently the crosslinker is added to the reaction medium and migrates to the dispersed phase. The crosslinking reaction occurs within the droplet phase without causing any significant increase in viscosity in the dispersion. This has the advantage of dissipating the heat generated by the exothermic reaction while insuring good gel homogeneity within the beads. A preferred mode of synthesis comprises the steps of:

i) solubilizing the amine monomer or amine polymer in water
ii) neutralizing a fraction of the amine with an acid, such as HCl,
iii) dispersing said amine solution in a water immiscible solvent to form an emulsion
iv) adding the crosslinker to the emulsion in a staged addition
v) allowing the crosslinking reaction to proceed to completion
vi) removing the water by distillation
vii) isolating the beads by filtration
viii) washing and drying In this process the polymer particles are obtained as spherical beads, whose diameter is preferably controlled in the 5 to 500 microns range, preferably 25 to 250 microns. In some of these embodiments the beads have a mean diameter of less than 40 microns.

Thus, in one aspect, the invention provides a method of making an anion-binding polymer that binds a target anion, comprising combining an amine monomer with a crosslinker by a heterogeneous process, wherein the phosphate-binding polymer is characterized by at least two of the following features: a) a swelling ratio of less than about 5, or less than about 4.5, or less than about 4, or less than about 3; b) less than about 20% of the weight of the polymer accessible to non-interacting solutes of molecular weight greater than about twice the MW of the target anion, wherein said percentage is measured in a physiological medium, and c) an ion-binding interference for the target anion lower than about 60% when measured in a gastrointestinal simulant, relative to a non-interfering buffer. In some embodiments the amine monomer is a polyallylamine. In some embodiments the crosslinker is epichlorohydrin.

In another aspect the invention provides an anion-binding polymer that binds a target ion, wherein the polymer is produced by a process comprising crosslinking a polyallylamine by a heterogeneous process, and wherein said polymer is characterized by at least two of the following features: a) a swelling ratio of less than about 5, or less than about 4.5, or less than about 4, or less than about 3; b) less than about 20% of the weight of the polymer accessible to non-interacting solutes of molecular weight greater than about twice the MW of the target anion, wherein said percentage is measured in a physiological medium, and c) an ion-binding interference for the target anion lower than about 60% when measured in a gastrointestinal simulant, relative to a non-interfering buffer. In one embodiment, the polyallyamine is crosslinked by epichlorohydrin.

As discussed above, the crosslinker to amine mole ratios control the extent of gel material formed as well as its crosslinking density. Too low a ratio may lead to incomplete crosslinking and formation of soluble oligomers, while too high a ratio may produce an extremely tight network with little binding properties. The amine component can be either one or a combination of several amines, and the same applies to the crosslinker component. Optimization may be required for any new combination of amines and crosslinkers, since the functionality of either can influence the extent of gel formation and swelling characteristics. In some embodiments, e.g., embodiments of low molecular weight monomers crosslinked by crosslinkers with an Fb of 2, crosslinker to amine molar ratios (B/A) comprise between about 0.2 to about 10, preferably about 0.5 to about 5, and most preferably about 0.5 to about 2. These ratios may be adjusted, based on whether the amine monomer is a high molecular weight or low molecular weight monomer, and/or the Fb number of the crosslinker (see discussion and table above).

In some cases the polymers are crosslinked after polymerization. One method of obtaining such crosslinking involves reaction of the polymer with difunctional crosslinkers, such as epichlorohydrin, succinyl dichloride, the diglycidyl ether of bisphenol A, pyromellitic dianhydride, toluene diisocyanate, and ethylenediamine. A typical example is the reaction of poly(ethyleneimine) with epichlorohydrin. In this example the epichlorohydrin (1 to 100 parts) is added to a solution containing polyethyleneimine (100 parts) and heated to promote reaction. A typical example is the reaction of polyvicinalamine with epichlorohydrin. In this example the epichlorohydrin (1 to 200 parts) is added to a solution containing polyvicinalamine (100 parts) and heated to promote reaction. Other methods of inducing crosslinking on already polymerized materials include, but are not limited to, exposure to ionizing radiation, ultraviolet radiation, electron beams, radicals, and pyrolysis.

The crosslinking reaction is run in a batch or semi continuous mode. In the latter mode, either the amine or the crosslinker is added as the initial charge and the co-reactant is then metered up for a given period of time. In one embodiment, a soluble prepolymer is first prepared by adding the entire amine monomer component and then adding continuously a fraction of the crosslinker, forming a syrup. The syrup is then emulsified as droplets in an oil continuous phase and the remaining fraction of crosslinker is added to form crosslinked beads. When the crosslinker is an alkylhalide compound, a base can be used to scavenge the acid formed during the reaction. Inorganic or organic bases are suitable. NaOH is preferred. The base to crosslinker ratio is preferably between about 0.5 to about 2.

In some embodiments the polymers are subject to post-amination (post-reaction with 3-chloropropylamine). In this embodiment, a first reaction between an amine monomer and a crosslinker is carried out to form a gel, then the gel is post reacted with an aminoalkylhalide, where the amine alkyl groups are chemically attached to the gel through halide substitution by the amine functional gels.

All of the polymers described herein can be further crosslinked and imprinted with anion, e.g., phosphate. In one embodiment the target anion (e.g., phosphate or oxalate) is present during the polymerization and is then washed out when the crosslinking reaction is completed. The method is referred to as "imprinting" and tends to increase the chemical affinity of the gel towards the anion solute by creating "molded" pockets within the gel that have high binding recognition for a given anion. Examples of phosphate imprinted gels are described in e.g. Fujiwara et al, Analytical Sciences April 2000, vol. 16, 407, and in ACS symposium series 703, "Molecular and Ionic Recognition with Imprinted Polymers, Bartsch R A and Maeda M. Editors, 1998, Chap. 22, 315. Typically the anion is present at a mole ratio to amine (expressed as nitrogen atom) of between about 10% to about 100%, more preferably about 10% to about 60%, most preferably about 30% to about 50%. Most preferably, the anion is introduced in the acid form (e.g., phosphoric acid, oxalic acid) and the amine as the free base, so as to form, in situ, the ammonium/anion salt. Crosslinking is then carried out as described earlier by using the proper amount crosslinker to amine ratio in order to obtain the desired gel features in terms of swelling ratio, critical permeation volume, and binding interference. The gel immediately formed after crosslinking is then thoroughly washed in either highly acidic (e.g., pH<2) or highly basic (e.g., pH>12) medium to remove the imprinted anion, then further washed with neutral medium. All parameters being equal (e.g., amine to crosslinker ratio, monomer to solvent ratio) the imprinting method here described usually increases the binding capacity by a factor of 1.1, 1.3, or even 1.5.

III. Pharmaceutical Compositions

In one aspect the invention provides pharmaceutical compositions. In one embodiment, the pharmaceutical compositions are chewable tablets. In another embodiment, the pharmaceutical compositions are liquid formulations.

The pharmaceutical compositions of the present invention include compositions wherein the polymers of the invention, e.g., crosslinked amine polymers, are present in an effective amount, i.e., in an amount effective to achieve therapeutic and/or prophylactic benefit. The actual amount effective for a particular application will depend on the patient (e.g. age, weight) the condition being treated; and the route of administration. Determination of an effective amount is well within the capabilities of those skilled in the art, especially in light of the disclosure herein.

The effective amount for use in humans can be determined from animal models. For example, a dose for humans can be formulated to achieve circulating and/or gastrointestinal concentrations that have been found to be effective in animals.

The pharmaceutical compositions comprise the polymer, e.g., crosslinked amine polymers, one or more pharmaceutically acceptable carriers, diluents or excipients, and optionally additional therapeutic agents.

Pharmaceutical compositions for use in accordance with the present invention may be formulated in conventional manner using one or more physiologically acceptable carriers comprising excipients and auxiliaries which facilitate processing of the active compounds into preparations which can be used pharmaceutically. Proper formulation is dependent upon the route of administration chosen. Suitable techniques for preparing pharmaceutical compositions of the amines are well known in the art, e.g., Gennaro A R (ed), *Remington's Pharmaceutical Sciences,* 20th Edition, Lippincott, Williams and Wilkins, Baltimore Md. (2001), which is hereby incorporated in its entirety.

The present pharmaceutical compositions are generally prepared by known procedures using well known and readily available ingredients. In making the compositions of the present invention, the ion-binding polymer, e.g., a phosphate-binding polymer, may be present alone, may be admixed with a carrier, diluted by a carrier, or enclosed within a carrier which may be in the form of a capsule, sachet, paper or other container. When the carrier serves as a diluent, it may be a solid, semi-solid or liquid material which acts as a vehicle, excipient or medium for the polymer. Thus, the compositions can be in the form of tablets, pills, powders, lozenges, sachets, cachets, elixirs, suspensions, syrups, aerosols, (as a solid or in a liquid medium), soft or hard gelatin capsules, sterile packaged powders, and the like. Preferred formulations are chewable tablets and liquid formulations. Examples of carriers, excipients, and diluents that may be used in these formulations as well as others, include foods, drinks, lactose, dextrose, sucrose, sorbitol, mannitol, starches, gum acacia, alginates, tragacanth, gelatin, calcium silicate, microcrystalline cellulose, polyvinylpyrrolidone, cellulose, methyl cellulose, methylhydroxybenzoates, propylhydroxybenzoates, propylhydroxybenzoates, and talc.

In another aspect of the invention, the anion (e.g., phosphate) binding polymer is formulated as the free amine, free of counter-ions. Short term and long term studies have demonstrated that maintenance hemodialysis patients treated with Renagel (polyallylamine hydrochloride) have significantly lower serum bicarbonate levels than patients treated with calcium-containing phosphate binders (i.e. containing no chloride). It has been shown (Brezina B. et al, Kidney International, vo. 66, suppl. 90 (2004), 39-45) that SEVELAMER hydrochloride (Trade name of Renagel active pharmaceutical ingredient) induces an acid load that causes acidosis. Acidosis can have serious side effects for that category of patients. In another embodiment, the amine crosslinked polymer is a polyamine polymer where the chloride content of the polymer is less than about 40 mol % of the amine group content, more preferably less than about 20 mol % of the amine group content, and even more preferably less than about 5% of the amine group content. Most preferably, the polymer is substantially chloride-free.

A. Chewable Tablets

In some embodiments the polymers of the invention are provided as pharmaceutical compositions in the form of chewable tablets.

Patient compliance is recognized today as one of the main limiting factors for patients to adhere to recommendations in treating ion imbalance disorders, such as hyperphosphatemia. For example, in the treatment of hyperphosphatemia using current phosphate-binding polymers, such as RENAGEL recent surveys imply that patients have to take on average nine to ten 800 mg pills per day with 25% of the patient population taking even higher daily doses of twelve to fifteen pills. Renagel takes the form of swallowable tablets and is administered with amounts of fluid necessary to ingest the tablets, adding to the burden of ESRD patients who are under fluid restriction. Low patient compliance due to large daily doses stands out as a factor that clearly impacts acceptance of this class of drugs.

More easy-to-take pharmaceutical formulation would be desirable. Though drug delivery by chewable tablet would be highly advantageous in many cases, usage has been limited as formulators have encountered difficulties in achieving satisfactory sensory characteristics. When chewing a tablet the following sensory parameters are important: grittiness, tooth packing, chalkiness, mouthfeel, and overall palatability.

Current chewable tablets are mostly used in areas where significant amounts of active ingredients need to be administered and include over the counter products such as vitamins, antacids, laxatives and pain medications. Prescription chewable products include prenatal vitamins and chewable antibiotic and antiviral products that require large doses to be orally administered. Although often large, the geometry needs to be optimized to facilitate ease of chewing and "hardness" appropriate for mastication. Round bevel-edged shapes are common with height/diameter ratios around 0.3 to 0.4.

In addition to the active ingredient, the following types of excipients are commonly used: a sweetening agent to provide the necessary palatability, plus a binder where the former is inadequate in providing sufficient tablet hardness; a lubricant to minimize frictional effects at the die wall and facilitate tablet ejection; and, in some formulations a small amount of a disintegrant is added to facilitate mastication. In general excipient levels in currently-available chewable tablets are on the order of 3-5 fold of active ingredient(s) whereas sweetening agents make up the bulk of the inactive ingredients.

An important consideration in designing a chewable tablet containing an ion-binding polymer is the swelling ratio of the polymer. Because the invention provides polymers that are low-swelling, they may be used in chewable formulations without the unpleasant and sometimes dangerous side effects that accompany chewable tablets of higher-swelling polymers. One example of a high swelling material causing difficulties during oral administration potentially resulting in choking and blockage of the esophagus is Psyllium. Psyllium comes from the crushed seeds of the Plantago ovata plant, an herb native to parts of Asia, Mediterranean regions of Europe, and North Africa and is commonly used as a laxative in the US. Psyllium typically swells 35-50 times and has to be taken with plenty of fluids. Insufficient fluid uptake upon administration may cause the fiber to swell and result in choking or even rupture of the esophagus. Psyllium is contraindicated in patients that have dysphagia and/or a narrow esophagus.

The present invention provides chewable tablets that contain a polymer or polymers of the invention and one or more pharmaceutical excipients suitable for formulation of a chewable tablet. The polymer used in chewable tablets of the invention preferably has a swelling ratio while transiting the oral cavity and in the esophagus of less than about 5, preferably less than about 4, more preferably less than about 3, more preferably less than 2.5, and most preferably less than about 2. In some embodiments the polymer is an anion-binding polymer such as a phosphate- or oxalate binding polymer; in a preferred embodiment, the polymer is a phosphate-binding polymer. The tablet comprising the polymer, combined with suitable excipients, provides acceptable organoleptic properties such as mouthfeel, taste, and tooth packing, and at the same time does not pose a risk to obstruct the esophagus after chewing and contact with saliva.

In some aspects of the invention, the polymer(s) provide mechanical and thermal properties that are usually performed by excipients, thus decreasing the amount of such excipients required for the formulation. In some embodiments the active ingredient (e.g., polymer, preferably an anion-binding polymer) constitutes over about 30%, more preferably over about 40%, even more preferably over about 50%, and most preferably more than about 60% by weight of the chewable tablet, the remainder comprising suitable excipient(s). In some embodiments the polymer, e.g., an anion-binding polymer, comprises about 0.6 gm to about 2.0 gm of the total weight of the tablet, preferably about 0.8 gm to about 1.6 gm. In some embodiment the polymer, e.g., an anion-binding polymer, comprises more than about 0.8 gm of the tablet, preferably more than about 1.2 gm of the tablet, and most preferably more than about 1.6 gm of the tablet. The polymer is produced to have appropriate strength/friability and particle size to provide the same qualities for which excipients are often used, e.g., proper hardness, good mouth feel, compressibility, and the like. Particle size for polymers used in chewable tablets of the invention is less than about 80, 70, 60, 50, 40, 30, or 20 microns mean diameter. In preferred embodiments, the particle size is less than about 80, more preferably less than about 60, and most preferably less than about 40 microns.

Pharmaceutical excipients useful in the chewable tablets of the invention include a binder, such as microcrystalline cellulose, colloidal silica and combinations thereof (Prosolv 90), carbopol, providone and xanthan gum; a flavoring agent, such as sucrose, mannitol, xylitol, maltodextrin, fructose, or sorbitol; a lubricant, such as magnesium stearate, stearic acid, sodium stearyl fumurate and vegetable based fatty acids; and, optionally, a disintegrant, such as croscarmellose sodium, gellan gum, low-substituted hydroxypropyl ether of cellulose, sodium starch glycolate. Other additives may include plasticizers, pigments, talc, and the like. Such additives and other suitable ingredients are well-known in the art; see, e.g., Gennaro A R (ed), *Remington's Pharmaceutical Sciences,* 20th Edition.

In some embodiments the invention provides a pharmaceutical composition formulated as a chewable tablet, comprising a phosphate-binding polymer and a suitable excipient. In some embodiments the invention provides a pharmaceutical composition formulated as a chewable tablet, comprising a phosphate-binding polymer, a filler, and a lubricant. In some embodiments the invention provides a pharmaceutical composition formulated as a chewable tablet, comprising a phosphate-binding polymer, a filler, and a lubricant, wherein the filler is chosen from the group consisting of sucrose, mannitol, xylitol, maltodextrin, fructose, and sorbitol, and wherein the lubricant is a magnesium fatty acid salt, such as magnesium stearate.

The tablet may be of any size and shape compatible with chewability and mouth disintegration, preferably of a cylindrical shape, with a diameter of about 10 mm to about 40 mm and a height of about 2 mm to about 10 mm, most preferably a diameter of about 22 mm and a height of about 6 mm.

In one embodiment the polymer has a transition temperature greater than about 30° C., preferably greater than about 50° C.

In another embodiment, the polymer is pre-formulated with a high Tg/high melting point low molecular weight excipient such as mannitol, sorbose, sucrose in order to form a solid solution wherein the polymer and the excipient are intimately mixed. Method of mixing such as extrusion, spray-drying, chill drying, lyophilization, or wet granulation are useful. Indication of the level of mixing is given by known physical methods such as differential scanning calorimetry or dynamic mechanical analysis.

Methods of making chewable tablets containing pharmaceutical ingredients, including polymers, are known in the art. See, e.g., European Patent Application No. EP373852A2 and U.S. Pat. No. 6,475,510, and Remington's Pharmaceutical Sciences, which are hereby incorporated by reference in their entirety.

B. Liquid formulations

In some embodiments the polymers of the invention are provided as pharmaceutical compositions in the form of liquid formulations. In some embodiments the pharmaceutical composition contains an ion-binding polymer dispersed in a suitable liquid excipient. Suitable liquid excipients are known in the art; see, e.g., *Remington's Pharmaceutical Sciences*.

IV. Methods of treatment

In another aspect, the invention provides methods of treatment of ion imbalance disorders. The term "ion imbalance disorders" as used herein refers to conditions in which the level of an ion present in the body is abnormal. In one embodiment, the invention provides methods of treating a phosphate imbalance disorder. The term "phosphate imbalance disorder" as used herein refers to conditions in which the level of phosphorus present in the body is abnormal. One example of a phosphate imbalance disorder includes hyperphosphatemia. The term "hyperphosphatemia" as used herein refers to a condition in which the element phosphorus is present in the body at an elevated level. Typically, a patient is often diagnosed with hyperphosphatemia if the blood phosphate level is, for example, above about 4.5 milligrams per deciliter of blood and/or glomerular filtration rate is reduced to, for example, more than about 20%.

Thus, for example, the invention provides methods of removing an anion from an animal by administering an effective amount of a polymer of the invention to the animal. In some embodiments, the polymer is an anion-binding polymer where the polymer binds a target anion (e.g., phosphate or oxalate), and where the polymer is characterized by at least two of the following features: a) a swelling ratio of less than about 5; b) a gel pore volume distribution measured in a physiological medium characterized by a fraction of said pore volume accessible to non-interacting solutes, of molecular weight greater than about twice the MW of the target anion, of less than about 20% of the weight of the gel; and c) an ion-binding interference for the target anion lower than about 60% when measured in a gastrointestinal simulant, relative to a non-interfering buffer. In some embodiments, the target anion of the polymer is phosphate; in some embodiments the phosphate is removed from the gastrointestinal tract; in some embodiments the method of administration is oral. In some embodiments, the animal is afflicted with at least one disease selected from the group consisting of hyperphosphatemia, hypocalcemia, hyperthyroidism, depressed renal synthesis of calcitriol, tetany due to hypocalcemia, renal insufficiency, ectopic calcification in soft tissues, and ESRD. In some embodiments, the animal is a human. It will be appreciated that any polymer described herein may be useful in binding an anion in an animal and/or in treating conditions caused by an ion imbalance in an animal. In preferred embodiments, the polymer is a phosphate-binding polymer where the polymer is characterized by at least one of the following features: a) a swelling ratio of less than about 5, preferably less than about 2.5; b) a gel pore volume distribution measured in a physiological medium characterized by a fraction of said pore volume accessible to non-interacting solutes, of molecular weight greater than about 200, of less than about 20% of the weight of the gel; and c) an ion-binding interference for phosphate lower than about 60% when measured in a gastrointestinal simulant, relative to a non-interfering buffer. In some embodiments, the swelling ratio is less than about 2.8, or less than about 2.7, or less than about 2.6.

Other diseases that can be treated with the methods, compositions, and kits of the present invention include hypocalcemia, hyperparathyroidism, hungry bone syndrome, depressed renal synthesis of calcitriol, tetany due to hypocalcemia, renal insufficiency, and ectopic calcification in soft tissues including calcifications in joints, lungs, kidney, conjuctiva, and myocardial tissues. Also, the present invention can be used to treat ESRD and dialysis patients, including prophylactic treatment of any of the above.

Also, the polymers described herein can be used as an adjunct to other therapies e.g. those employing dietary control of phosphorus intake, dialysis inorganic metal salts and/or other polymer resins.

The compositions of the present invention are also useful in removing chloride, bicarbonate, iron ions, oxalate, and bile acids from the gastrointestinal tract. Polymers removing oxalate ions find use in the treatment of oxalate imbalance disorders, such as such as oxalosis or hyperoxaluria that increases the risk of kidney stone formation. Polymers removing chloride ions find use in treating acidosis, heartburn, acid reflux disease, sour stomach or gastritis, for example. In some embodiments, the compositions of the present invention are useful for removing fatty acids, bilirubin, and related compounds. Some embodiments may also bind and remove high molecular weight molecules like proteins, nucleic acids, vitamins or cell debris.

The present invention provides methods, pharmaceutical compositions, and kits for the treatment of animal. The term "animal" or "animal subject" as used herein includes humans as well as other mammals. One embodiment of the invention is a method of removing phosphate from the gastrointestinal tract of an animal by administering an effective amount of at least one of the crosslinked amine polymers described herein.

The term "treating" and its grammatical equivalents as used herein includes achieving a therapeutic benefit and/or a prophylactic benefit. By therapeutic benefit is meant eradication, amelioration, or prevention of the underlying disorder being treated. For example, in a hyperphosphatemia patient, therapeutic benefit includes eradication or amelioration of the underlying hyperphosphatemia. Also, a therapeutic benefit is achieved with the eradication, amelioration, or prevention of one or more of the physiological symptoms associated with the underlying disorder such that an improvement is observed in the patient, notwithstanding that the patient may still be afflicted with the underlying disorder. For example, administration of crosslinked amine polymers, described herein, to a patient suffering from renal insufficiency and/or hyperphosphatemia provides therapeutic benefit not only when the patient's serum phosphate level is decreased, but also when an improvement is observed in the patient with respect to other disorders that accompany renal failure and/or hyperphosphatemia like ectopic calcification and renal osteodystrophy. For prophylactic benefit, for example, the crosslinked amine polymers may be administered to a patient at risk of developing hyperphosphatemia or to a patient reporting one or more of the physiological symptoms of hyperphosphatemia, even though a diagnosis of hyperphosphatemia may not have been made. For example, the polymers of the invention may be administered to a patient with chronic kidney disease where hyperphosphatemia has not been diagnosed.

The dosages of the polymer, e.g., crosslinked amine polymers, in animals will depend on the disease being, treated, the route of administration, and the physical characteristics of the animal being treated. In some embodiments in which crosslinked amine polymers are used, the dosage levels of the crosslinked amine polymers for therapeutic and/or prophylactic uses can be from about 1 gm/day to about 30 gm/day. It is preferred that these polymers are administered along with meals. The polymers may be administered one time a day, two times a day, or three times a day. The preferred dosage range is from about 2 gm/day to about 20 gm/day and an even preferred dosage range is from about 3 gm/day to about 7 gm/day. The dose of the polymers described herein can be less than about 50 gm/day, preferably less than about 40 gm/day, even more preferably less than about 30 gm/day, even more preferred less than about 20 gm/day, and most preferred is less than about 10 gm/day.

Preferably, the ion-binding polymers, e.g., crosslinked amine polymers, used for therapeutic and/or prophylactic benefits can be administered alone or in the form of a pharmaceutical composition as described herein. For example, crosslinked amine polymers of the present invention may be co-administered with other active pharmaceutical agents depending on the condition being treated. Examples of pharmaceutical agents that maybe co-administered include, but are not limited to, proton pump inhibitors, calcimimetics (for example, cinacalcet), Vitamin D and analogs thereof, and phosphate binders. Examples of suitable phosphate binders include, but are not limited to, aluminum carbonate, calcium carbonate, calcium acetate (PhosLo), lanthanum carbonate (Fosrenol), and Renagel. This co-administration can include simultaneous administration of the two agents in the same dosage form, simultaneous administration in separate dosage forms, and separate administration. For example, for the treatment of hyperphosphatemia, the crosslinked amine polymers may be co-administered with calcium salts which are used to treat hypocalcemia resulting from hyperphosphatemia. The calcium salt and the polymer can be formulated together in the same dosage form and administered simultaneously. Alternatively, the calcium salt and the polymer can be simultaneously administered, wherein both the agent are presenting separate formulation. In another alternative, the calcium salt can be administered just followed by the polymer, or vice versa. In the separate administration protocol, the polymer and calcium salt may be administered a few minutes apart, or a few hours apart, or a few days apart.

The polymer can be administered by injection, topically, orally, transdermally, or rectally. Preferably, the polymer or the pharmaceutical composition comprising the polymer is administered orally. The oral form in which the polymer is administered can include powder, tablet, capsule, solution, or emulsion. The effective amount can be administered in a single dose or in a series of doses separated by appropriate time intervals, such as hours.

The invention also provides methods of removing anionic pollutants from wastewater by contacting the wastewater with an anion-binding polymer of the invention, where anionic pollutants, e.g., phosphate, are adsorbed to the polymer.

V. Kits

In still another aspect, the present invention provides kits for the treatment of anion imbalance disorders, e.g., for the treatment of phosphate imbalance disorders. These kits comprise a polymer or polymers described herein and instructions teaching the use of the kit according to the various methods and approaches described herein. Such kits may also include information, such as scientific literature references, package insert materials, clinical trial results, and/or summaries of these and the like, which indicate or establish the activities and/or advantages of the composition. Such information may be based on the results of various studies, for example, studies using experimental animals involving in vivo models and studies based on human clinical trials. Kits described herein can be provided, marketed and/or promoted to health providers, including physicians, nurses, pharmacists, formulary officials, and the like. Kits for cosmetic use may be provided, marketed and/or promoted directly to consumers.

All publications and patent applications mentioned in this specification are herein incorporated by reference to the same extent as if each individual publication or patent application was specifically and individually indicated to be incorporated by reference.

It will be apparent to one of ordinary skill in the art that many changes and modification can be made to the disclosures presented herein without departing from the spirit or scope of the appended claims.

EXAMPLES

Example 1

Phosphate Binding Measurement Protocols

In this Example various protocols for measuring the capacity of a polymer for binding of an anion (in this case, phosphate) are described.

Phosphate Binding Capacity Measurements in a Non Interfering Buffer

An aliquot of dried polymer of weight P(gr), was mixed under gentle agitation with a fixed volume, V(L), of the following buffer: 20 mM $H_3PO4$, 80 mM NaCl, 100 mM MES sodium salt (morpholinoethanesulfonic acid) and a pH of 6.5. When single binding measurements were made, the latter buffer was used. When multiple measurements were made, e.g., for the plotting of a binding isotherm, the phosphate concentration of the buffer was varied. The starting phosphate ion concentration is referred to as $P_{start}$(mM). The solution can be referred to as a non-interfering buffer as it contains no other competing solutes that compete with the phosphate ions for binding to the polymer resin. After resin equilibration, the solution was decanted by centrifugation and the supernatant analyzed for residual phosphate concentration by ionic chromatography, $P_{eq}$(mM). The binding capacity was calculated as $V*(P_{start}-P_{eq})/P$, expressed in mmol/gr as indicated in the tables for the corresponding polymers.

Binding Capacity in a Gastrointestinal Simulant

This procedure was designed to mimic the conditions of use of a phosphate binding polymer in a GI tract and measure the binding characteristics of the polymer for phosphate (target solute) in the presence of other metabolites (competing solutes). A liquid meal was artificially digested in the presence of pepsin and pancreatic juice to produce gastrointestinal (GI) simulant. The sequence of addition of enzymes and the pH profile were controlled so that the digestion process was simulated down to the jejunum level:

The following components were added one at a time in the following order: Powder Milk 291 g, Beneprotein 72.8 g, Dextrose 152 g, Polycose 156 g, NaCl 17.6 g to ~2.5 L of ddH$_2$O until they dissolved (they were stirred vigorously, but foaming was avoided). After the NaCl had dissolved 240 g of Corn Oil was added. Then the volume was brought up to 4 L with ddH$_2$O. The mixture was stirred vigorously for 2 hours. At this time pH was ~6.4. Then, 153 ml of 3M HCl was added drop wise to a final pH of 2.0 (~150 ml). The mixture was stirred for 15 minutes, after which time the pH rose to ~2.1. Then 800 ml of pepsin in 10 mM HCl was added to a final concentration of 1 mg/ml. The mixture was stirred at RT for 30 minutes, after which time the pH was ~2.3. Then 5 L of a stock solution of Pancreatin and Bile Salts in 100 mM NaHCO$_3$, pH 8.4 was added to a final concentration of 0.3 mg/ml Pancreatin and 2 mg/ml Bile Salts. The mixture was stirred for 120 minutes at room temperature, after which the pH was ~6.5. Meal mimic was stored at −80° C. for up to one month before use.

An aliquot of the GI simulant was centrifuged and the supernatant assayed for phosphate. The phosphate binding assay was like the one described above with non-interfering buffer, except that liquid of the GI simulant was used.

Binding Capacity in ex-vivo Aspirates

Using a tube placed in the lumen of the small intestine, healthy patients were given a meal of the same composition as the one prepared for the GI simulant described above and aliquots of chyme were then sampled.

Subjects were intubated with a double lumen polyvinyl tube with a mercury-weighted bag attached to the end of the tube to facilitate movement of the tube into the small intestine. Using fluoroscopy to direct placement, one aspiration aperture of the double lumen tube was located in the stomach, and the other aperture was at the Ligament of Treitz (in the upper jejunum).

After correct tube placement, 550 mL of the liquefied test meal (supplemented with a marker, polyethylene glycol (PEG) ~2 g/550 mL) was infused into the stomach through the gastric aperture at a rate of 22 mL per minute. It required approximately 25 minutes for the entire meal to reach the stomach, simulating the duration of time required to eat normal meals.

Jejunal chyme was aspirated from the tube whose lumen was located at the Ligament of Treitz. This fluid was collected continuously during 30 minute intervals for a two and a half hour period. This resulted in 5 specimens that were mixed, measured for volume, and lyophilized.

A phosphate binding assay was carried out on the ex-vivo aspirates. The phosphate binding procedure was like the one described above with non-interfering buffer, except that the ex-vivo aspirate liquid was used (after reconstitution of the freeze-dried material in the proper amount of de-ionized water). The phosphate binding capacities in the ex-vivo aspirate was calculated in the same way as in GI simulant experiments.

Example 2

Libraries of Crosslinked Polymers formed in a Bulk Solution Process and Measurement for Phosphate Binding Capacity Creation of Polymer Libraries The following five examples each comprise a library comprising up to 24 crosslinked polymers. Polymers were prepared in batch reactors arranged in a 4×6 array format. Each reactor had either a 350 microliters or a 3 ml volume, was magnetically stirred, and temperature-controlled. In a typical procedure, amine, crosslinkers, solvents and optionally base were dispensed robotically in each reactor, optionally under agitation. The reactors were then sealed and heated up to the indicated temperature for 15 hours. The reactor array was then dismounted and plugs of crosslinked polymers transferred in glass vials, ground, washed repeatedly with de-ionized water, and lyophilized. The five libraries are identified below in Table 3 along with the corresponding reaction conditions used in their creation.

TABLE 3

| Example | Library identification | Reaction temperature (° C.) | Reactor volume (microliters) |
|---|---|---|---|
| 1 | 100275 | 85 | 350 |
| 2 | 100277 | 60 | 350 |
| 3 | 100279 | 80 | 350 |
| 4 | 100353 | 80 | 350 |
| 5 | 100384 | 80 | 3000 |

Phosphate Binding Capacity Measurements in a Non Interfering Buffer

Binding capacities for phosphate ion were also determined for each of the polymers of the libraries. See Example 1 for procedure.

Results

Tables 4-8 provide materials and the quantities used in forming the polymers of each of the 5 libraries, along with the measured phosphate binding capacities in a non-interfering buffer for the polymers formed. Entries correspond to weight of chemicals used in each reaction well in mg, along with the phosphate binding capacity of the polymer gel obtained (blank indicates no crosslinked gel was formed in that particular reaction).

TABLE 4

Library: Plate3 (ID: 100275) Unit: mg

| Row | Col | water | B—SM-22-DA | X—Cl-3 | NaOH | DMSO | Phosphate binding (mmol/gr) |
|---|---|---|---|---|---|---|---|
| 1 | 1 | 128.51 | 67.74 | 51.63 | 9.14 | 0.00 | |
| 1 | 2 | 130.70 | 57.94 | 61.82 | 10.94 | 0.00 | |
| 1 | 3 | 132.33 | 50.61 | 69.43 | 12.29 | 0.00 | |
| 1 | 4 | 133.59 | 44.93 | 75.33 | 13.33 | 0.00 | 3.042 |
| 1 | 5 | 134.60 | 40.39 | 80.04 | 14.17 | 0.00 | 0 |

TABLE 4-continued

Library: Plate3 (ID: 100275) Unit: mg

| Row | Col | water | B—SM-22-DA | X—Cl-3 | NaOH | DMSO | Phosphate binding (mmol/gr) |
|---|---|---|---|---|---|---|---|
| 1 | 6 | 135.43 | 36.69 | 83.89 | 14.85 | 0.00 | 0 |
| 2 | 1 | 136.42 | 32.26 | 88.50 | 15.66 | 0.00 | 3.703 |
| 2 | 2 | 137.05 | 29.41 | 91.45 | 16.19 | 0.00 | 3.624 |
| 2 | 3 | 137.58 | 27.03 | 93.93 | 16.63 | 0.00 | 2.858 |
| 2 | 4 | 138.03 | 25.00 | 96.03 | 17.00 | 0.00 | 2.566 |
| 2 | 5 | 138.42 | 23.26 | 97.84 | 17.32 | 0.00 | 2.761 |
| 2 | 6 | 138.76 | 21.74 | 99.42 | 17.60 | 0.00 | 2.82 |
| 3 | 1 | 132.04 | 64.98 | 49.52 | 17.53 | 34.60 | |
| 3 | 2 | 134.77 | 55.13 | 58.82 | 20.82 | 47.26 | |
| 3 | 3 | 136.79 | 47.87 | 65.67 | 23.25 | 57.22 | |
| 3 | 4 | 138.34 | 42.30 | 70.93 | 25.11 | 65.27 | 3.087 |
| 3 | 5 | 139.57 | 37.90 | 75.09 | 26.58 | 71.91 | 2.946 |
| 3 | 6 | 140.56 | 34.32 | 78.47 | 27.78 | 77.48 | 2.535 |
| 4 | 1 | 141.75 | 30.06 | 82.48 | 29.20 | 79.73 | 2.674 |
| 4 | 2 | 142.50 | 27.35 | 85.04 | 30.11 | 90.45 | 3.038 |
| 4 | 3 | 143.13 | 25.09 | 87.18 | 30.86 | 97.98 | 2.895 |
| 4 | 4 | 143.66 | 23.17 | 88.99 | 31.50 | 103.56 | 2.571 |
| 4 | 5 | 144.12 | 21.52 | 90.54 | 32.05 | 107.86 | 2.636 |
| 4 | 6 | 0.00 | 0.00 | 0.00 | 0.00 | 0.00 | 5.374 |

TABLE 5

Library: Plate1 (ID: 100277) Unit: mg

| Row | Col | water | B—SM-20-TeA | X-EP-1 | X-EP-4 | | Phosphate binding (mmol/gr) |
|---|---|---|---|---|---|---|---|
| 1 | 1 | 123.69 | 110.75 | 12.95 | 0.00 | DMF | |
| 1 | 2 | 124.02 | 107.66 | 16.36 | 0.00 | 0.00 | |
| 1 | 3 | 124.33 | 104.74 | 19.59 | 0.00 | 0.00 | |
| 1 | 4 | 124.63 | 101.98 | 22.65 | 0.00 | 0.00 | |
| 1 | 5 | 124.91 | 99.35 | 25.55 | 0.00 | 0.00 | 4.183 |
| 1 | 6 | 125.17 | 96.86 | 28.31 | 0.00 | 0.00 | 4.237 |
| 2 | 1 | 125.59 | 92.98 | 32.61 | 0.00 | 0.00 | 4.631 |
| 2 | 2 | 125.89 | 90.08 | 35.81 | 0.00 | 0.00 | 4.594 |
| 2 | 3 | 126.18 | 87.37 | 38.81 | 0.00 | 0.00 | 4.667 |
| 2 | 4 | 126.45 | 84.81 | 41.64 | 0.00 | 0.00 | 4.586 |
| 2 | 5 | 126.71 | 82.40 | 44.31 | 0.00 | 0.00 | 4.535 |
| 2 | 6 | 126.95 | 80.12 | 46.83 | 0.00 | 0.00 | 4.311 |
| 3 | 1 | 0.00 | 181.12 | 0.00 | 34.60 | 0.00 | |
| 3 | 2 | 0.00 | 159.58 | 0.00 | 47.26 | 104.77 | |
| 3 | 3 | 0.00 | 142.63 | 0.00 | 57.22 | 118.23 | 3.112 |
| 3 | 4 | 0.00 | 128.93 | 0.00 | 65.27 | 128.56 | 2.991 |
| 3 | 5 | 0.00 | 117.63 | 0.00 | 71.91 | 136.73 | 2.798 |
| 3 | 6 | 0.00 | 108.15 | 0.00 | 77.48 | 143.35 | 3.271 |
| 4 | 1 | 0.00 | 104.33 | 0.00 | 79.73 | 148.83 | 3.258 |
| 4 | 2 | 0.00 | 86.08 | 0.00 | 90.45 | 156.12 | 3.062 |
| 4 | 3 | 0.00 | 73.27 | 0.00 | 97.98 | 160.76 | 2.176 |
| 4 | 4 | 0.00 | 63.77 | 0.00 | 103.56 | 164.62 | 2.228 |
| 4 | 5 | 0.00 | 56.46 | 0.00 | 107.86 | 167.88 | 2.407 |
| 4 | 6 | 0.00 | 0.00 | 0.00 | 0.00 | 170.67 | 5.224 |
| 4 | 6 | 0.00 | 0.00 | 0.00 | 0.00 | 0.00 | |

TABLE 6

Library: Plate3 (ID: 100279) Unit: mg

| Row | Col | water | B—SM-20-TeA | X—Cl-3 | X—Cl-2 | Phosphate binding (mmol/gr) |
|---|---|---|---|---|---|---|
| 1 | 1 | 123.95 | 108.47 | 15.49 | 0.00 | |
| 1 | 2 | 124.34 | 104.88 | 19.47 | 0.00 | |
| 1 | 3 | 124.70 | 101.51 | 23.19 | 0.00 | |
| 1 | 4 | 125.04 | 98.36 | 26.68 | 0.00 | |
| 1 | 5 | 125.36 | 95.40 | 29.97 | 0.00 | 3.958 |
| 1 | 6 | 125.66 | 92.61 | 33.06 | 0.00 | 4.309 |
| 2 | 1 | 126.13 | 88.30 | 37.82 | 0.00 | 4.417 |
| 2 | 2 | 126.47 | 85.14 | 41.33 | 0.00 | 4.424 |
| 2 | 3 | 126.78 | 82.19 | 44.59 | 0.00 | 4.392 |
| 2 | 4 | 127.08 | 79.44 | 47.64 | 0.00 | 4.407 |

TABLE 6-continued

Library: Plate3 (ID: 100279) Unit: mg

| Row | Col | water | B—SM-20-TeA | X—Cl-3 | X—Cl-2 | Phosphate binding (mmol/gr) |
|---|---|---|---|---|---|---|
| 2 | 5 | 127.36 | 76.87 | 50.49 | 0.00 | 4.14 |
| 2 | 6 | 127.62 | 74.46 | 53.16 | 0.00 | 4.314 |
| 3 | 1 | 0.00 | 118.41 | 0.00 | 26.19 | |
| 3 | 2 | 0.00 | 102.78 | 0.00 | 29.56 | |
| 3 | 3 | 0.00 | 90.80 | 0.00 | 32.14 | |
| 3 | 4 | 0.00 | 81.32 | 0.00 | 34.18 | |
| 3 | 5 | 0.00 | 73.64 | 0.00 | 35.84 | |
| 3 | 6 | 0.00 | 67.28 | 0.00 | 37.21 | 2.237 |
| 4 | 1 | 0.00 | 58.81 | 0.00 | 39.03 | 2.403 |
| 4 | 2 | 0.00 | 53.43 | 0.00 | 40.19 | 2.704 |
| 4 | 3 | 0.00 | 48.96 | 0.00 | 41.15 | 2.614 |
| 4 | 4 | 0.00 | 45.17 | 0.00 | 41.97 | 1.714 |
| 4 | 5 | 0.00 | 41.93 | 0.00 | 42.67 | 2.294 |
| 4 | 6 | 0.00 | 0.00 | 0.00 | 0.00 | 5.295 |

TABLE 7

Library: Plate1 (ID: 100353) Unit: mg

| Row | Col | B—SM-20-TeA | B—SM-22-DA | X—Cl-3 | NaOH | Phosphate binding (mmol/gr) |
|---|---|---|---|---|---|---|
| 1 | 1 | 142.77 | 11.14 | 33.97 | 24.05 | |
| 1 | 2 | 117.71 | 9.19 | 44.82 | 31.73 | |
| 1 | 3 | 100.13 | 7.82 | 52.42 | 37.12 | 5.838 |
| 1 | 4 | 87.12 | 6.80 | 58.05 | 41.10 | 5.38 |
| 1 | 5 | 77.10 | 6.02 | 62.39 | 44.17 | 5.549 |
| 1 | 6 | 69.15 | 5.40 | 65.83 | 46.61 | 5.826 |
| 2 | 1 | 64.71 | 5.05 | 67.75 | 47.97 | 5.452 |
| 2 | 2 | 57.99 | 4.53 | 70.66 | 50.03 | 3.358 |
| 2 | 3 | 52.54 | 4.10 | 73.01 | 51.70 | 3.45 |
| 2 | 4 | 48.02 | 3.75 | 74.97 | 53.08 | 4.27 |
| 2 | 5 | 44.22 | 3.45 | 76.61 | 54.24 | 3.469 |
| 2 | 6 | 40.98 | 3.20 | 78.02 | 55.24 | 4.058 |
| 3 | 1 | 111.71 | 26.16 | 39.87 | 28.23 | |
| 3 | 2 | 89.37 | 20.93 | 51.04 | 36.14 | |
| 3 | 3 | 74.48 | 17.44 | 58.49 | 41.41 | 5.154 |
| 3 | 4 | 63.85 | 14.95 | 63.81 | 45.18 | 5.784 |
| 3 | 5 | 55.87 | 13.08 | 67.80 | 48.01 | 5.596 |
| 3 | 6 | 49.66 | 11.63 | 70.91 | 50.20 | 5.287 |
| 4 | 1 | 46.24 | 10.83 | 72.62 | 51.42 | 5.261 |
| 4 | 2 | 41.13 | 9.63 | 75.17 | 53.23 | 4.743 |
| 4 | 3 | 37.04 | 8.67 | 77.22 | 54.67 | 4.076 |
| 4 | 4 | 33.69 | 7.89 | 78.90 | 55.86 | 3.924 |
| 4 | 5 | 30.90 | 7.24 | 80.29 | 56.85 | 2.896 |
| 4 | 6 | 0.00 | 0.00 | 0.00 | 0.00 | 5.287 |

TABLE 8

Library: Plate1 (ID: 100384) Unit: mg

| Row | Col | X—Cl-3 | B—SM-22-DA | water | NaOH | Phosphate binding (mmol/gr) |
|---|---|---|---|---|---|---|
| 1 | 1 | 643.88 | 422.44 | 1752.36 | 227.94 | |
| 1 | 2 | 692.40 | 378.56 | 1743.80 | 245.12 | 4.362 |
| 1 | 3 | 731.79 | 342.94 | 1736.85 | 259.06 | 4.09 |
| 1 | 4 | 764.40 | 313.44 | 1731.10 | 270.61 | 3.198 |
| 1 | 5 | 791.85 | 288.62 | 1726.26 | 280.33 | 2.951 |
| 1 | 6 | 815.27 | 267.44 | 1722.12 | 288.62 | 2.005 |
| 2 | 1 | 643.88 | 422.44 | 1752.36 | 227.94 | |
| 2 | 2 | 692.40 | 378.56 | 1743.80 | 245.12 | |
| 2 | 3 | 731.79 | 342.94 | 1736.85 | 259.06 | |
| 2 | 4 | 764.40 | 313.44 | 1731.10 | 270.61 | 4.794 |
| 2 | 5 | 791.85 | 288.62 | 1726.26 | 280.33 | |
| 2 | 6 | 815.27 | 267.44 | 1722.12 | 288.62 | 4.332 |
| 3 | 1 | 643.88 | 422.44 | 1752.36 | 227.94 | |
| 3 | 2 | 692.40 | 378.56 | 1743.80 | 245.12 | |
| 3 | 3 | 731.79 | 342.94 | 1736.85 | 259.06 | |
| 3 | 4 | 764.40 | 313.44 | 1731.10 | 270.61 | 4.511 |
| 3 | 5 | 791.85 | 288.62 | 1726.26 | 280.33 | 5.086 |
| 3 | 6 | 815.27 | 267.44 | 1722.12 | 288.62 | 4.61 |
| 4 | 1 | 643.88 | 422.44 | 1752.36 | 227.94 | |
| 4 | 2 | 692.40 | 378.56 | 1743.80 | 245.12 | |
| 4 | 3 | 731.79 | 342.94 | 1736.85 | 259.06 | |
| 4 | 4 | 764.40 | 313.44 | 1731.10 | 270.61 | |
| 4 | 5 | 791.85 | 288.62 | 1726.26 | 280.33 | 4.816 |
| 4 | 6 | 0.00 | 0.00 | 0.00 | 0.00 | 5.17 |

Example 3

Synthesis of 1,3-Diaminopropane/epichlorohydrin Crosslinked Beads formed in a Suspension Process A 3-liter reaction vessel was used, comprising a three necked round bottom flask with four side baffles. The reaction flask was equipped with an oil heating bath, cold-water reflux condenser, and mechanical stirrer with a 3 inch propeller. To this reaction vessel was introduced a solution of 1,3-diaminopropane (90.2 g, 1.21 mole) dissolved in 90.2 g of water, surfactant (branched dodecylbenzene sulfonic acid sodium salt, 6.4 g dissolved in 100 g of water) and 1 Kg of toluene. This initial charge was agitated to 600 rpm for 2 minutes and then lowered to 300 rpm for 10 minutes before the epichlorohydrin was added. The 300 rpm speed was maintained through out the remainder of the experiment. The solution was heated to 80° C. and also maintained at this temperature through out the experiment.

In a separate vessel, a 40 mass % solution of epichlorohydrin in toluene was prepared. Using a syringe pump, 1.2 equivalents of epichlorohydrin (134.7 g, (1.45 mole)) were added to the initial charge reaction vessel over a 3 hour period. The reaction was continued for an additional 2 hours before adding 0.75 equivalents of sodium hydroxide (36.5 g (0.91 mole)) in a 40 weight % solution. The sodium hydroxide solution was added to the reaction via a syringe pump over a 2.5 hour period. The reaction was maintained at 80° C. for a further 8 hours.

After this time, beads that formed were purified by removing the toluene, washing with 1000 ml of acetone, followed by methanol, a 20% solution of NaOH (to remove the surfactant), and then twice more with deionized water. The beads were freeze dried for 3 days to give a fine white powder weighing at 160 g (92% yield) and having a mean diameter of 93 μm.

Example 4

Synthesis of 1,3-Diaminopropane/1,3-Dichloropropane Crosslinked Polymer

Using water as solvent, 1000 mg of B-SM-22-DA was mixed with 1524 mg of X—Cl-3 and 2524 mg of water in a 20 mL scintillation vial. The reaction was subjected to magnetic stirring and maintained at a temperature of 80° C. overnight, followed by a temperature of 90° C. for two additional hours. A 34 wt. % of reaction mixture (1716 mg) was purified by 3 washing in water/centrifugation steps and gave 144.7 mg of powder of the polymer of the present example.

Example 5

Synthesis of
1,3-Diaminopropane/1,3-Dichloropropane
Crosslinked Polymer

Using water as a solvent, 2000 mg of B-SM-22-DA was mixed with 3048 mg of X—Cl-3 and 5048 mg of water in a 20 mL scintillation vial. The reaction was subjected to magnetic stirring and maintained at a temperature of 80° C. overnight. 3597 mg of NaOH solution at 30 wt. % in water was added after 3 hours of reaction to scavenge the acid formed during the reaction as the crosslinker used was an alkylhalide. A 20.3 wt. % of reaction mixture (2773.5 mg) was purified by 3 washing in water/centrifugation steps and gave 591.3 mg of powder of the polymer of the present example.

Example 6

Synthesis of Crosslinked Beads Prepared with
1,3-Diaminopropane/1,3-Dichloropropane using a
Prepolymer Approach Preparation of Pre-Polymer The reaction vessel used was a 250 mL, two necked round bottom flask, equipped with a cold-water reflux condenser, magnetic stirrer, and run over an argon atmosphere. To this reaction vessel is introduced a solution of 1,3-diaminopropane (31.15 g, 0.42 mole) dissolved in 30.15 g of water. This initial charge is agitated to 300 rpm. The solution was heated to 80° C. and maintained at this temperature through out the experiment. Using a syringe pump, 1 equivalent (47.47 g, 40.0 mL, 0.42 mol) of 1,3 dichloropropane (Aldrich 99%) was added over a 2-hour period. The reaction was continued for an additional 2 hours before adding 10 mole % (with respect to 1,3-diaminopropane) of sodium hydroxide (1.68 g (0.042 mole) of NaOH and made up to a 40 weight % solution of water). The sodium hydroxide solution was added to the reaction via pipette over a 2 minute period. The reaction was maintained at 80° C. for a further 4 hours. The solution at 80° C. is viscous and upon cooling to 25° C. becomes a solid plug that is readily soluble in water.

Purification

To the solid plug water is added, washing with 200 ml of water and 200 mL of MeOH. This is then added to a 1 L beaker that contains a 50/50 solution of MeOH/Isopropyl alcohol. The white polymer precipitates. After placing the suspension into a centrifuge, the supernatant liquid is removed. This process is repeated using isopropyl alcohol a further 2 times. The white precipitate is then dried under reduced pressure at room temperature to remove the isopropyl alcohol. Weight of polymer isolated: Mn (GPC relative to polyethylenimine standard) ~600.

Synthesis Crosslinked Particles

The white pre-polymer (8.7 g) was placed into a flask with 1.3 g of branched dodecylbenzene sulfonic acid sodium salt (30 wgt % solution in water) and 34.8 g of toluene. This gave a 20 weight % solution of polymer suspended in toluene. The polymer was ground to micron sized particles with a mechanical grinder (Brand: IKA. Model: Ultra-Turax T8). 2.2 g of the resulting suspension was loaded into a 10 mL reaction flask equipped with a heater, a mechanical stirrer, and a syringe pump. The reaction flask was charged with an additional 3779 mg of toluene. The flask was heated to 80° C. and the stirrer was turned on (500 RPM). After 3 hours of stirring at this temperature, 112.2 mg (0.0012 mole) of epichlorohydrin was added over a 1.5-hour period. The reaction was allowed to proceed a further 2 hours before the addition of 224.4 mg (0.0056 mol) of sodium hydroxide (in a 40 weight % solution of water), which was delivered over a 2 hour period. The reaction was allowed to cool to room temperature and the stirring was stopped. The beads were purified by removing the toluene, washing with methanol, and then a 20% solution of NaOH (to remove the surfactant) and twice more with deionized water. The beads were freeze dried for 3 days to give a fine white powder. The binding capacity measured in a non interfering buffer was 3.85 mmol/gr.

Example 7

Synthesis and Isolation of Low Molecular Weight
Polymer (Prepolymer) Prepared with
1,3-Diaminopropane/1,3-dichloropropane 1

Abbreviations used in the following examples:
Epichlorohydrin: ECH
N,N,N',N'-tetrakis(3-aminopropyl)1,4 diaminobutane: BTA
BC: binding capacity In this Example, the effect of varying the ratio of monomer (in this case, a prepolymer) to solvent in the reaction mix on binding capacity and swelling ratio was shown. This Example describes a process involving two parts: first, the synthesis of a soluble prepolymer adduct from 1,3 diaminopropane and 1,3dichloropropane, and second, the preparation of insoluble beads by further crosslinking of the prepolymer by ECH. The second reaction consisted of an inverse suspension process wherein the water to prepolymer ratio was varied. The impact of this variation on binding performance and swelling was evaluated.

Synthesis of Prepolymer

Step 1 (Preparation of pre-polymer): The reaction vessel used was a 250 mL, two necked round bottom flask, equipped with a cold-water reflux condenser, magnetic stirrer and run over an argon atmosphere. To this reaction vessel was introduced a solution of 1,3-diaminopropane (31.15 g, 0.42 mole) dissolved in 30.15 g of water. This initial charge was agitated to 300 rpm. The solution was heated to 80° C. and maintained at this temperature through out the experiment. Using a syringe pump, 1 equivalent (47.47 g, 40.0 mL, 0.42 mol) of 1,3 dichloropropane (Aldrich 99%) was added over a 2 hour period. The reaction was continued for an additional 2 hours before adding 10 mole % (with respect to 1,3-diaminopropane) of sodium hydroxide (1.68 g (0.042 mole) of NaOH and made up to a 40 weight % solution of water). The sodium hydroxide solution was added to the reaction via pipette over a 2 minute period. The reaction was maintained at 80° C. for a further 4 hours. The solution at 80° C. was viscous and upon cooling to 25° C. became a solid plug that was readily soluble in water.

Step 2 (Purification): Water was added to the solid plug, washing with 200 ml of water and 200 mL of MeOH. This was then added to a 1 L beaker that contains a 50/50 solution of MeOH/Isopropyl alcohol. The white polymer precipitated. After centrifugation, the supernatant liquid was removed. This process was repeated using isopropyl alcohol a further 2 times. The white precipitate was then dried under reduced pressure at room temperature to remove the isopropyl alcohol. Molecular weight of polymer isolated: Mn (GPC relative to polyethyleneimine standard) ~600.

Synthesis of Micron Sized, Crosslinked Particles Prepared with 1,3-Diaminopropane/1,3 dichloropropane Pre-Polymer in a Semi-Continuous 24 Well, Parallel Polymerization Reactor.

The white pre-polymer 1 (8.7 g) was placed into a flask with 1.3 g of branched dodecylbenzene sulfonic acid sodium salt (30 wt % solution in water) and 34.8 g of toluene. This gave a 20 weight % solution of polymer suspended in toluene. The emulsion was ground to micron sized droplets with a high shear homogenizer (Brand: IKA. Model: Ultra-Turax T8). 2.2 g of the resulting emulsion was loaded into 24 of the 10 mL reaction flasks of the reactor which was equipped with a heater, a mechanical stirrer and a syringe pump. Into each reaction flask was charged an additional 3779 mg of toluene. The flasks were heated to 80° C. and the stirrer was turned on (500 RPM). Water was loaded into the tubes in an amount necessary to produce various ratios of prepolymer to water. After 3 hours of stirring at this temperature, the desired amount of epichlorohydrin (in this Example, epichlorohydrin was added to an amount equal to 20% of the dry weight of the pre-polymer) was added over a 1.5 hour period. The reaction was allowed to proceed a further 2 hours before the addition of 224.4 mg, (0.0056 mol) of sodium hydroxide (in a 40 weight % solution of water), which was delivered over a 2 hour period. The reaction was allowed to cool to room temperature and the stirring was stopped. The beads were purified by removing the toluene, washing with methanol and then a 20% solution of NaOH (to remove the surfactant) and then with HCl to protonate the bead. The beads were then washed twice with deionized water to remove excess HCl. The beads were freeze dried for 3 days to give a fine white powder.

The polymer beads thus synthesized were analyzed for binding capacity (BC) in non-interfering buffer and in a GI simulant, and for swelling ratio. The results are summarized in Table 9.

TABLE 9

1,3 diamino propane/1,3 dichloropropane/ECH gel beads. Effect of the monomer to water ratio on Binding Capacity and Swelling

| Monomer to water ratio | BC (mmol/gr) Non Interfering | BC (mmol. gr) GI simulant | Swelling (g of H20/g of polymer) |
|---|---|---|---|
| 1.67 | 3.85 | 1.54 | 2.92 |
| 1.42 | 3.68 | 1.43 | 3.34 |
| 1.25 | 3.61 | 1.34 | 3.50 |
| 1.11 | 3.55 | 1.34 | 3.70 |
| 0.83 | 3.31 | 1.16 | 5.22 |
| 0.55 | 2.90 | 0.91 | 14.00 |

These results show that the binding capacities in both non-interfering buffer and in GI simulant increase as the monomer to water ratio increases, while the swelling ratio decreases and reaches to the desired range.

Example 8

Synthesis of Micron Sized, Crosslinked Particles from Ground BTA/ECH Bulk Gel using a 24 Well Parallel Polymerization Reactor In this Example the effect of varying the amount of crosslinker relative to monomer on binding capacity and swelling ratio was shown.

The following stock solution was prepared: 2 molar equivalents of concentrated HCl was added to 1 molar equivalent of BTA over a 2 hour period. Water was then added to the solution such that the resulting solution achieved the following weight % composition: BTA 45 weight % HCl 10 weight %, water 45 weight %. Into each flask of a 24 well reactor using 5 mL flasks was placed 0.6 g of the prepared stock solution. The desired amount of epichlorohydrin to achieve the monomer:crosslinker ratio to be tested was added to each vial. The reactor was heated to 80° C. for 9 hours. The reactor was allowed to cool. To each vial was added water to swell the resulting gel. The gel was then ground to micron sized particles with a high shear homogenizer (Brand: IKA. Model: Ultra-Turax T8). The particles were purified by removing the water, washing with methanol and then a 20% solution of NaOH and then with HCl to protonate the amine functionalized particle. The particles were then washed twice with deionized water to remove excess HCl. The particles were freeze dried for 3 days to give a fine white powder.

The results of binding capacity and swelling studies are summarized in Table 10.

TABLE 10

BTA/ECH gel: Data on Swelling and Binding Capacities against crosslinker content. Bulk Gels (Monomer to water ratio is 75 wt % Bow-Tie (2HCl in water). Monomer to water ratios ranges from 3.5 (ECH:BTA = 0.85) to 4.8 (ECH:BTA = 6.4)

| ECH:BTA Mole ratio | BC (mmol/gr) Non interfering | BC (mmol. gr) GI simulant | Swelling ratio (gr. Water/ gr. Polymer) |
|---|---|---|---|
| 0.70 | 0.00 | 0.00 | |
| 0.85 | 2.23 | 0.35 | |
| 1.00 | 2.46 | 0.49 | 16.68 |
| 1.15 | 2.57 | 0.49 | 10.98 |
| 1.30 | 2.84 | 0.58 | 6.15 |
| 1.45 | 2.91 | 0.65 | 4.69 |
| 1.60 | 2.91 | 0.77 | 3.85 |
| 1.79 | 2.88 | 0.85 | 3.13 |
| 1.98 | 0.00 | 0.98 | 2.77 |
| 2.00 | 2.46 | 1.00 | 2.55 |
| 2.00 | 2.46 | 1.00 | 2.55 |
| 2.16 | 2.73 | 0.99 | 2.46 |
| 2.35 | 2.67 | 0.96 | 2.20 |
| 2.40 | 2.17 | 0.93 | 1.97 |
| 2.40 | 2.17 | 0.93 | 1.97 |
| 2.80 | 1.86 | 0.82 | 1.81 |
| 2.80 | 1.86 | 0.82 | 1.81 |
| 3.20 | 1.63 | 0.73 | 1.84 |
| 3.20 | 1.63 | 0.73 | 1.84 |
| 3.60 | 1.28 | 0.64 | 1.57 |
| 3.60 | 1.28 | 0.64 | 1.57 |
| 4.00 | 1.09 | 0.58 | 1.57 |
| 4.00 | 1.09 | 0.58 | 1.57 |
| 4.40 | 0.88 | 0.45 | 2.03 |
| 4.40 | 0.88 | 0.45 | 2.03 |
| 4.90 | 0.42 | 0.35 | 1.47 |
| 4.90 | 0.42 | 0.35 | 1.47 |
| 5.40 | 0.42 | 0.28 | 1.50 |
| 5.40 | 0.42 | 0.28 | 1.50 |
| 5.90 | 0.07 | 0.27 | 1.55 |
| 5.90 | 0.07 | 0.27 | 1.55 |
| 6.40 | 0.06 | 0.22 | 1.55 |
| 6.40 | 0.06 | 0.22 | 1.55 |

These data show that the binding capacity in the GI simulant goes through a maximum as the crosslinker to amine ratio is varied. In this particular system the optimum binding capacity in the GI stimulant is observed at a crosslinker ratio of 1.8 to 2.8, corresponding to a NC value of 3.6 to 5.6 respectively. Within that range of crosslinking the swelling ratio is minimal. Similar tests routinely may be carried out for other monomers and crosslinkers using this polymerization protocol to determine the ratio that gives the desired results for the particular use to which the polymer will be put.

Example 9

Synthesis of Micron Sized, Crosslinked BTA/ECH Beads Via Inverse Suspension

The following stock solution was prepared: 2 molar equivalents of concentrated HCl was added to 1 molar equivalent of BTA over a 2 hour period. Water and surfactant (branched dodecylbenzene sulfonic acid sodium salt, 30 weight % in water) was then added to the solution such that the resulting solution achieved the following weight % composition: BTA 41.8 weight %, HCl 9.4 weight %, water 41.1 weight %, surfactant (30 weight % in water) 7.7 weight %.

The reaction vessel used was a 0.25 liter, three necked round bottom flask with four side baffles, equipped with an oil heating bath, cold-water reflux condenser and mechanical stirrer with a 1 inch propeller. To this reaction vessel was introduced 25 g of the prepared stock solution and 75 g of toluene.

Into a separate vessel, a 40 mass % solution of epichlorohydrin in toluene was prepared. Using a syringe pump, the desired amount of ECH was added over a 90 minute period. The reaction was continued for an additional 2 hours before beginning a dehydration using a dean stark apparatus. The reaction end point was reached when all the water from the system had been removed. The beads were purified by removing the toluene, washing with methanol and then a 20% solution of NaOH (to remove the surfactant) and then with HCl to protonate the bead. The beads were then washed twice with deionized water to remove excess HCl. The beads were freeze dried for 3 days to give a fine white powder.

The results of binding capacity and swelling studies are summarized in Table 11.

TABLE 11

BTA/ECH gel beads: Swelling and Binding Capacities against crosslinker content

| ECH:BTA Mole ratio | BC (mmol/gr) Non interfering | BC (mmol/gr) Digested meal | Swelling ratio (gr. Water/ gr. Polymer) |
| --- | --- | --- | --- |
| 1.00 | 2.50 | 0.58 | 25.29 |
| 1.00 | 2.77 | 0.55 | 13.01 |
| 1.25 | 2.97 | 0.65 | 7.69 |
| 1.25 | 3.03 | 0.61 | 7.07 |
| 1.50 | 3.13 | 0.71 | 4.41 |
| 1.50 | 3.14 | 0.69 | 3.99 |
| 1.75 | 3.13 | 0.78 | 3.06 |
| 1.75 | 3.10 | 0.87 | 3.41 |
| 2.00 | 3.07 | 0.99 | 3.13 |
| 2.00 | 2.80 | 1.00 | 2.82 |
| 2.00 | 2.82 | 0.73 | 3.17 |
| 2.50 | 2.76 | 1.03 | 2.48 |
| 3.00 | 2.56 | 0.82 | 2.40 |
| 3.50 | 0.00 | 0.71 | 2.28 |
| 3.00 | 2.32 | 0.70 | 2.25 |
| 3.00 | 2.61 | 0.80 | 2.03 |
| 3.50 | 2.81 | 0.59 | 1.85 |
| 4.00 | 0.00 | 0.58 | 1.99 |
| 4.00 | 2.19 | 0.77 | 1.93 |
| 4.50 | 2.11 | 0.30 | 1.99 |
| 5.00 | 1.96 | 0.55 | 1.72 |

These results show that the binding capacity in the GI simulant goes through a maximum as the crosslinker to amine ratio is varied. In this particular system the optimum binding capacity in the GI stimulant is observed at a crosslinker ratio of 1.75 to 3, corresponding to a NC value of 3.5 to 6 respectively. Within that range of crosslinking the swelling ratio is minimal. Similar tests routinely may be carried out for other monomers and crosslinkers using this polymerization protocol to determine the ratio that gives the desired results for the particular use to which the polymer will be put.

Example 10

Synthesis of Micron Sized, Crosslinked Particles from Ground Polyallylamine/ECH Bulk Gel using a 24 Well Parallel Polymerization Reactor This Example illustrates the synthesis of a polymer using a high molecular weight monomer and varying monomer to water ratios in the reaction mixture. The conditions employed were identical to those described in Example 8, except that polyallylamine (Mw=60,000 g/mole) was used instead of BTA. The ECH to allylamine repeat unit ratio was 1:0.106 (corresponding to a NC of 2.2). The initial polyallyamine to water ratio was varied from 1:1 to 1.4. As a comparative example, crosslinked polyallylamine isolated from Renagel tablets was used.

| Amine to water Mole ratio | BC (mmol/gr) Non interfering | BC (mmol/gr) Digested meal | Swelling ratio (gr. Water/ gr. Polymer) |
| --- | --- | --- | --- |
| 0.20 | 3.66 | 0.92 | 19.00 |
| 0.33 | 4.12 | 1.36 | 6.00 |
| 0.50 | 4.20 | 1.62 | 4.00 |
| Renagel | 3.85 | 1.40 | 9.00 |

These data indicate that a higher amine to water ratio led to a smaller swelling ratio and was accompanied by a higher binding capacity in the GI simulant. Similar tests routinely may be carried out for other monomers and crosslinkers using this polymerization protocol to determine the ratio that gives the desired results for the particular use to which the polymer will be put.

Example 11

Measure of the Binding Interference Level

This example illustrates the measurement of binding interference, using a polymer of the invention and, for comparison, a prior art polymer. A crosslinked polyamine material (EC172A) was prepared according to protocol described in Example 4, with a BTA:ECH mole ratio of 2.5, and a (BTA+ECH) to water ratio of 1.73. The binding interference was compared with Renagel.

The "degree of interference in binding" or "binding interference," as used herein, refers to the fractional decrease in binding capacity for the target ion observed between a binding experiment in a non interfering buffer, and in a gastrointestinal (GI) simulant, at the same concentration of target anion in equilibrium. A binding isotherm in a non interfering buffer was first obtained by plotting the binding capacity versus the phosphate concentration at equilibrium for a variety of phosphate concentrations. That isotherm was then fitted by an exponential function to predict the binding capacity at any phosphate concentration. The binding capacity measured in the GI simulant was then reported on the same isotherm, plotting the point of phosphate concentration versus phosphate binding at equilibrium for the GI simulant and extending a vertical line through this point to intersect the non-interfering isotherm. The interference degree was then computed as the (BCNI-BCGI)/BCNI*100.

Figure 3:
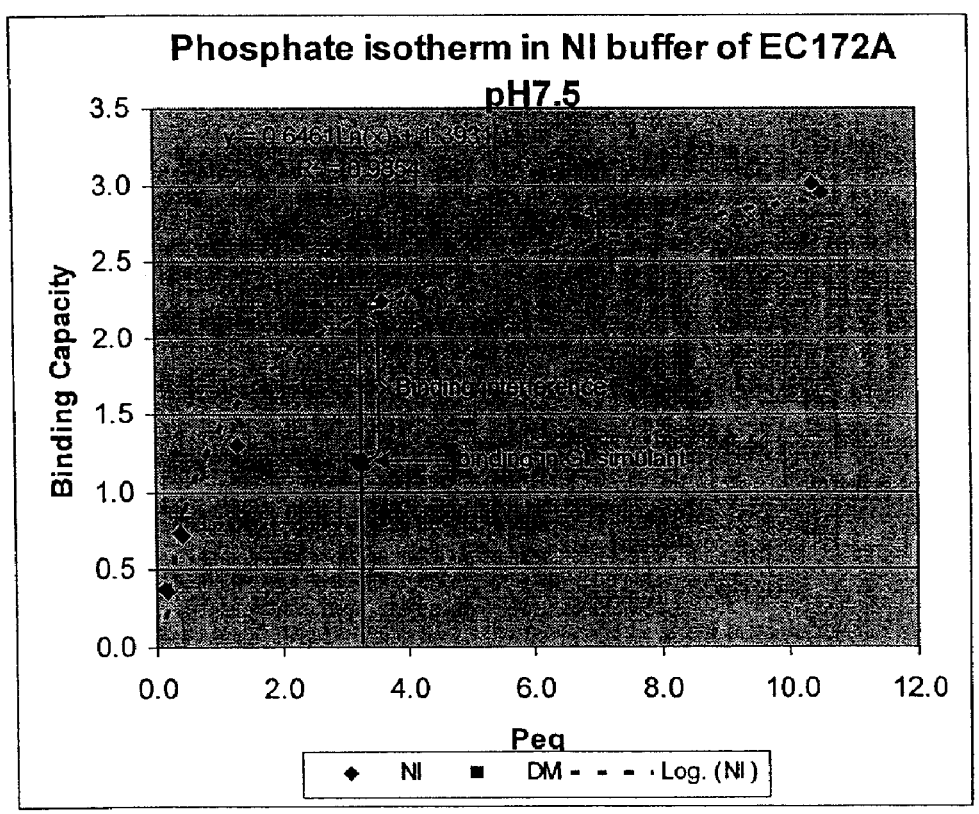
FIG. 3 is a graph illustrating the determination of binding interference for a phosphate-binding polymer (EC172A).

The binding interference is shown for EC127A is shown in the Table below and in FIG. 3.

| Pstart (mM) | Peq (mM) | BC (mmol/gr) | Predicted BC (mmol/gr) | Interference (%) |
|---|---|---|---|---|
| 6.25 | 3.31 | 1.18 | 2.17 | 45.7 |
| 6.25 | 3.28 | 1.19 | 2.16 | 45.0 |
| 6.25 | 3.24 | 1.21 | 2.15 | 44.0 |

Figure 4:
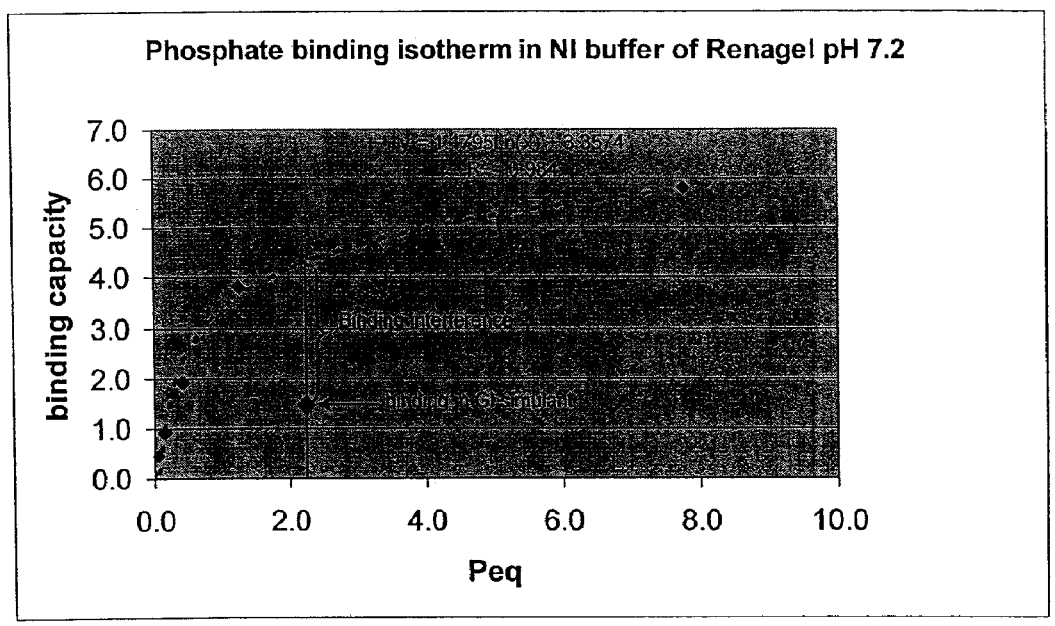
FIG. 4 is a graph illustrating the determination of binding interference for a phosphate-binding polymer (RENAGEL).

The binding interference for RENAGEL is shown in the Table below and in FIG. 4.

| Pstart (mM) | Peq (mM) | BC (mmol/gr) | Predicted BC (mmol/gr) | Interference (%) |
|---|---|---|---|---|
| 6.25 | 2.70 | 1.42 | 4.53 | 68.7 |
| 6.25 | 2.54 | 1.48 | 4.46 | 66.7 |

The binding interference for EC127A is about 34% lower than that of RENAGEL.

Example 12

Ion Binding Properties in Human ex-vivo Aspirates

A crosslinked polyamine material (EC172A) was prepared according to protocol described in Eample 4, with a BTA: ECH mole ratio of 2.5, and a (BTA+ECH) to water ratio of 1.73. The material was then tested for phosphate binding in a human aspirate collected as described in Example 1.

The binding of phosphate of EC172A was compared to that of crosslinked polyallyamine active pharmaceutical isolated from Renagel (Genzyme). EC172A exhibits a much lower level of interference, as well as a much lower index of swelling (2.5 vs. 9 for Renagel)

| | Avg Peq (mM) | SD (mM) | Avg BC (mmol/gr) | SD (mmol/gr) | Predicted BC (mmol/gr) | % interference |
|---|---|---|---|---|---|---|
| Renagel API | 2.37 | 0.01 | 1.32 | 0.00 | 4.37 | 70 |
| EC172A | 1.55 | 0.04 | 1.64 | 0.02 | 1.68 | 2.5 |

In another experiment both materials, EC172A and Renagel, were used in a different human ex-vivo aspirate to quantitate the degree of interference on phosphate binding produced by competing solutes such as citrate anions and bile acids. Citrate anions and bile acids were titrated by ion chromatography and enzymatic assay respectively. Data shown below (mean of six volunteers) indicate that the polymer of the present invention exhibit much better selectivity and overall binding of phosphate.

| | [PO4] mM | BC (PO4) mmol/g | [citrate] mM | BC (citrate) mmol/g | (Bile Acid) mM | BC (Bile) mmol/g |
|---|---|---|---|---|---|---|
| Control (no polymer) | 5.722 | | 1.667 | | 4.928 | |
| Renagel | 3.019 | 1.078 | 0.596 | 0.429 | 1.32 | 1.443 |
| EC172A | 1.78 | 1.573 | 1.316 | 0.141 | 4.65 | 0.109 |

Example 13

Gel Porosity Measurement using the Solute Partitioning Technique

This Example illustrates measurement of gel porosity. The measurements were carried out on a polymer of the invention, and on a commercially available phosphate-binding polymer for comparison. As a polymer of the invention, a crosslinked polyamine material (EC172A) was prepared according to protocol described in Example 10, with a BTA:ECH mole ratio of 2.5, and a (BTA+ECH) to water ratio of 1.73. For comparison, the same porosity measurements were carried out on Renagel.

The probes were 8 polyethyleneglycols (PEG) of MW ranging from 200 to 20,000 Da and 4 polyethyleneoxides (PEO) (30,000 to 230,000 Da).

All probes were dissolved in 30 mM ammonium acetate buffer pH 5.5 (concentration 5 g/L). The probe solutions were added to preweighed EC172A HCl wash (5 mL/g) and Renagel HCl wash (15 mL/g dry gel); then shaken for 4 days on a Vortexer.

Probe solutions were diluted 10× before LC analysis using Polymer Lab Evaporative Light Scattering Detector (in order to be in linear range of detector guaranteeing that peak area ratio is equal to weight concentration ratio).

Calculation of Non-accessible volume=$m_{sw}+[1-c_{before}/c_{after}]m_{solv}$; where $m_{sw}$ water amount uptaken by gel [g/g dry gel]

$m_{solv}$ water amount, in which the probe was dissolved at the beginning [g/g dry gel]

$c_{before}$ and $c_{after}$: concentrations of probe before and after equilibrium. The ratio $c_{before}/c_{after}$ is equal to ratio of the peak area obtained with LC analysis.

Figure 5:
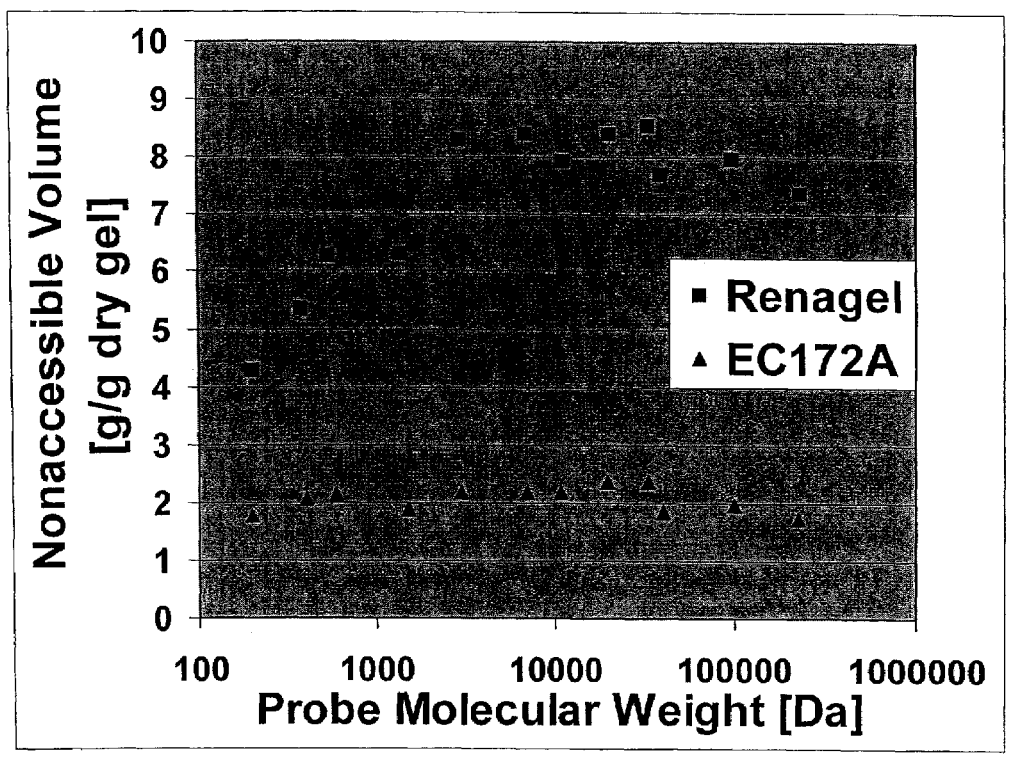
FIG. 5 is a plot of nonaccessible volume versus probe molecular weight, for non-interacting probes, illustrating the difference between a phosphate-binding polymer of the invention (EC 172A) and a commercially-available phosphate binder (RENAGEL).
Figure 6:
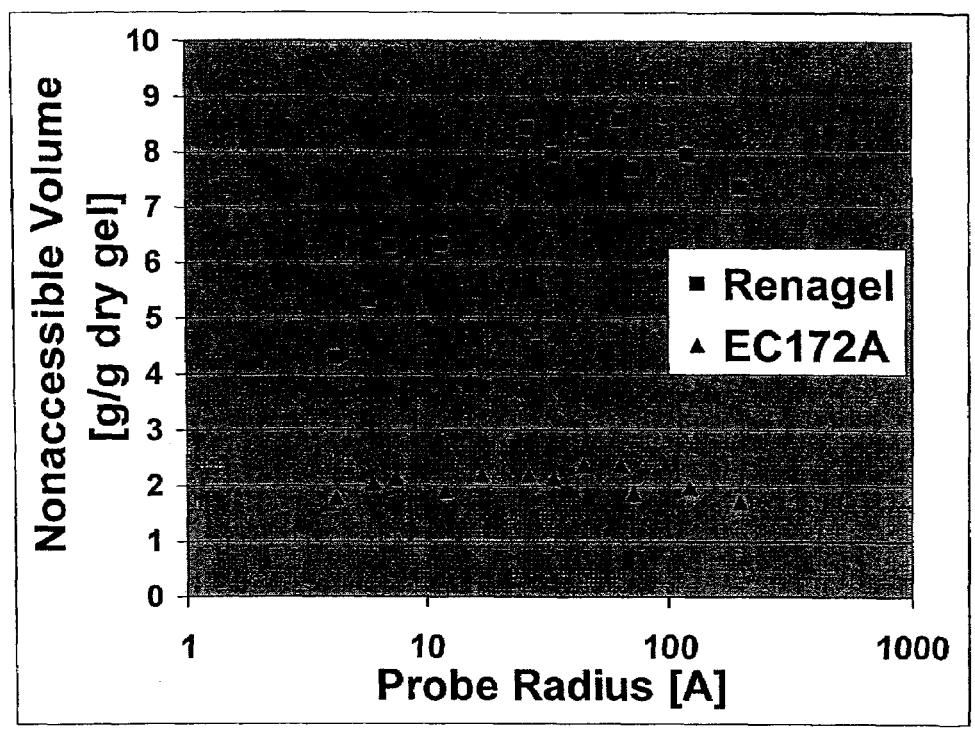
FIG. 6 is a plot of nonaccessible volume versus probe radius, for non-interacting probes illustrating the difference between a phosphate-binding polymer of the invention (EC 172A) and a commercially-available phosphate binder (RENAGEL).

The results of this comparative Example are shown in FIGS. 5 and 6; FIG. 5 illustrates the results in terms of molecular weight while FIG. 6 illustrates the results in terms of size of the solutes. EC127A shows constant molecular exclusion for solutes down to a MW of 200, as compared with Renagel, which demonstrates decreasing exclusion at MW as high as 1000.

Example 14

Post Modification of Beads with Chloropropylamine, Hydrochloride

Preparation of Stock Solution:
Chloropropylamine, hydrochloride (B-SM-34-A) in water at 50 wt. % –d=1.132
Sodium hydroxide in water at 30 wt. % (by dilution of a 50 wt. % solution) –d=1.335
Synthesis:
FR-0005-144, a phosphate binder polymer prepared according to Eample 9, with a BTA:ECH mole ratio of 2.5, and a (BTA+ECH) water ratio of 1.73, was used as a substrate for further aminification: The FR-0005-144 beads were transferred to 4mL-vials (two 4×6 plates containing each 21 vial) and water, chloropropylamine, hydrochloride stock solution and sodium hydroxide stock solution were added using a liquid dispensing robot. Vials were sealed with a cap, and plates were set up on reactors equipped with a heating system and individual stirring.

Heating and stirring were turned on for 12 hours: Reactor's temperature was set at 85° C. and stirring rate at 1200 rpm.

Purification:

Each material was transferred to disposable culture tubes (16×100 mm) and washed once with methanol, twice with an hydrochloric acid solution in water at 1M, and three times with water. Beads were separated each time by centrifugation.

Figure 7:
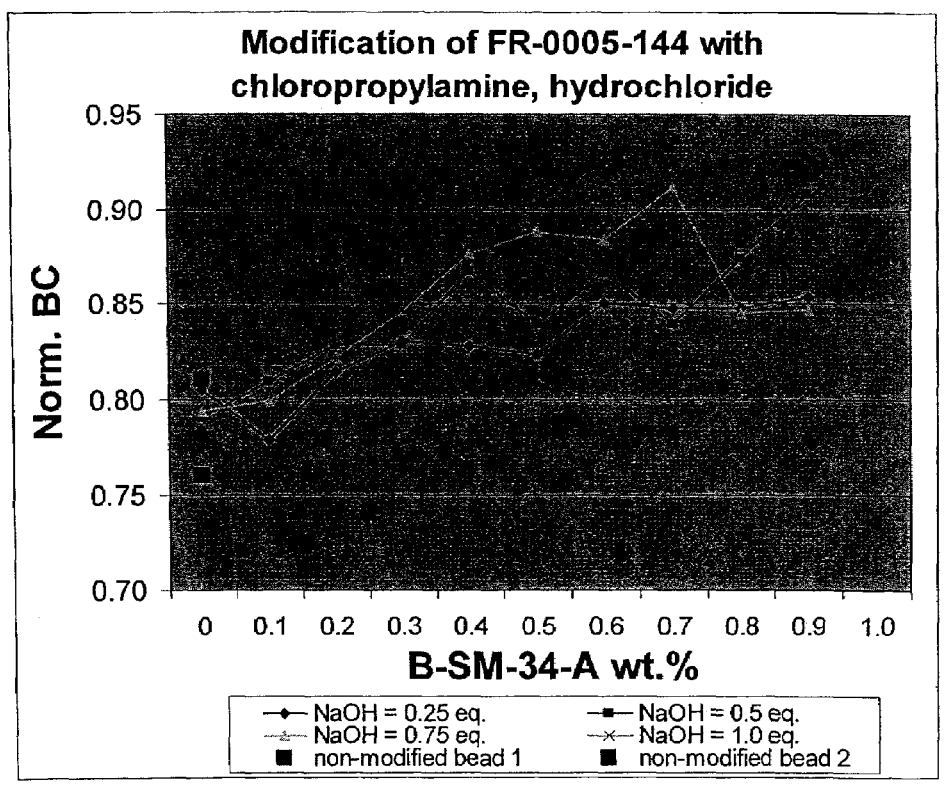
FIG. 7 is a graph illustrating the change in binding capacity with modification of FR-005-144 with chloropropylamine, hydrochloride.

They were then dried in a lyophilizer and analyzed for Digested Meal screen, Non-Interfering buffer and swelling ratio. The results are shown below in Table 12 and in FIG. 7.

TABLE 12

Characteristics of polymers prepared by post modification of beads with chloropropylamine, hydrochloride

| FR-0005-144 | water | B—SM-34-A | NaOH | B—SM-34-A wt. ratio vs FR-0005-144 | NaOH mol. Ratio (vs. B—SM-34-DA) | BC DM screen (mmol/gr) | BC NI Screen (mmol/g) | Swelling ratio (g of water/g of gel) |
|---|---|---|---|---|---|---|---|---|
| 222.1 | 864.5 | 22.2 | 1.71 | 0.1 | 0.25 | 0.94 | 2.84 | 2.91 |
| 233.3 | 883.0 | 46.7 | 3.59 | 0.2 | 0.25 | 0.91 | 2.94 | 2.69 |
| 203.7 | 749.0 | 61.1 | 4.70 | 0.3 | 0.25 | 0.95 | 2.85 | 2.83 |
| 209.1 | 746.3 | 83.6 | 6.43 | 0.4 | 0.25 | 0.97 | 2.91 | 2.64 |
| 209 | 723.5 | 104.5 | 8.04 | 0.5 | 0.25 | 0.97 | 2.89 | 2.58 |
| 0 | 0.0 | 0.0 | 0.00 | | | | | |
| 227 | 761.3 | 136.2 | 10.48 | 0.6 | 0.25 | 0.96 | 2.90 | 2.60 |
| 235 | 762.8 | 164.5 | 12.65 | 0.7 | 0.25 | 1.00 | 2.97 | 2.67 |
| 231.3 | 725.9 | 185.0 | 14.23 | 0.8 | 0.25 | 0.99 | 2.88 | 2.86 |
| 278.5 | 844.1 | 250.7 | 19.28 | 0.9 | 0.25 | 0.99 | 2.90 | 3.38 |
| 236.2 | 690.4 | 236.2 | 18.17 | 1.0 | 0.25 | 1.00 | 2.96 | 2.73 |
| 0 | 0.0 | 0.0 | 0.00 | | | | | |
| 204.1 | 792.9 | 20.4 | 3.14 | 0.1 | 0.5 | 0.92 | 2.81 | 2.85 |
| 271 | 1021.5 | 54.2 | 8.34 | 0.2 | 0.5 | 0.95 | 2.81 | 2.74 |
| 247 | 902.5 | 74.1 | 11.40 | 0.3 | 0.5 | 0.97 | 2.85 | 2.85 |
| 225.5 | 797.9 | 90.2 | 13.87 | 0.4 | 0.5 | 0.97 | 2.93 | 2.61 |
| 238.2 | 815.4 | 119.1 | 18.32 | 0.5 | 0.5 | 1.01 | 2.84 | 2.68 |
| 270.7 | 0.0 | 0.0 | 0.00 | | | 0.89 | 2.73 | 2.98 |
| 199.7 | 660.5 | 119.8 | 18.43 | 0.6 | 0.5 | 0.98 | 2.91 | 2.70 |
| 230.6 | 736.1 | 161.4 | 24.83 | 0.7 | 0.5 | 1.01 | 3.03 | 2.46 |
| 221.3 | 680.9 | 177.0 | 27.23 | 0.8 | 0.5 | 0.98 | 2.92 | 2.58 |
| 212.5 | 629.3 | 191.3 | 29.42 | 0.9 | 0.5 | 1.02 | 3.04 | 2.61 |
| 200.4 | 570.4 | 200.4 | 30.83 | 1.0 | 0.5 | 1.06 | 2.93 | 2.46 |
| 0 | 0 | 0 | 0 | | | | | |
| 213.1 | 826.17 | 21.3 | 4.92 | 0.1 | 0.75 | 0.94 | 2.80 | 2.92 |
| 203.7 | 764.66 | 40.7 | 9.40 | 0.2 | 0.75 | 0.94 | 2.81 | 2.82 |
| 212.4 | 771.18 | 63.7 | 14.70 | 0.3 | 0.75 | 0.97 | 2.84 | 3.04 |
| 218.2 | 765.38 | 87.3 | 20.14 | 0.4 | 0.75 | 1.00 | 2.88 | 2.99 |
| 203.4 | 688.43 | 101.7 | 23.47 | 0.5 | 0.75 | 1.03 | 2.90 | 2.64 |
| 0 | 0 | 0.0 | 0.00 | | | | | |
| 214.3 | 698.95 | 128.6 | 29.67 | 0.6 | 0.75 | 1.05 | 2.94 | 2.50 |
| 228.8 | 718.09 | 160.2 | 36.95 | 0.7 | 0.75 | 1.04 | 2.95 | 2.60 |
| 235.2 | 709.23 | 188.2 | 43.41 | 0.8 | 0.75 | 1.08 | 3.02 | 2.55 |
| 216.8 | 627.06 | 195.1 | 45.02 | 0.9 | 0.75 | 1.00 | 2.95 | 2.65 |
| 206.7 | 572.41 | 206.7 | 47.69 | 1.0 | 0.75 | 1.00 | 3.03 | 2.48 |
| 0 | 0 | 0.0 | 0.00 | | | | | |
| 199.7 | 772.69 | 20.0 | 6.14 | 0.1 | 1.0 | 0.97 | 2.75 | 2.85 |
| 206.4 | 771.62 | 41.3 | 12.70 | 0.2 | 1.0 | 0.97 | 2.77 | 3.30 |
| 216 | 779.26 | 64.8 | 19.94 | 0.3 | 1.0 | 0.98 | 2.83 | 2.93 |
| 213.3 | 741.63 | 85.3 | 26.25 | 0.4 | 1.0 | 1.00 | 2.85 | 3.43 |
| 212.9 | 712.4 | 106.5 | 32.75 | 0.5 | 1.0 | 1.04 | 2.95 | 2.66 |
| 193.3 | 0 | 0.0 | 0.00 | | | 0.95 | 2.73 | 2.95 |
| 240.6 | 773.63 | 144.4 | 44.41 | 0.6 | 1.0 | 1.02 | 2.94 | 2.88 |
| 294.5 | 908.43 | 206.2 | 63.42 | 0.7 | 1.0 | 1.07 | 2.94 | 2.58 |
| 214.1 | 632.43 | 171.3 | 52.69 | 0.8 | 1.0 | 1.06 | 3.05 | 2.60 |
| 205.5 | 580.15 | 185.0 | 56.90 | 0.9 | 1.0 | 1.08 | 3.04 | 2.66 |
| 201.2 | 541.7 | 201.20 | 61.90 | 1.0 | 1.0 | 1.09 | 3.07 | 2.91 |
| 0 | 0 | 0.00 | 0.00 | | | | | |

Example 15

Synthesis of Phosphate-Templated Micron Sized, Crosslinked Particles from N,N'(Tetra-3-Aminopropyl)1,4 Diaminobutane/Epichlorohydrin The following stock solution was prepared: 1 molar equivalent of Phosphoric acid (Aldrich, 85 wgt % in water) was added to 1 molar equivalent of N,N'(tetra-3-aminopropyl)1,4 diaminobutane over a 2 hour period. Water was then added to the solution such that the resulting solution achieved the following weight % composition: N,N'(tetra-3-aminopropyl)1,4 diaminobutane 42 weight %, $H_3PO_4$ 13 weight %, water 45 weight %. The reactor contained 24 wells used 5 mL flasks, each flask containing a magnetic stir bar. Into each flask was placed 0.6-0.7 g of the prepared stock solution. The stirrers were on. The desired amount of epichlorohydrin was added neat to each vial. The reactor was heated to 60° C. for 1 hour and then heated to 80° C. for 8 hours. The reactor was allowed to cool. To each vial was added water to swell the resulting gel. The gel was transferred to a 4×6 plate with 10 mL test tubes. The gel was then ground to micron sized particles with a mechanical grinder (Brand: IKA. Model: Ultra-Turax T8). The particles were purified by removing the water, washing with methanol and further washing with a 20% solution of NaOH. The gel particles were subsequently washed with 1.0 molar HCl, mixed for 30 minutes, then the gel was allowed to settle and the supernatant liquid was decanted off. This process was repeated 5 times to protonate the amine functionalized particle with Chloride and replace the bound $H_3PO_4$. The gel particles were then washed with a 20% solution of NaOH to deprotonate the amine functionalized gel particles. The gel particles were then washed twice with deionized water to remove excess NaOH/NaCl. The gel particles were freeze dried for 3 days to give a fine white powder. The synthesis is summarized in Table 13.

The polymers synthesized as described above bind phosphate.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for treating hyperphosphatemia in an animal afflicted with renal insufficiency, the method comprising orally administering an effective amount of a phosphate binding polymer to the animal, the phosphate binding polymer being a crosslinked amine polymer comprising repeat units derived from polymerization of a non-polymeric amine and a crosslinking agent, the polymer having a swelling ratio of less than about 5 as measured in a physiological medium which is isotonic and neutral pH, the non-polymeric amine being (i) an amine of formula (I)

wherein each n, independently, is equal to or greater than 3; m is equal to or greater than 1; and each $R_1$, independently, is H or optionally substituted alkyl or aryl or is linked to a neigh-

TABLE 13

Synthesis of gels that have been Molecular imprinted with Phosphoric acid. ID 102776

| Row | Col | B—SM-20-TeA (mg) | B—SM-20-TeA (Moles) | phosphoric acid (mg) | water (mg) | X-EP-1 (mg) | X-EP-1 (Moles) | B—SM-20-TeA/ H3PO4 | X-Ep-1/ B—SM-20-TeA | Gel Present in well |
|---|---|---|---|---|---|---|---|---|---|---|
| 1.0 | 1.0 | 347.5 | 0.0011 | 107.7 | 369.8 | 71.1 | 0.0008 | 1.00 | 0.70 | x |
| 1.0 | 2.0 | 339.5 | 0.0011 | 105.2 | 361.4 | 79.4 | 0.0009 | 1.00 | 0.80 | x |
| 1.0 | 3.0 | 337.7 | 0.0011 | 104.6 | 359.4 | 88.8 | 0.0010 | 1.00 | 0.90 | ✓ |
| 1.0 | 4.0 | 352.1 | 0.0011 | 109.1 | 374.8 | 102.9 | 0.0011 | 1.00 | 1.00 | ✓ |
| 1.0 | 5.0 | 355.4 | 0.0011 | 110.1 | 378.2 | 114.3 | 0.0012 | 1.00 | 1.10 | ✓ |
| 1.0 | 6.0 | 366.1 | 0.0012 | 113.4 | 389.6 | 128.4 | 0.0014 | 1.00 | 1.20 | ✓ |
| 2.0 | 1.0 | 355.3 | 0.0011 | 110.1 | 378.1 | 135.0 | 0.0015 | 1.00 | 1.30 | ✓ |
| 2.0 | 2.0 | 338.6 | 0.0011 | 104.9 | 360.4 | 138.6 | 0.0015 | 1.00 | 1.40 | ✓ |
| 2.0 | 3.0 | 356.2 | 0.0011 | 110.4 | 379.1 | 156.2 | 0.0017 | 1.00 | 1.50 | ✓ |
| 2.0 | 4.0 | 349.7 | 0.0011 | 108.3 | 372.2 | 163.5 | 0.0018 | 0.99 | 1.61 | ✓ |
| 2.0 | 5.0 | 342.2 | 0.0011 | 106.0 | 364.2 | 170.0 | 0.0018 | 1.00 | 1.70 | ✓ |
| 2.0 | 6.0 | 351.4 | 0.0011 | 108.9 | 374.1 | 184.9 | 0.0020 | 1.00 | 1.80 | ✓ |
| 3.0 | 1.0 | 364.1 | 0.0012 | 112.8 | 387.5 | 212.8 | 0.0023 | 1.00 | 2.00 | ✓ |
| 3.0 | 2.0 | 351.2 | 0.0011 | 108.8 | 373.8 | 246.4 | 0.0027 | 1.00 | 2.40 | ✓ |
| 3.0 | 3.0 | 358.3 | 0.0011 | 111.0 | 381.4 | 293.2 | 0.0032 | 1.00 | 2.81 | ✓ |
| 3.0 | 4.0 | 340.2 | 0.0011 | 105.4 | 362.1 | 318.2 | 0.0034 | 1.00 | 3.20 | ✓ |
| 3.0 | 5.0 | 368.9 | 0.0012 | 114.3 | 392.6 | 388.2 | 0.0042 | 1.00 | 3.59 | ✓ |
| 3.0 | 6.0 | 360.5 | 0.0011 | 111.7 | 383.7 | 421.5 | 0.0046 | 1.00 | 4.00 | ✓ |
| 4.0 | 1.0 | 345.3 | 0.0011 | 107.0 | 367.5 | 444.0 | 0.0048 | 1.00 | 4.40 | ✓ |
| 4.0 | 2.0 | 364.0 | 0.0012 | 112.8 | 387.4 | 510.7 | 0.0055 | 1.00 | 4.80 | ✓ |
| 4.0 | 3.0 | 351.2 | 0.0011 | 108.8 | 373.7 | 533.7 | 0.0058 | 1.00 | 5.20 | ✓ |
| 4.0 | 4.0 | 365.5 | 0.0012 | 113.2 | 389.0 | 598.3 | 0.0065 | 0.99 | 5.63 | ✓ |
| 4.0 | 5.0 | 358.5 | 0.0011 | 111.1 | 381.6 | 628.8 | 0.0068 | 1.00 | 6.02 | ✓ | boring R₁ to form an optionally substituted alicyclic, aromatic, or heterocyclic group; or (ii) an amine of formula (IV)

$$N\text{---}\left[\begin{array}{c}R_1\\|\\\text{---}(C)_n\text{---}\\|\\R_1\end{array}\underset{2-r}{(R_1)}N\text{---}\left[\begin{array}{c}R_1\\|\\\text{---}(C)_n\text{---}\\|\\R_1\end{array}N\begin{array}{c}R_1\\\diagup\\\diagdown\\R_1\end{array}\right]_r\right]_3 \quad\text{(IV)}$$

wherein each n, independently, is equal to or greater than 3; each r, independently, is 0, 1, or 2; and each $R_1$, independently, is H or optionally substituted alkyl or aryl or is linked to a neighboring $R_1$ to form an optionally substituted alicyclic, aromatic, or heterocyclic group; provided the non-polymeric amine is not 1,3-diaminopropane or N,N'-(tetra-3-aminopropyl)-1,4-diaminobutane.

2. The method of claim 1 wherein the animal is a human.

3. The method of claim 1 wherein the animal is a human and is afflicted with chronic kidney disease.

4. The method of claim 1 wherein the animal is a human and is afflicted with end stage renal disease (ESRD).

5. The method of claim 1 wherein the crosslinked amine polymer is active for removing phosphate ions from the gastrointestinal tract.

6. The method of claim 1 wherein the crosslinked amine polymer binds phosphate ion in vivo with a binding capacity of greater than 0.5 mmol/g.

7. The method of claim 1 wherein the crosslinked amine polymer comprises repeat units of the non-polymeric amine plus intervening linker units.

8. The method of claim 1 wherein the crosslinked amine polymer is insoluble in a physiological isotonic buffer.

9. The method of claim 1 wherein the crosslinked amine polymer is formulated as a free amine, free of counter-ions.

10. The method of claim 1 wherein the crosslinked amine polymer is in the form of spherical beads.

11. The method of claim 1 wherein the crosslinked amine polymer comprises repeat units derived from polymerization of a non-polymeric amine having a molecular weight less than 200 g/mol and a crosslinking agent.

12. The method of claim 1 wherein the crosslinked amine polymer is a copolymer comprising several different non-polymer amine moieties and a crosslinking agent.

13. The method of claim 1 wherein the crosslinked amine polymer is a copolymer comprising non-polymeric diamine, triamine or tetramine moieties and a crosslinking agent.

14. The method of claim 1 wherein the crosslinking agent is a compound having at least two functional groups, each functional group being selected from halogen, carbonyl, epoxy, ester, acid anhydride, acid halide, isocyanate, vinyl, and chloroformate.

15. The method of claim 1 wherein the crosslinking agent is 1,3-dichloropropane or epichlorohydrin.

16. The method of claim 1 wherein the molar ratio of crosslinking agent to amine ranges from about 0.2 to about 10.

17. The method of claim 1 wherein less than about 20% of the polymer pore volume is accessible to non-interacting solutes of molecular weight greater than about 200.

18. The method of claim 1 wherein less than about 20% of the polymer pore volume is accessible to non-interacting solutes of molecular weight greater than about 180.

19. The method of claim 1 wherein less than about 20% of the polymer pore volume is accessible to non-interacting solutes of molecular weight greater than about 160.

20. The method of claim 1 wherein less than about 20% of the polymer pore volume is accessible to non-interacting solutes of molecular weight greater than about 140.

21. The method of claim 1 wherein the crosslinked amine polymer has an ion-binding interference for phosphate lower than about 60% when measured in a gastrointestinal simulant, relative to a non-interfering buffer.

22. The method of claim 1 wherein the crosslinked amine polymer has an ion-binding interference for phosphate lower than about 40% when measured in a gastrointestinal simulant, relative to a non-interfering buffer.

23. The method of claim 1 wherein the crosslinked amine polymer has an ion-binding interference for phosphate lower than about 20% when measured in a gastrointestinal simulant, relative to a non-interfering buffer.

24. The method of claim 1 wherein the crosslinked amine polymer binds bile acids or citrate with a capacity of less than about 2 mmol/gram.

25. The method of claim 1 wherein the crosslinked amine polymer has a swelling ratio in physiological isotonic buffer of less than about 3.

26. The method of claim 1 wherein the crosslinked amine polymer has a swelling ratio in physiological isotonic buffer of less than about 2.8.

27. The method of claim 1 wherein the crosslinked amine polymer comprises repeat units derived from polymerization of a non-polymeric amine having a formula $$H_2N\diagdown\qquad\diagup NH_2$$
$$\qquad N\text{---}(CH_2)_n\text{---}N$$
$$H_2N\diagup\qquad\diagdown NH_2$$

wherein n is 3 or 5, and a crosslinking agent.

28. The method of claim 27 wherein n is 3.

29. The method of claim 27 wherein n is 5.

30. The method of claim 27 wherein the crosslinking agent is 1,3-dichloropropane or epichlorohydrin.

31. The method of claim 27 wherein the crosslinking agent is epichlorohydrin.

32. The method of claim 27 wherein the molar ratio of crosslinking agent to amine ranges from about 0.2 to about 5.

33. The method of claim 27 wherein the crosslinked amine polymer comprises repeat units derived from polymerization of a copolymer comprising a diamine and a crosslinking agent.

34. The method of claim 27 wherein the crosslinking agent is epichlorohydrin, the molar ratio of crosslinking agent to amine ranges from about 0.2 to about 5, the polymer is insoluble in a physiological isotonic buffer, the crosslinked amine polymer has a swelling ratio in physiological isotonic buffer ranging from about 2 to 20, and the crosslinked amine polymer has a binding capacity in a non-interfering buffer ranging from about 2.5 mmol/g to about 8 mmol/g.

35. The method of claim 1 wherein the crosslinked amine polymer comprises repeat units derived from polymerization of a non-polymeric amine selected from

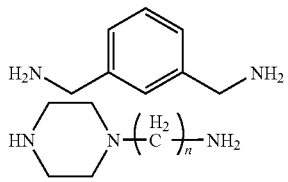

wherein n is 3, 4 or 5, and a crosslinking agent.

36. The method of claim 1 wherein the crosslinked amine polymer comprises repeat units derived from polymerization of 1,2,3,4-tetraminobutane and a crosslinking agent.

37. The method of claim 1 wherein the crosslinked amine polymer comprises repeat units derived from polymerization of the non-polymeric amine of formula

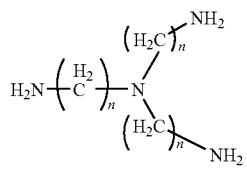

wherein each n, independently, is equal to or greater than 3, and a crosslinking agent.

38. The method of claim 1 wherein the crosslinked amine polymer comprises repeat units derived from polymerization of the non-polymeric amine having a formula selected from

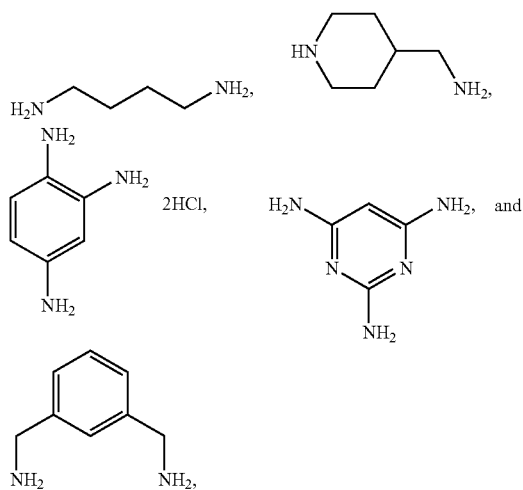

and a crosslinking agent.

39. The method of claim 1 wherein the phosphate binding polymer is co-administered with another active pharmaceutical agent selected from at least one of a proton pump inhibitor, a calcimimetic, a vitamin, and analogs thereof.

40. The method of claim 1 wherein the phosphate binding polymer is co-administered with another active pharmaceutical agent phosphate binder.

41. The method of claim 1 wherein the other active pharmaceutical agent phosphate binder is selected from at least one of calcium carbonate, calcium acetate, lanthanum carbonate, or polyallylamine hydrochloride.

42. The method of claim 1 wherein the phosphate binding polymer is administered as a pharmaceutical composition in the form of a chewable tablet and/or a mouth-disintegrating tablet.

43. The method of claim 1 wherein the phosphate binding polymer is administered as a pharmaceutical composition in the form of a liquid formulation.

44. The method of claim 1 wherein the phosphate binding polymer is administered as a pharmaceutical composition in the form of a powder.

45. The method of claim 1 wherein the phosphate binding polymer is administered as a pharmaceutical composition in doses ranging from about 1 gram/day to about 30 gram/day.

46. The method of claim 1 wherein the phosphate binding polymer is administered as a pharmaceutical composition in doses ranging from about 2 gram/day to about 20 gram/day.

47. The method of claim 1 wherein the phosphate binding polymer is administered as a pharmaceutical composition in doses ranging from about 3 gram/day to about 7 gram/day.

48. The method of claim 1 wherein the phosphate binding polymer is administered as a pharmaceutical composition one time per day, two times per day or three times per day.

49. A method for treating hyperphosphatemia in an animal, the method comprising orally administering an effective amount of a phosphate binding polymer to the animal, the phosphate binding polymer being a crosslinked amine polymer comprising repeat units derived from polymerization of a non-polymeric amine and a crosslinking agent, the polymer having a swelling ratio of less than about 5 as measured in a physiological medium which is isotonic and neutral pH, the non-polymeric amine being selected from the group consisting of (i) an amine of formula (I)

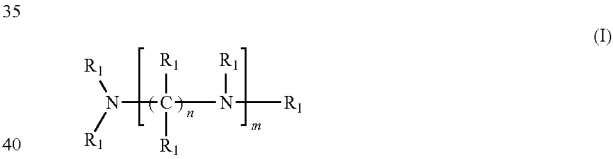

wherein each n, independently, is equal to or greater than 3; m is equal to or greater than 1; and each $R_1$, independently, is H or optionally substituted alkyl or aryl or is linked to a neighboring $R_1$ to form an optionally substituted alicyclic, aromatic, or heterocyclic group; provided the non-polymeric amine of formula I is not 1,3-diaminopropane, and (ii) an amine of formula (IV)

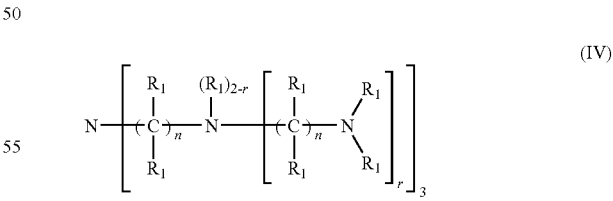

wherein each n, independently, is equal to or greater than 3; each r, independently, is 0, 1, or 2; and each $R_1$, independently, is H or optionally substituted alkyl or aryl or is linked to a neighboring $R_1$ to form an optionally substituted alicyclic, aromatic, or heterocyclic group, the phosphate binding polymer being in the form of spherical beads having a size in the range of 5 to 500 microns.

50. A method for removing phosphate in an animal suffering from renal insufficiency, the method comprising orally administering an effective amount of a phosphate binding polymer to the animal, the phosphate binding polymer being a crosslinked amine polymer comprising repeat units derived from polymerization of a non-polymeric amine and a crosslinking agent, the polymer having a swelling ratio of less than about 5 as measured in a physiological medium which is isotonic and neutral pH, the non-polymeric amine being selected from the group consisting of (i) an amine of formula (I)

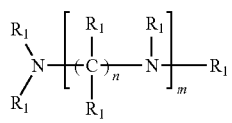

(I)

wherein each n, independently, is equal to or greater than 3; m is equal to or greater than 1; and each $R_1$, independently, is H or optionally substituted alkyl or aryl or is linked to a neighboring $R_1$ to form an optionally substituted alicyclic, aromatic, or heterocyclic group; provided the non-polymeric amine of formula I is not 1,3-diaminopropane, and (ii) an amine of formula (IV)

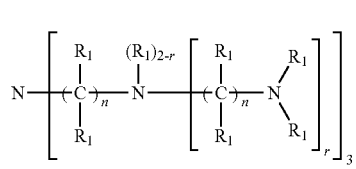

(IV)

wherein each n, independently, is equal to or greater than 3; each r, independently, is 0, 1, or 2; and each $R_1$, independently, is H or optionally substituted alkyl or aryl or is linked to a neighboring $R_1$ to form an optionally substituted alicyclic, aromatic, or heterocyclic group, the phosphate binding polymer being in the form of spherical beads having a size in the range of 5 to 500 microns.

51. The method of claim 49 wherein said animal is afflicted with end stage renal disease (ESRD).

52. The method of claim 49 wherein the crosslinked amine polymer comprises repeat units derived from polymerization of the amine corresponding to the structure

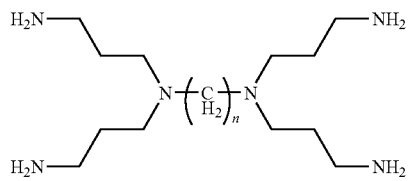

wherein n is 3, 4, or 5, and the crosslinking agent.

53. The method of claim 49 wherein the crosslinked amine polymer consists essentially of repeat units derived from polymerization of the amine corresponding to the structure

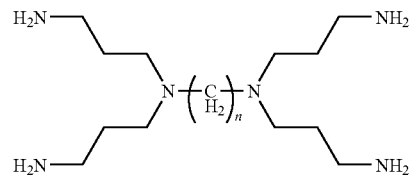

wherein n is 3, 4, or 5, and the crosslinking agent.

54. The method of claim 49 wherein the crosslinked amine polymer is formulated into a pharmaceutical composition for oral delivery.

55. The method of claim 54 wherein the composition is in the form of a powder.

56. The method of claim 54 wherein the composition is contained within a sachet.

57. The method of claim 54 wherein the composition is in the form of a sterile packaged powder.

58. The method of claim 54 wherein the composition is in the form of a soft or hard gelatin capsule.

59. The method of claim 50 wherein said animal is afflicted with end stage renal disease (ESRD).

60. The method of claim 50 wherein the crosslinked amine polymer comprises repeat units derived from polymerization of the amine corresponding to the structure

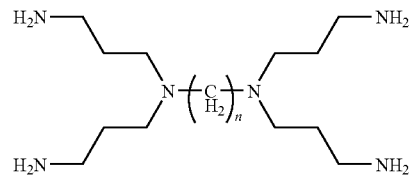

wherein n is 3, 4, or 5, and the crosslinking agent.

61. The method of claim 50 wherein the crosslinked amine polymer consists essentially of the polymerization product of the amine corresponding to the structure

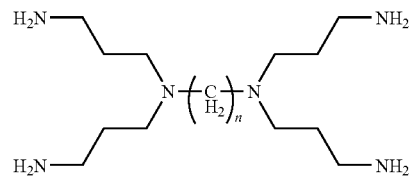

wherein n is 3, 4, or 5, and a crosslinking agent.

62. The method of claim 50 wherein the polymer is formulated into a pharmaceutical composition for oral delivery.

63. The method of claim 62 wherein the composition is in the form of a powder.

64. The method of claim 62 wherein the composition is contained within a sachet.

65. The method of claim 62 wherein the composition is in the form of a sterile packaged powder.

66. The method of claim 62 wherein the composition is in the form of a soft or hard gelatin capsule.

* * * * *

UNITED STATES PATENT AND TRADEMARK OFFICE
CERTIFICATE OF CORRECTION

PATENT NO. : 7,589,238 B2  
APPLICATION NO. : 11/465444  
DATED : September 15, 2009  
INVENTOR(S) : Connor et al.

Page 1 of 1

It is certified that error appears in the above-identified patent and that said Letters Patent is hereby corrected as shown below:

On the Title Page of the patent, Section 75, Inventors:

"Gerrit Klaemer, San Jose, CA (US)"

should read

--Gerrit Klaerner, San Jose, CA (US)--.

Signed and Sealed this
First Day of February, 2011

David J. Kappos
*Director of the United States Patent and Trademark Office*